United States Patent
Stanfield et al.

(10) Patent No.: US 11,759,389 B2
(45) Date of Patent: Sep. 19, 2023

(54) WEARABLE DEVICES, SYSTEMS, METHODS AND ARCHITECTURES FOR SENSORY STIMULATION AND MANIPULATION AND PHYSIOLOGICAL DATA ACQUISITION

(71) Applicant: IFTECH INVENTING FUTURE TECHNOLOGY INC., Oshawa (CA)

(72) Inventors: Michael Gerald Stanfield, Blackstock (CA); Brodie Myles Stanfield, Blackstock (CA)

(73) Assignee: IFTECH INVENTING FUTURE TECHNOLOGY, INC., Ontario (CA)

( * ) Notice: Subject to any disclaimer, the term of this patent is extended or adjusted under 35 U.S.C. 154(b) by 887 days.

(21) Appl. No.: 15/108,598

(22) PCT Filed: Dec. 31, 2014

(86) PCT No.: PCT/CA2014/000916
§ 371 (c)(1),
(2) Date: Jun. 28, 2016

(87) PCT Pub. No.: WO2015/100482
PCT Pub. Date: Jul. 9, 2015

(65) Prior Publication Data
US 2016/0317383 A1    Nov. 3, 2016

Related U.S. Application Data

(60) Provisional application No. 61/922,197, filed on Dec. 31, 2013.

(51) Int. Cl.
*A61H 23/00*  (2006.01)
*A61N 1/04*   (2006.01)
(Continued)

(52) U.S. Cl.
CPC ......... *A61H 23/0254* (2013.01); *A41D 13/12* (2013.01); *A61B 5/6804* (2013.01);
(Continued)

(58) Field of Classification Search
CPC ..... A61N 1/0484; A61B 5/6804; A63F 13/25; A63F 13/28; A63F 13/285; A63F 2300/8082; G06F 3/011; G06F 3/016
See application file for complete search history.

(56) References Cited

U.S. PATENT DOCUMENTS

| 3,610,250 A | * | 10/1971 | Sarbacher | ............ | A61N 1/0452 |
| | | | | | 607/149 |
| 4,586,495 A | | 5/1986 | Petrofsky | | |

(Continued)

FOREIGN PATENT DOCUMENTS

| GB | 2362329 A | 11/2001 |
| GB | 2409798 A | 7/2005 |

OTHER PUBLICATIONS

International Search Report for PCT/CA2014/000916 dated Mar. 19, 2015.
(Continued)

*Primary Examiner* — Tu A Vo
*Assistant Examiner* — Christopher E Miller
(74) *Attorney, Agent, or Firm* — Joseph F. Murphy; Potomac Law Group, PLLC

(57) ABSTRACT

A garment with prepositioned, definite sensory stimulating devices attached. These sensory stimulating devices include, but are not limited to, electrical stimulation, audio and physical stimulation such as localised force generation, compression, constriction, vibration, and surround sound. Predetermined and defined actuators allow the wearer to receive tissue, nerve and/or muscle stimulation and/or contraction so that the stimulation is precise as determined by its
(Continued)

US 11,759,389 B2

Page 2 ability to conform to the scientific methodology of repeatability, reproducibility and reliability; this being due to consistency of actuator positioning in one or multiple locals on the human body. A personal surround sound can also be integrated to the garment to ensure the wearer is always in the optimal position relative the speakers. These actuators can be force generators within the garment for the wearer to feel impact or apparatus or electrodes included in the garment to locally constrict and increase pressure on the wearer.

21 Claims, 41 Drawing Sheets

(51) Int. Cl.
A61H 23/02 (2006.01)
A41D 13/12 (2006.01)
A61B 5/00 (2006.01)
A61H 99/00 (2006.01)
A61H 3/06 (2006.01)
A61H 23/04 (2006.01)
A61H 9/00 (2006.01)
A61N 1/36 (2006.01)
A61F 7/02 (2006.01)
A61N 1/32 (2006.01)
A61B 5/0533 (2021.01)

(52) U.S. Cl.
CPC .............. *A61F 7/02* (2013.01); *A61H 3/061* (2013.01); *A61H 9/0078* (2013.01); *A61H 23/0236* (2013.01); *A61H 23/0245* (2013.01); *A61H 23/04* (2013.01); *A61H 99/00* (2013.01); *A61N 1/0452* (2013.01); *A61N 1/0456* (2013.01); *A61N 1/0484* (2013.01); *A61N 1/323* (2013.01); *A61N 1/36031* (2017.08); *A61N 1/36034* (2017.08); *A61B 5/0533* (2013.01); *A61B 2562/0204* (2013.01); *A61F 2007/0234* (2013.01); *A61H 2003/063* (2013.01); *A61H 2201/025* (2013.01); *A61H 2201/10* (2013.01); *A61H 2201/164* (2013.01); *A61H 2201/165* (2013.01); *A61H 2201/1614* (2013.01); *A61H 2201/1619* (2013.01); *A61H 2201/1623* (2013.01); *A61H 2201/1628* (2013.01); *A61H 2201/1635* (2013.01); *A61H 2201/501* (2013.01); *A61H 2201/5015* (2013.01); *A61H 2201/5043* (2013.01); *A61H 2201/5046* (2013.01); *A61H 2201/5097* (2013.01); *A61H 2205/06* (2013.01); *A61H 2230/04* (2013.01); *A61H 2230/06* (2013.01); *A61H 2230/30* (2013.01); *A61H 2230/40* (2013.01); *A61H 2230/50* (2013.01)

(56) References Cited

U.S. PATENT DOCUMENTS

| 5,474,452 | A | * | 12/1995 | Campagnuolo | F41G 3/26 102/401 |
|---|---|---|---|---|---|
| 5,549,656 | A | * | 8/1996 | Reiss | A61N 1/36003 600/546 |
| 5,913,727 | A | * | 6/1999 | Ahdoot | A63F 13/28 463/39 |
| 6,047,203 | A | * | 4/2000 | Sackner | A61N 1/0452 600/388 |
| 6,070,269 | A | * | 6/2000 | Tardif | G06F 3/011 2/69 |
| 6,422,941 | B1 | * | 7/2002 | Thorner | A63F 13/02 463/30 |
| 7,052,276 | B2 | * | 5/2006 | Davidsson | F41G 3/2655 434/11 |
| 7,072,721 | B1 | | 7/2006 | Trent | |
| 7,138,976 | B1 | * | 11/2006 | Bouzit | G06F 3/014 345/156 |
| 7,381,192 | B2 | * | 6/2008 | Brodard | A61H 1/0255 601/33 |
| 7,559,768 | B2 | * | 7/2009 | Marmaropoulos | G09B 23/183 439/37 |
| 8,308,489 | B2 | * | 11/2012 | Lee | H01R 13/2407 2/69 |
| 2002/0032386 | A1 | * | 3/2002 | Sackner | A61B 5/6804 600/536 |
| 2002/0058972 | A1 | * | 5/2002 | Minogue | A61N 1/321 607/72 |
| 2002/0077688 | A1 | * | 6/2002 | Kirkland | A61N 1/0452 607/142 |
| 2003/0162595 | A1 | * | 8/2003 | Serbanescu | G06F 3/016 472/1 |
| 2003/0208830 | A1 | * | 11/2003 | Marmaropoulos | A61N 1/0484 2/69 |
| 2003/0227374 | A1 | * | 12/2003 | Ling | G09B 21/003 340/407.1 |
| 2003/0234823 | A1 | * | 12/2003 | Sato | G06F 3/0346 715/848 |
| 2004/0174337 | A1 | * | 9/2004 | Kubota | G06F 3/016 345/156 |
| 2004/0254624 | A1 | * | 12/2004 | Johnson | A61N 1/0452 607/149 |
| 2005/0012485 | A1 | * | 1/2005 | Dundon | G06F 3/011 703/7 |
| 2005/0113167 | A1 | * | 5/2005 | Buchner | A63F 13/02 463/30 |
| 2005/0132290 | A1 | * | 6/2005 | Buchner | G06F 3/011 715/702 |
| 2005/0250582 | A1 | * | 11/2005 | Lopez | A63F 13/285 463/47 |
| 2005/0261564 | A1 | * | 11/2005 | Ryu | A61B 5/6804 600/388 |
| 2005/0275416 | A1 | * | 12/2005 | Hervieux | A61B 5/24 324/663 |
| 2005/0283204 | A1 | * | 12/2005 | Buhlmann | A61N 1/36003 607/48 |
| 2006/0079824 | A1 | * | 4/2006 | Munch-Fals | A61H 23/02 602/60 |
| 2006/0247733 | A1 | * | 11/2006 | Amer | A41D 1/00 607/48 |
| 2007/0049814 | A1 | * | 3/2007 | Muccio | A61N 1/0452 600/388 |
| 2008/0097530 | A1 | * | 4/2008 | Muccio | A61N 1/0452 607/3 |
| 2008/0153590 | A1 | * | 6/2008 | Ombrellaro | F41H 1/02 463/30 |
| 2009/0023122 | A1 | * | 1/2009 | Lieberman | G16H 20/70 434/258 |
| 2009/0069081 | A1 | * | 3/2009 | Thorner | A63F 13/285 463/30 |
| 2009/0131165 | A1 | * | 5/2009 | Buchner | G06F 3/016 463/30 |
| 2009/0262967 | A1 | * | 10/2009 | Bryan | H04R 5/02 381/333 |
| 2009/0326406 | A1 | * | 12/2009 | Tan | G06F 3/017 600/546 |
| 2010/0010568 | A1 | * | 1/2010 | Brown | A61H 1/008 2/69 |
| 2010/0016921 | A1 | * | 1/2010 | Campos | A61N 1/36021 607/48 |
| 2010/0052898 | A1 | * | 3/2010 | Allen | A61B 5/4875 340/539.12 |
| 2010/0154102 | A1 | * | 6/2010 | Leung | A63F 13/28 2/243.1 |
| 2010/0185259 | A1 | * | 7/2010 | Shiba | A61H 39/002 607/48 |

(56) References Cited

U.S. PATENT DOCUMENTS

| | | | |
|---|---|---|---|
| 2010/0217413 A1* | 8/2010 | Seiler | H04R 1/02 700/94 |
| 2010/0256475 A1* | 10/2010 | Chiang | A61B 5/6805 600/388 |
| 2010/0256704 A1* | 10/2010 | Annicelli | A61N 1/0484 607/48 |
| 2011/0046687 A1* | 2/2011 | Naschberger | A61H 23/00 607/3 |
| 2011/0063208 A1* | 3/2011 | Van Den Eerenbeemd | G06F 3/011 345/156 |
| 2011/0077728 A1* | 3/2011 | Li | A61H 39/002 607/152 |
| 2011/0087115 A1* | 4/2011 | Sackner | A61B 5/0205 600/484 |
| 2011/0087300 A1* | 4/2011 | Van Den Eerenbeemd | A63F 13/28 607/2 |
| 2011/0166491 A1* | 7/2011 | Sankai | A61B 5/0492 601/84 |
| 2011/0183752 A1* | 7/2011 | Bey | A63F 13/245 463/30 |
| 2012/0004523 A1* | 1/2012 | Richter | A61B 5/0002 600/345 |
| 2012/0051579 A1* | 3/2012 | Cohen | A61H 23/0236 381/388 |
| 2012/0064492 A1* | 3/2012 | Pearce | F41G 3/26 434/22 |
| 2012/0065561 A1* | 3/2012 | Ballas | A61H 9/0021 601/152 |
| 2012/0172940 A1* | 7/2012 | Wahls | A41D 1/005 607/3 |
| 2012/0188158 A1* | 7/2012 | Tan | A61B 5/0488 345/156 |
| 2012/0190460 A1* | 7/2012 | Sessions | A63F 13/02 463/47 |
| 2012/0238845 A1* | 9/2012 | Yang | A61B 5/6804 600/322 |
| 2012/0245483 A1* | 9/2012 | Lundqvist | A61B 5/0492 600/546 |
| 2012/0246795 A1* | 10/2012 | Scheffler | A41D 1/002 2/69 |
| 2013/0041272 A1* | 2/2013 | Guillen | A61B 5/02438 600/509 |
| 2013/0041297 A1* | 2/2013 | Garcia | A61H 23/0218 601/18 |
| 2013/0085420 A1* | 4/2013 | Feinstein | A61N 1/0468 601/5 |
| 2013/0198625 A1* | 8/2013 | Anderson | G06F 3/016 715/701 |
| 2013/0204169 A1* | 8/2013 | Poepperling | A61H 9/0078 601/46 |
| 2013/0317400 A1* | 11/2013 | Ferezy | A61N 1/0484 602/2 |
| 2014/0056461 A1* | 2/2014 | Afshar | H04R 1/00 381/385 |
| 2014/0070957 A1* | 3/2014 | Longinotti-Buitoni | A61B 5/6804 340/870.01 |
| 2014/0085414 A1* | 3/2014 | Zhou | G06F 3/011 348/43 |
| 2014/0111414 A1* | 4/2014 | Hayner | G06F 1/163 345/156 |
| 2014/0135644 A1* | 5/2014 | Kim | A61B 5/7455 600/545 |
| 2014/0135960 A1* | 5/2014 | Choi | G09B 19/0038 700/91 |
| 2014/0142459 A1* | 5/2014 | Jayalth | A61B 5/318 600/547 |
| 2014/0171838 A1* | 6/2014 | Aleksov | A61H 1/0244 601/33 |
| 2014/0206976 A1* | 7/2014 | Thompson | G16Z 99/00 600/391 |
| 2014/0318699 A1* | 10/2014 | Longinotti-Buitoni | A61B 5/6805 156/247 |
| 2015/0070145 A1* | 3/2015 | Mar | G06F 3/016 340/407.1 |
| 2015/0105129 A1* | 4/2015 | Chapman | A63F 13/212 463/7 |
| 2015/0142082 A1* | 5/2015 | Simon | A61N 1/36053 607/61 |
| 2015/0173640 A1* | 6/2015 | Chappell | A61B 5/0531 600/388 |
| 2015/0202429 A1* | 7/2015 | Fritzsche | A61N 1/0484 607/48 |
| 2015/0250420 A1* | 9/2015 | Longinotti-Buitoni | G01L 1/22 600/301 |
| 2015/0297437 A1* | 10/2015 | Neuenhahn | A61B 5/4848 601/148 |
| 2015/0301603 A1* | 10/2015 | Maggiali | G06F 3/0443 345/174 |
| 2015/0335288 A1* | 11/2015 | Toth | A61B 5/6833 600/373 |
| 2016/0256066 A1* | 9/2016 | Chetelat | A61B 5/04085 |
| 2016/0346153 A1* | 12/2016 | Hodges, IV | A61F 7/02 |

OTHER PUBLICATIONS

Queensland Brain Institute "Types of Neurons" Retrieved from the Internet: https://qbi.uq.edu.au/brain/brain-anatomy/types-neurons Jan. 27, 2021.

DifferenceBetween.com "Difference Between Sensory and Motor Nerves". Retrieved from the Internet: https://www.differencebetween.com/difference-between-sensory-and-motor-nerves/ Jan. 27, 2021.

Diabetes.co.uk "Nerves and Diabetes" Retrieved from the Internet: https://www.diabetes.co.uk/body/nerves.html Jan. 27, 2021.

WebMD.com "What are the types of nerves in the body?" Retrieved from the Internet: https://www.webmd.com/brain/qa/what-are-the-types-of-nerves-in-the-body Jan. 27, 2021.

* cited by examiner

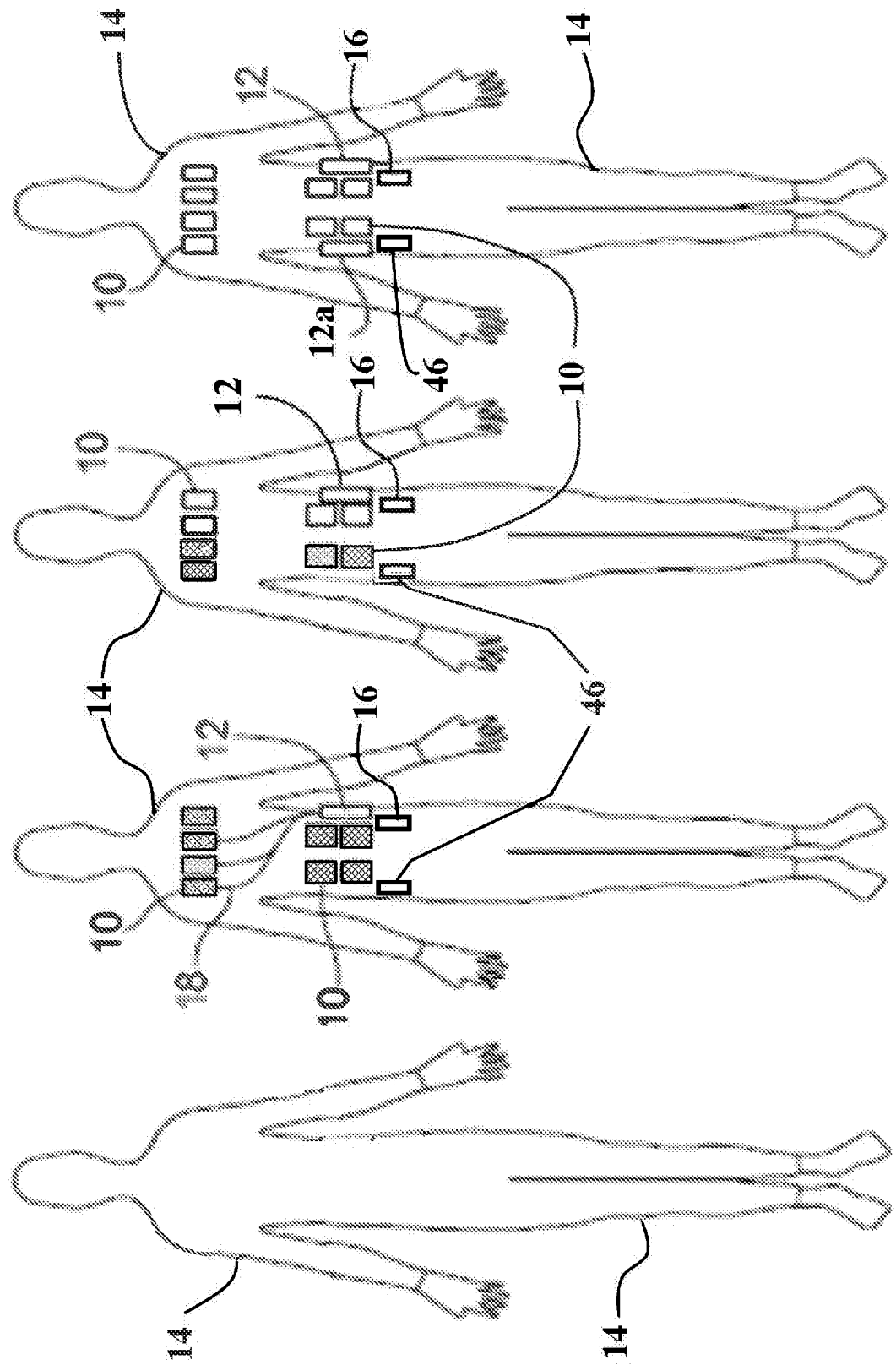

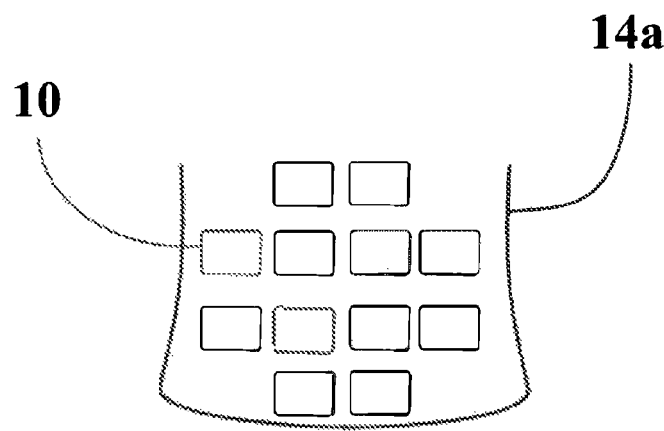
Figure 5a
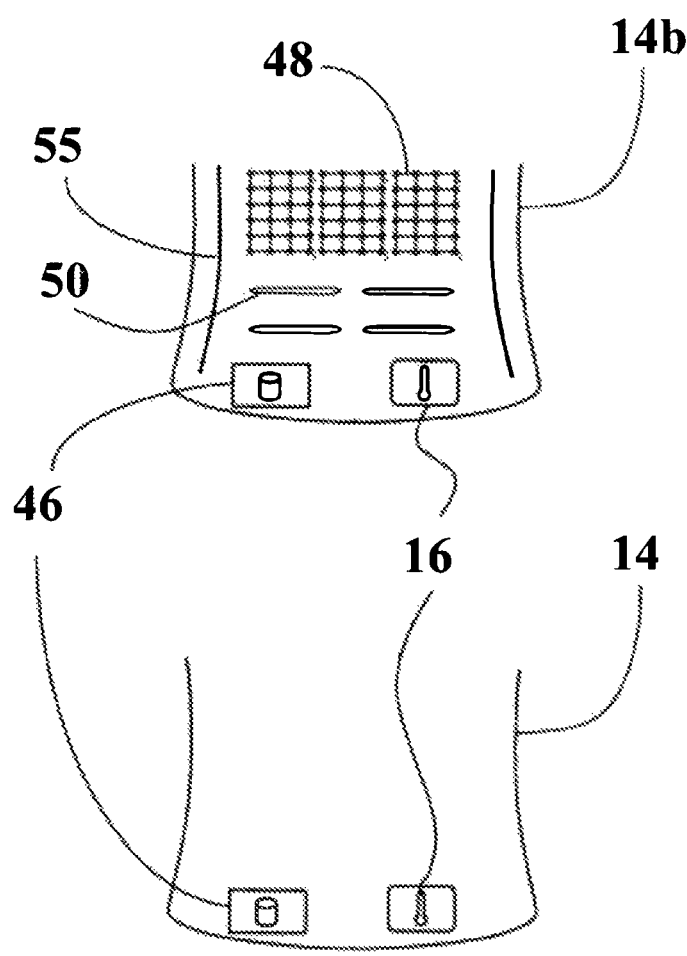
Figure 5b
Figure 5c

Exoskeleton Overview Specifications

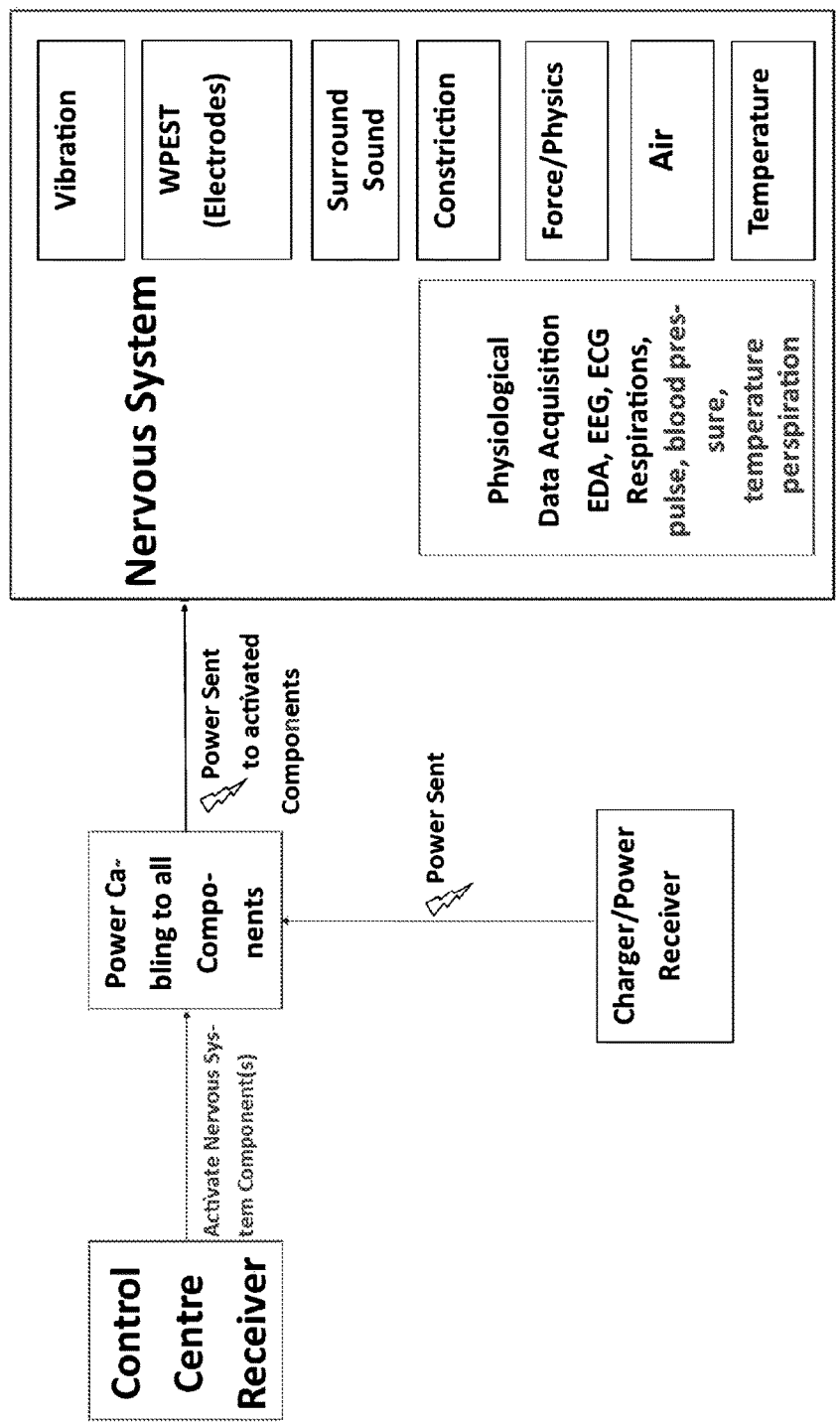

Nervous System — Vibration Specifications

Activating one or more Vibration Component

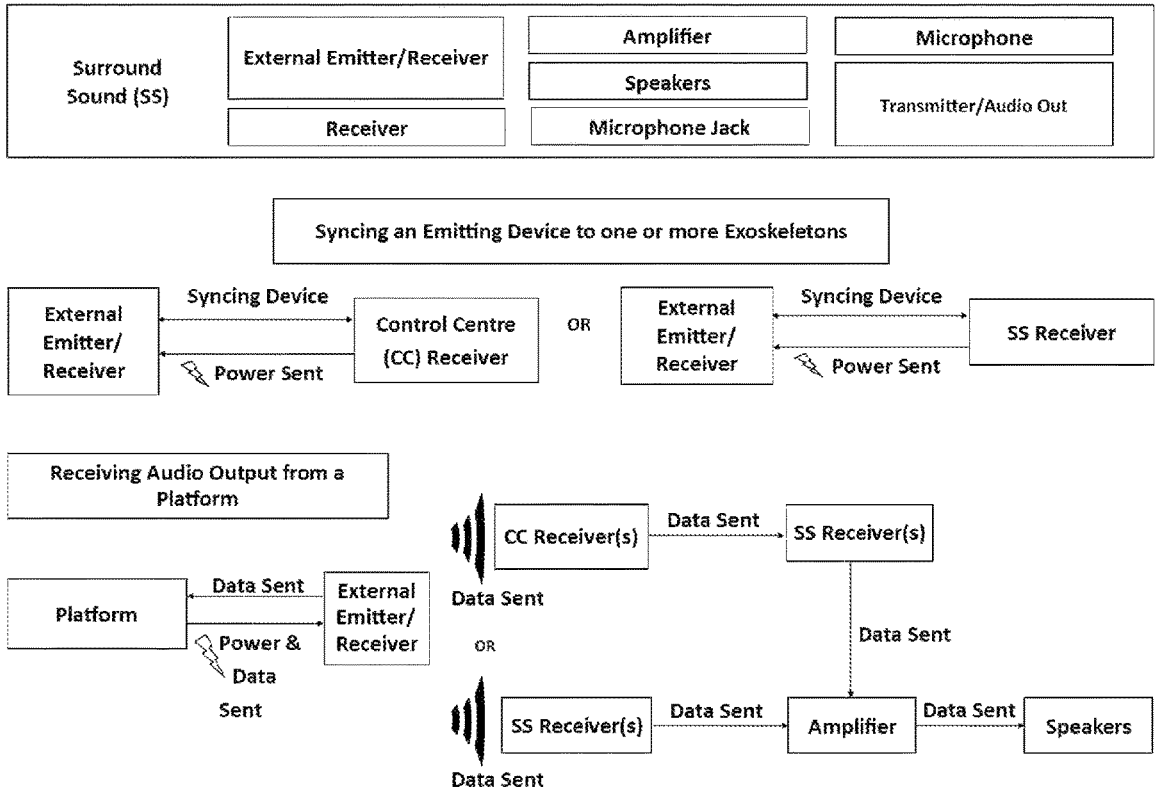
Figure 20a
Figure 20a Continued
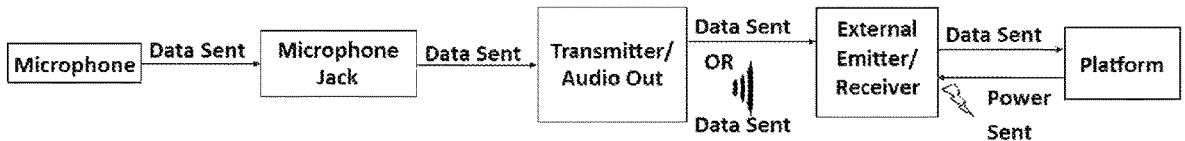
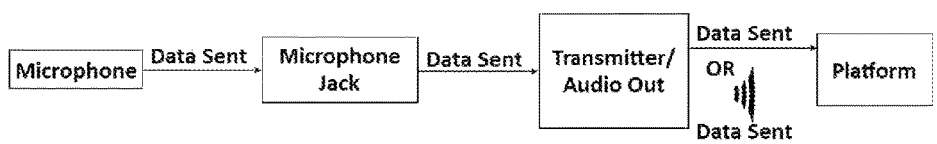

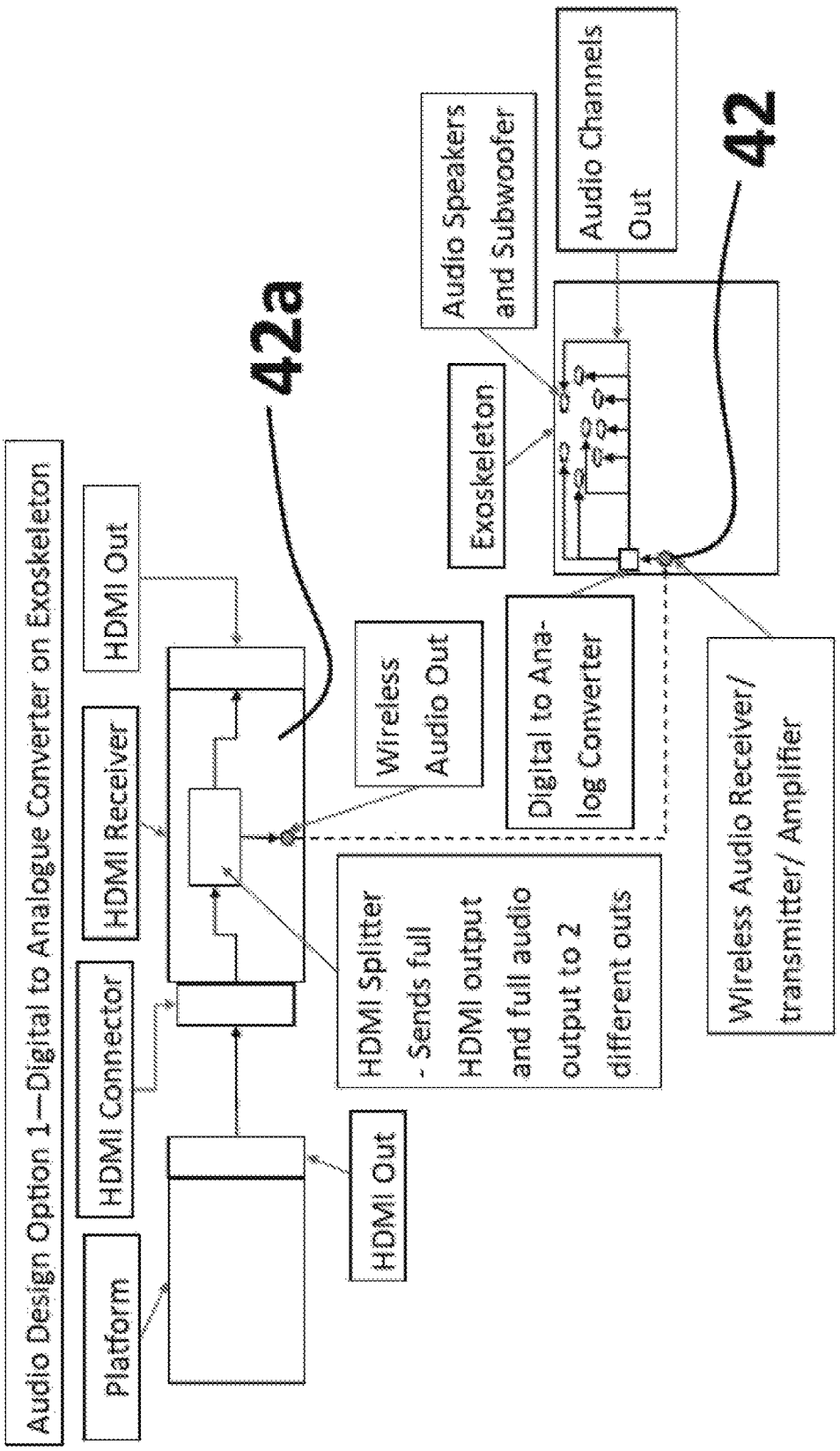

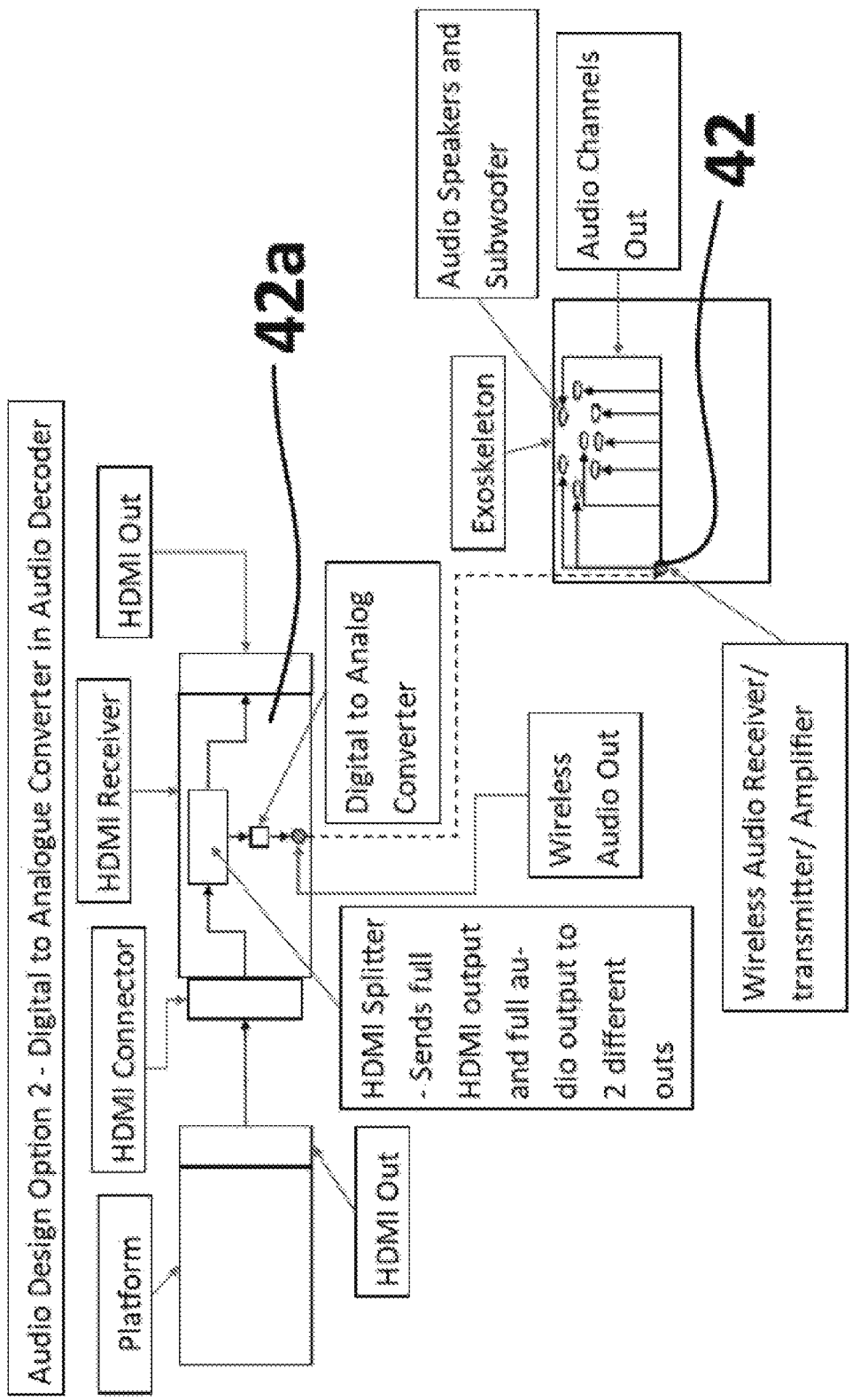

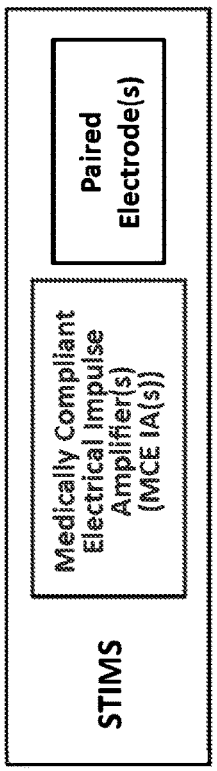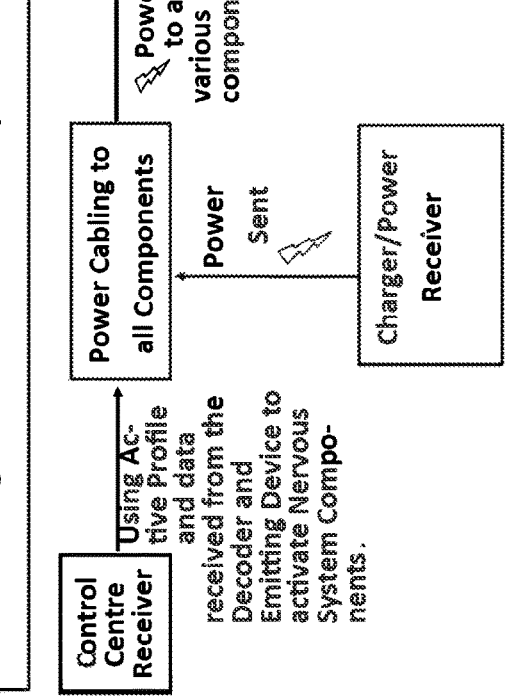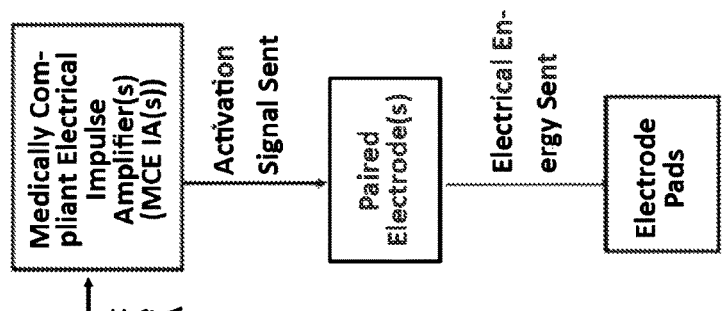
Figure 24

Legend - Key

| Symbol | Description |
|---|---|
| ⊖ | Single electrode negative polarity - Depiction of totally viewed Sensory Device (electrode) in full placement. |
| ⊟ ⊡ | Single electrode negative polarity - Depiction of partial view as Sensory Device (electrode) wraps around body part where placement occurs. |
| ⊕ | Single electrode positive polarity - Depiction of totally viewed Sensory Device (electrode) in full placement. |
| ⊞ ⊞ | Single electrode positive polarity - Depiction of partial view as Sensory Device (electrode) wraps around body part where placement occurs. |
| ∿ / — | Designates the connected pair of electrodes which activate as a pair. |
| ■ | Single vibration unit - Depiction of totally viewed Sensory Device in full placement. |
| ◆ | Single vibration unit - Depiction of partial view as Sensory Device is located on body part that is not totally obscured. |
| ● | Micro Board for Sensory Device Operation - Depiction of totally viewed Sensory Device in full placement. Receives input wirelessly; receives power through hard wire connection; choose Sensory Device(s); provides power which activate Sensory Device (switches power on); determines intensity of activation of Sensory Device; stops power which deactivates Sensory Device (switches power off). |
| ▲ ▼ | Micro Board for Sensory Device operation - Depiction of partial view as Sensory Device is located on body part that is not totally obscured. |

Figure 25

Pairing/ connections each containing one negative (-) and one positive (+) and each electrode pair is on a single circuit with no branched connection to any other electrode pairing.

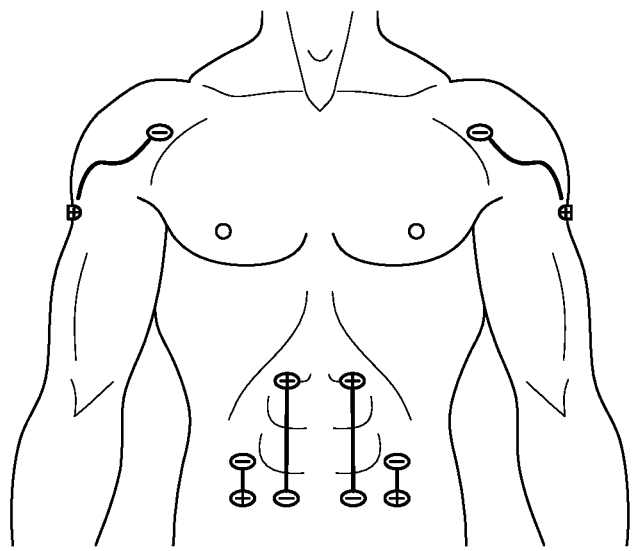

Frontal torso with electrodes placed at the deltoids and Abdominals

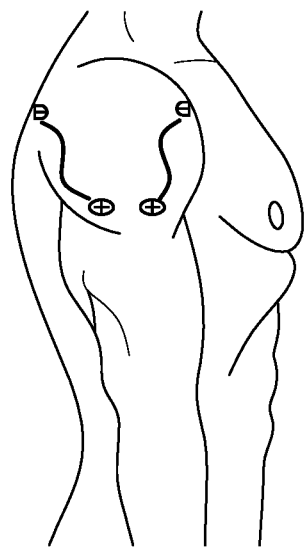

Side torso right with electrodes placed at the deltoids

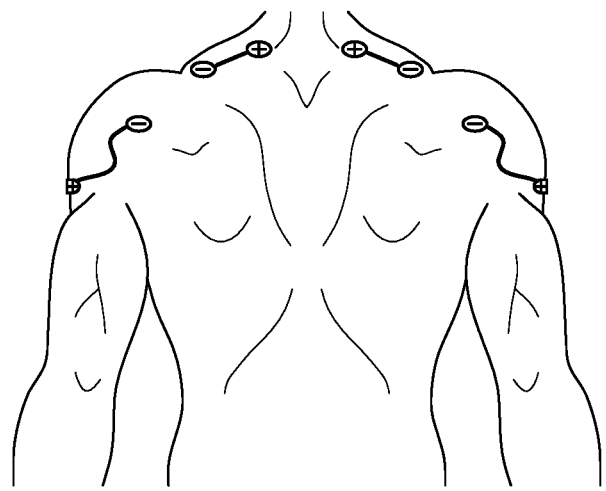

Back of torso with electrodes placed at the deltoids and Trapezius

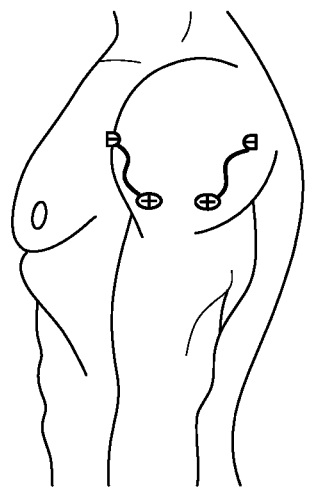

Side torso left with electrodes placed at the deltoids

Figure 26

Pairing/ connections each containing one negative (-) and one positive (+) and each electrode pair is on a single circuit with no branched connection to any other electrode pairing.

Frontal lower body with electrodes placed at the Quadriceps

Rear lower body with electrodes placed at the Gluteus, Hamstrings (bicep femoris), and Gastrocnemius Pairing/ connections each containing one negative (-) and one positive (+) and each electrode pair is on a single circuit with no branched connection to any other electrode pairing.

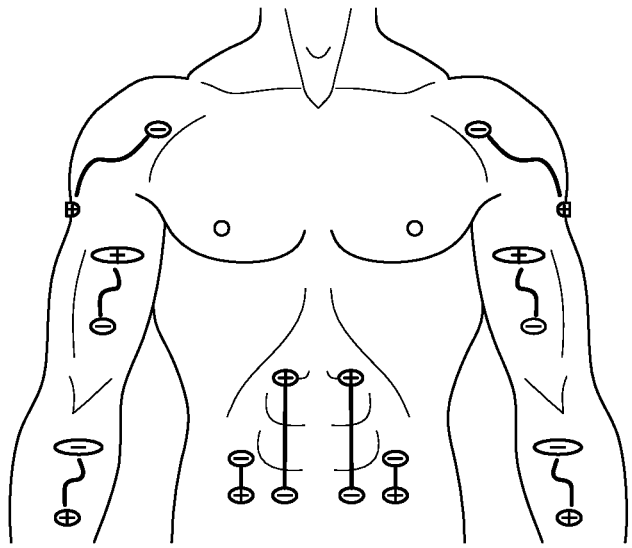

Frontal torso with electrodes placed at the Deltoids, Abdominals, Biceps, Forearms (Flexor Carpi)

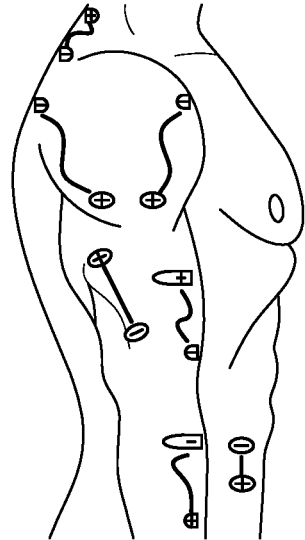

Right side torso view - electrodes placed at the Trapezius, Deltoids, Biceps, Triceps, Forearms (Extensor)

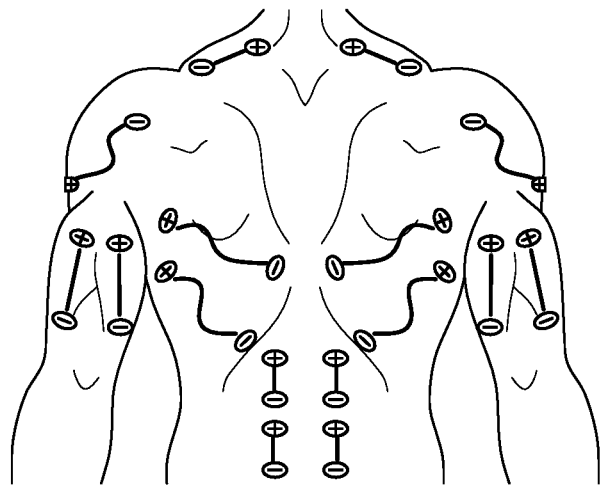

Back torso electrodes placed at the Deltoids, Trapezius, Latissimus Dorsi, Extensor Spinae

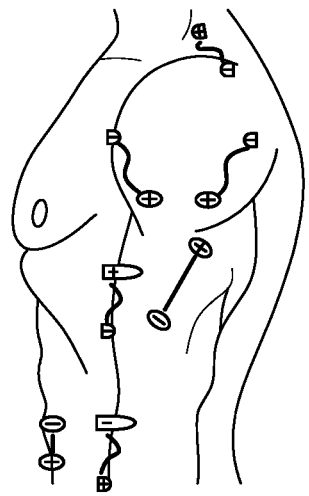

Left side torso view - electrodes placed at the Trapezius, Deltoids, Biceps, Triceps, Forearms (Extensor)

Figure 28

Pairing/ connections each containing one negative (-) and one positive (+) and each electrode pair is on a single circuit with no branched connection to any other electrode pairing.

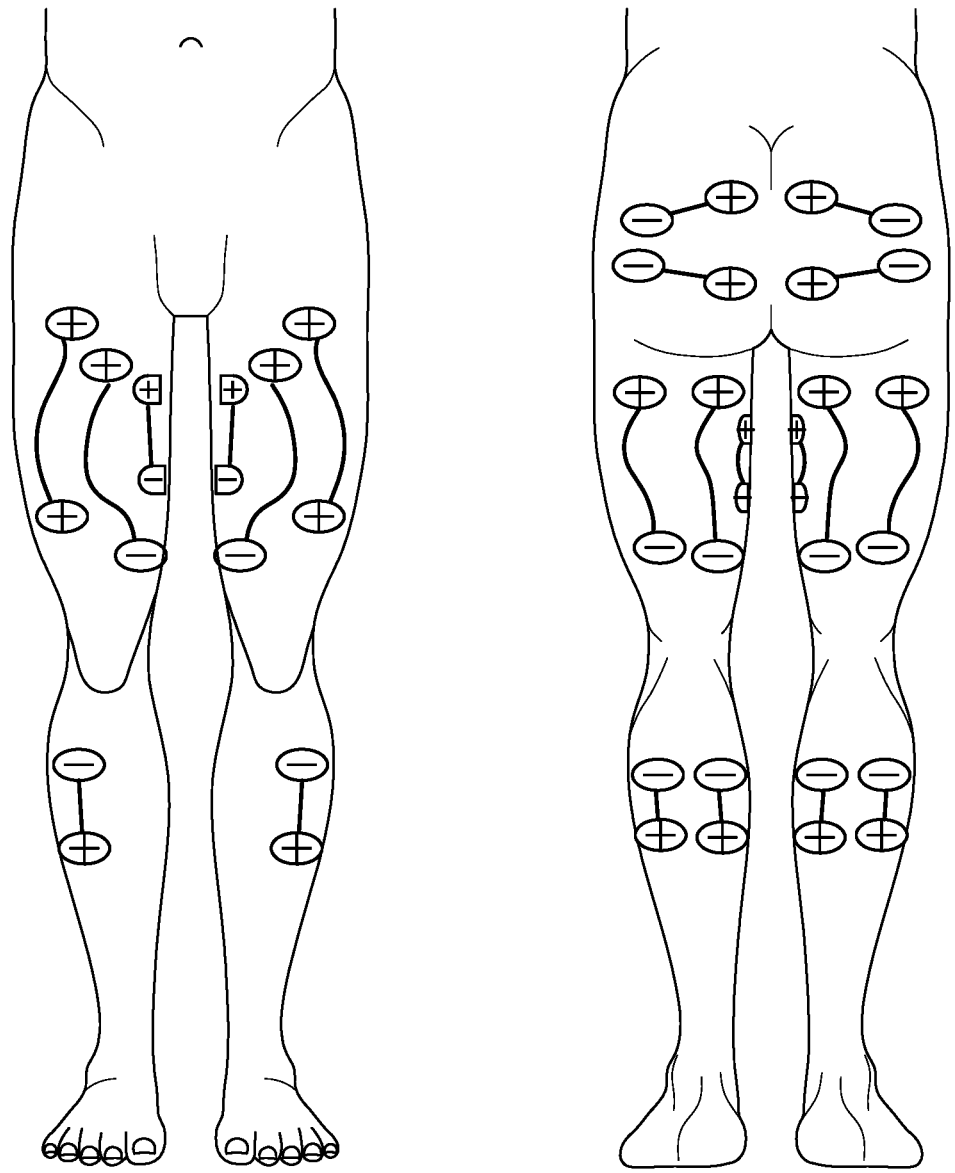

Frontal lower body with electrodes placed at the Adductors, Quardriceps, and Tribialis Rear lower body with electrodes placed at the Gluteus, Hamstring (bicep femoris), Adductors and Gastrocnemius

Figure 29

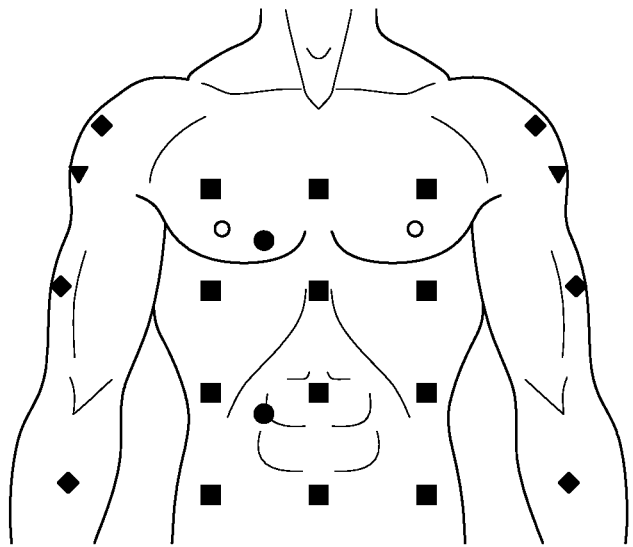

Frontal torso with vibration placed in grid formation over chest and abdomen, centrally located on outside of upper arm between the bicep and triceps, on the shoulder and inside and outside of forearm (lower arm). Most likely placement of Micro Board.

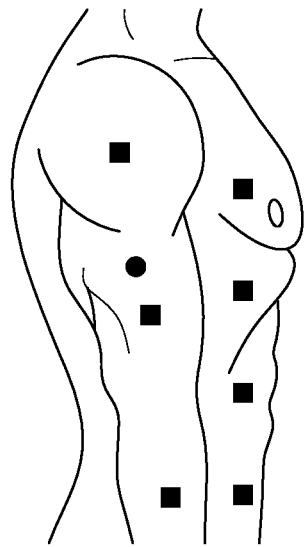

Side torso right with vibration at deltoids, centrally located on outside of upper arm between the bicep and triceps. Abdomen, and inside and outside of forearm (lower arm). Most likely placement of Micro Board.

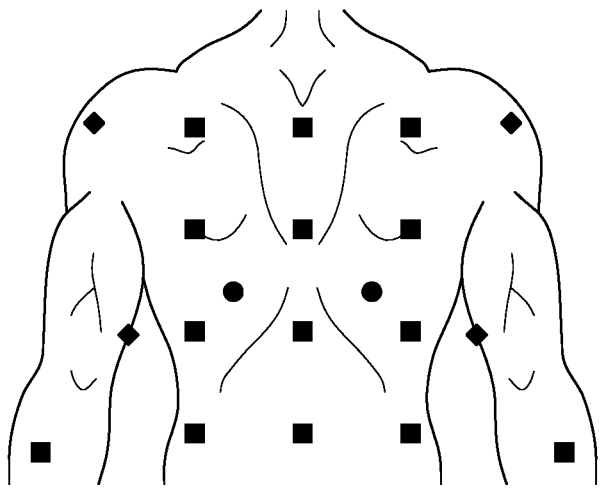

Back of torso with vibration in grid formation over back and centrally located on inside of upper arm between the bicep and triceps, on the shoulder and outside of forearm (lower arm). Most likely placement of Micro Board.

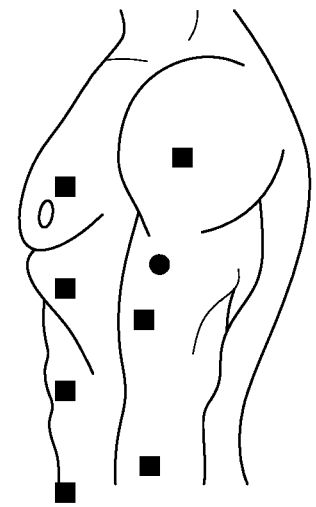

Side torso Left with Vibration at deltoids and centrally located on outside of upper arm between bicep and triceps, abdomen and forearm. Most likely placement of Micro Board

Figure 32

WEARABLE DEVICES, SYSTEMS, METHODS AND ARCHITECTURES FOR SENSORY STIMULATION AND MANIPULATION AND PHYSIOLOGICAL DATA ACQUISITION

FIELD

Embodiments described herein relate to wearable devices, systems, methods and architectures for sensory stimulation and manipulation, and physiological data acquisition. Devices, systems, methods and architectures may be used for stimulating and manipulating the senses and physiological assessment for use in entertainment, medicine, training and education, simulation, virtual reality, research, augmented reality, augmented awareness, and so on.

INTRODUCTION

Electrical Stimulation

Physiological cutaneous Neuromuscular Electrical stimulation (NMES) (also referred to as powered muscle stimulation, functional muscle stimulation, and other terms), Electrical Muscle Stimulation (EMS),Transcutaneous Electrical Nerve Stimulation (TENS), Micro Current Stimulation (MC/FSM), Interferential Stimulation (IFS),Functional Electrical Stimulation (FES) and others are technologies with many different uses. Examples include but are not limited to medical and therapeutic, sports training, cosmetic, and sensory manipulation. Medical and therapeutic uses include but are not limited to: pain relief; prevention or retardation of disuse atrophy; improvement of local blood circulation, exercise of paralyzed muscles; improvement in muscle tone and strength, synchronous neuromuscular brain innervation (muscle re-education). Sports training relates to increased adaptability and outcomes for specific sporting activities as well as recuperation methodologies. Cosmetic refers to muscle toning and weight loss.

Sensory manipulation involves the manipulation of the senses by physical components embodiments described herein (referred to herein as "Sensory Manipulation"). Sensory Manipulation stimulates a person's physiology to sense various, intended and specific sensual outcomes which are associated with the real world but are only being replicated.

These stimulations may be delivered as an intermittent and repeating series of short electrical pulses but can be applied constantly for a delimited duration. Electrical outputs may be delivered transdermally by surface electrodes that are attached to a person's skin. These electrodes may be held to the skin through the use of tapes, bands, belts, straps, bonding agents, adhesives, fasteners or other mechanisms, and may contain an adjoining connector coating composed of gel or other ingredients that is capable of augmenting the efficiency of energy transfer from the electrode to the skin and subcutaneous tissues. Manual application of individual electrodes is a time consuming process that requires a high degree of accuracy and repeatability.

Different forms of currents may be used, for example; interference, diadynamic and iontophoresis. Different devices for wave forms, terminology and resultant stimulation may involve NMES, EMS, TENS, MC/FSM, IFS, and FES. Muscles may efficiently respond to electrical impulses and the frequencies generated by the devices may be important for the stimulation of slow and fast muscle fibres. Equipment used for the devices may be dynamically controlled and adjusted.

Electricity may be used as therapy, including for example NMES, EMS, TENS, MC/FSM, IFS, and FES. For example, Doctors use EMS devices for a variety of reasons. The EMS device may be especially helpful in those who are paralyzed, in pain relief, and improving blood flow in those with poor circulation. Chiropractors also use them on back injuries in order to relax the muscles, which results in faster healing times for patients.

Another example electronic stimulus application is sports. Bodybuilders claim to have received beneficial uses that help them in their weight training. These stimulation devices may also be for use during intense sport training. The devices may provide stimulation that feels comparable to weight training or explosive strength training that is used for those participating in sports that involve fast movements. They also aid in endurance and in the recovery process, post training, which decreases the chances of delayed onset of muscle soreness.

Cosmetic applications relate to helping strengthen and tone one's body. Cosmetic electrotherapy is a range of beauty treatments that uses low electric currents passed through the skin to produce several therapeutic effects such as muscle toning in the body, and micro-lifting of the face. It is based on electrotherapy which has been researched and accepted in the field of rehabilitation. Some of the therapeutic terminology used for these treatments include: Galvanic treatment, NMES or faradic treatment, MENS, High-frequency treatment, and so on.

Sensory Manipulation involves neuromuscular transcutaneous electrical stimulation. Sensory Manipulation occurs when a person's physiology is stimulated to sense various, intended and specific sensual outcomes which are associated with the real world but are being replicated by embodiments described herein. This form of manipulation may be used in such areas as entertainment, augmenting reality, video games, training and simulations (which also include critical incident stress disorder, CISD, and post-traumatic stress disorder, PTSD, rehabilitation programs) and video games.

There are myriad forms of electrical stimulation and varied fields of use. Each electrical stimulation device may be limited to providing a single type of stimulation to the user. In addition, reliability of outcomes may be difficult. Devices may be applied not by medically trained personnel but by home users. Therefore, manual placement of the electrodes may differ during repetitive applications.

Embodiments described herein may provide interoperability between electrical stimulation types, and the fields to which they are applied (e.g. cosmetic: face lift versus Sensory Manipulation: video game). This may include interoperability whereby the patient receives different forms of electrical stimulation concurrently through the same electrodes or simultaneously thorough separate electrodes. Embodiments described herein may provide improvements of efficiency, economy and safety. There exists a need for devices, systems, methods, and architectures for use with different forms of electrical stimulation, or at least alternatives.

Audio

Interactivity with computers and game consoles through input devices was improved further with the introduction of haptics/tactile feedback, which may take the form of vibration feedback. Example forms of feedback for game consoles and mobile game systems, include tactile, visual and audio feedback. Surround sound technology may give a more immersive feel to an audio experience. For example, in a video game, a noise may be emitted in the same direction relative to the player as the noise relative to the player's avatar in the game. Some systems may be created to be implemented in a room, where; only a small portion defined by angles relative to the speakers can accurately include surround sound technology. This area may be referred to the "sweet-spot". Wearable audio devices can personalize the sweet-spot to an individual user, but in the case of headphones or ear buds may be uncomfortable for long usage times, which may be the case for individuals engaging in interactive media simulation activities such as Military, Police, Fire, Hazardous Materials operations, and so on, for driving, flying and technical skill simulations. Furthermore, some devices may place pressure on the ear of those who wear glasses/eyewear causing discomfort. Moreover, they cannot be used with the various head mounted displays ("HMD"). In contrast, a device which allows the user to have force exerted on them does not appear to be available for such use. More specifically, compression stimulation may not be included in some sensory feedback systems. Accordingly, embodiments described herein may provide a device which includes wearable audio technology. In addition, embodiments described herein may provide a device that includes technology that can exert a force onto the user. There exists a need for devices, systems, methods, and architectures for use with different forms of audio technology, or at least alternatives.

Force/Physics

Another example form of feedback is force feedback. This form of feedback is related to physics and corresponds to pushing, pulling and centripetal and centrifugal forces. This form of force feedback can be accomplished with servo-mechanisms, gyroscopes, linear actuators, and so on. A motor or series of motors built into a game controller, which may be directly or indirectly through the use of drive belts or gears are connected to game controllers control,surfaces to actively oppose physical input made by the gamer. This force feedback may require more complex servo-mechanisms and controller design than passive haptic (vibration) feedback does. For example, in a steering wheel controller, force feedback may require a servo mechanism attached to the shaft of the steering wheel. Upon certain electronic commands, for example, in a very high speed turn, the servo-mechanism may act to make the steering wheel physically more difficult to turn. These various types of force feedback may be used for video games. An example type of force feedback includes gyroscopic devices integrated into hand held game controllers and joysticks. There exists a need for devices, systems, methods, and architectures for use with different forms of force feedback technology, or at least alternatives.

Haptic Feedback

Video game controllers may incorporate haptic or tactile feedback. Vibration feedback may be accomplished by linear actuators or providing motors with offset weighting on their shafts to provide a vibration sensation when the shaft is rotated. This might be triggered, for example, to make the controller vibrate when a bomb is dropped; a car crashes; the player is struck by a bullet; etc. Game controller vibration can be tailored to offer specific tactile sensations that express the type or extent of activity occurring in the game.

Video arcade games as well as game consoles were developed and marketed to consumers. Subsequently, there has been growth in interactive multimedia, gaming, simulation training and entertainment industries synchronic with developments in computer science and technology. New developments may involve increased complexity and realism of computer-generated animation and gaming.

With gaming in particular, improvements in three dimensional ("3-D") graphics may allow development of games with more life-like characters, realistic movements, and complex environments. The ultimate goal in some gaming programs and systems may be to enable the virtual characters therein to move and behave within the virtual environment in a natural way that emulates a physical environment as closely as possible, and to provide the user with a virtual environment that more closely simulates the experience of being in the game.

Online games, such as Massive Multiplayer Online games (MMOs), first person shooters, role playing games, racing games, adventure games, etcetera, may give users the ability to interact with multiple players in different locations around the world to enhance the strategy options, interactivity, and realism of the game.

Example interactions include visual elements of the game, two way voice communications between the multiple players partaking within a game, the application of haptics/tactile feedback and force feedback, and so on. This remote real-time interconnectivity may provide virtual simulations and training with individuals from different locations participating together in the same virtual or real training scenario or simulation in real time. Multidirectional haptic feedback and force feedback may further enhance the end-user's entertainment and/or learning experience.

To increase the realism of a computer game further for the user, force feedback may be provided to the user in the form of muscle stimulation. As an alternative to stimulating muscles, devices may stimulate nerves (which in turn stimulate muscles). One such device is a Transcutaneous Electrical Neural Stimulation (TENS) device, and is known for use in medical applications. Force feedback devices may resist miniaturization, because they require physical motors and mechanics. In contrast, by stimulating the wearer's muscles, there may be no need for such mechanical devices which can be cumbersome.

Embodiments described herein may not only provide haptic feedback but force feedback in order to enhance Sensory Manipulation. Embodiments described herein may provide more reliable Sensory Outcomes by involving as many of the senses as possible so as to define Sensory Signatures for the user. Embodiments described herein may provide constriction/compression, temperature, airflow, sound, and so on to the user through the consistency of electrode, vibration, constriction/compression, speaker and other actuator positioning in one or multiple locals on the human body.

Embodiments described herein may provide interoperability between the multitude of stimulating types and the fields, such as video games, movies, health, augmented reality, augmented awareness, in which each or any combination may be used. In addition for the entertainment industry, training and simulation industry, gaming industry, medical and rehabilitation industry and the many implementations related to augmented awareness the embodiments disclosed herein may also provide force and haptic but may additionally include greater environmental sensual impact by allowing the wearer to feel tension, recoil, skin crawling, something brushing against them, being touched, pushed or struck and the like. There exists a need for devices, systems, methods, and architectures for use with different forms of haptic feedback technology, or at least alternatives.

Constriction/Compression

Constriction/compression allows for but is not limited to the applying of pressure. Constriction/compression can apply pressure across an individual at a single location, multiple locations simultaneously or across entire regions of a user's body. The pressure applied can be at varying intensities and can change in intensity over time, as well as being used to create resistance to affect the individual's mobility. Constriction/compression allows for the simulating or support in the simulation of Sensory Signatures (e.g. combinations of Sensory Stimulations), as described herein. Through the use of constriction/compression the Sensory Signatures could include but are not limited to the feeling of something grabbing or holding onto the individual such as a hand; something wrapping around a part of the individual such as a bag over the shoulder; a gradual tightening feeling like a snake wrapping itself around your arm; and wearing heavy equipment and gear that is snug and tight to the body. By using constriction/compression to simulate or support in the simulation of Sensory Signatures it allows for the replication of events that otherwise could not occur.

Constriction/compression may be used in multiple fields. A few examples of its usefulness include medical, training and simulation, entertainment, and augmented awareness. The use for medical can be to provide a form of rehabilitation whereby it gently applies pressure to areas minimizing swelling and stabilizing the injury. The use in training and simulation, and entertainment may be to create a more immersive experience whereby it allows an individual to feel their gear being worn, someone grab them or moving into an obstacle such as a wall, vehicle or another person. A difference may be that, for training and simulation this can be used to create a more realistic experience while entertainment it is used to make a more enjoyable and engaging experience. As for augmented awareness this can be used to inform a user of something they cannot normally detect. In such a circumstance constriction/compression may provide different variations in pressure to the individual at different locations to inform a user of a particular change that they normally would not be aware of (i.e. in a pitch black environment whereby an individual needs to find their way through the constriction/compression may inform the individual that an obstacle is closing in from a particular direction before they even would move into it.). There exists a need for devices, systems, methods, and architectures for use with different forms of constriction/compression technology, or at least alternatives.

Ternperature

An environmental sensual impact to the individual is temperature. In medicine, heat therapy, also called thermotherapy, is the application of heat to the body for pain relief and health. It can take the form of ultrasound, heating pad, cordless FIR heat therapy wrap, and many others. Heat therapy may be used for rehabilitation purposes. The therapeutic effects of heat include increasing the extensibility of collagen tissues; decreasing joint stiffness; reducing pain; relieving muscle spasms; reducing inflammation, and edema. It is useful for myalgia, fibromyalgia, contracture, bursitis and aids in the post-acute phase of healing; and increasing blood flow. The increased blood flow to the affected area provides proteins, nutrients, and oxygen for better healing.

In addition to medical applications, temperature may be an advantageous Sensory Event that would enhance Sensory Manipulation in the realm of entertainment, training and education, simulation, virtual reality, augmented reality and augmented awareness. All of these realms have temperature related environments and impacts. Some movies and video games have settings in warm environments like the heat of Africa. Military training and simulations must be appropriate to the combat environment which is currently focused on the warm desserts of the Mideast. Furthermore temperature is a means to provide feedback to the user and can be combined with other Sensory Stimulations as part of Sensory Events to produce a Sensory Signature and the desired Sensory Outcome. There exists a need for devices, systems, methods, and architectures for use with different forms of temperature technology, or at least alternatives.

Airflow

Air Flow allows for but is not limited to the use of temperature regulation. Temperature regulation can deal with anything from rising, lowering or maintaining an individual's body temperature. Temperature regulation may occur at one or more locations on the body to affect a particular region or could be used to alter the core temperature of the individual. Air Flow may affect an individual in such ways based on the placement of the Air Flow components, the temperature of the air flowing through the system (cool, warm, etc.) and the intensity or pressure at which the air flows through the system. Air Flow may allow for the simulating or support in the simulation of Sensory Signatures. Through the use of Air Flow the Sensory Signatures could include but are not limited to the feeling of a warm, cool or moderate breeze; a burst of air rushing passed as if they are falling from a plane or driving in a car with the window down; and a blast of air from a direction as if something exploded like a grenade. By using Air Flow to simulate or support in the simulation of Sensory Signatures it allows for the replication of events that otherwise could not occur.

Air Flow can be used in multiple fields. A few examples of its usefulness can easily be seen in medical, training and simulation, entertainment, and augmented awareness. The use for medical can be to ensure that an individual's core temperature remains within a particular range to ensure that there body is at its optimal level to help with their current condition. The use in training and simulation, and entertainment may create a more immersive experience whereby it allows an individual to feel wind, hot, cold, blast from an explosion, etc. A difference is that, for training and simulation this can be used to create a more realistic experience while entertainment it is used to make a more enjoyable and engaging experience. As for augmented awareness this can be used to inform a user of something they cannot normally detect. In such a circumstance Air Flow may provide different variations in air pressure or temperature to inform a user of a particular change that they normally would not be aware of (i.e. firefighter within a building is entering an area where carbon monoxide is detected and increasing; they are informed of the issue through the increase in air pressure from the Air Flow devices). There exists a need for devices, systems, methods, and architectures for use with different forms of air flow technology, or at least alternatives.

Physiological Data Acquisition

An example of physiological data acquisition includes the activity of where sensors attached to your body measure key body functions. Data mining, monitoring and the interpreting of these key functions may be useful in medicine, research, training and simulations, and other fields. One area of Physiological Data Acquisition includes Electrodermal Activity (EDA). Electrodermal activity refers to electrical changes measured at the surface of the skin that arise when the skin receives innervating signals from the brain. It is a sensitive index of sympathetic nervous system activity. For most people, if you experience emotional arousal, increased cognitive workload or physical exertion, your brain sends signals to the skin to increase the level of sweating. You may not feel any sweat on the surface of the skin, but the electrical conductance increases in a measurably significant way as the pores begin to fill below the surface. This change in the ability of the skin to conduct electricity, caused by an emotional stimulus such as fright, may be called the Galvanic skin response. This response is measurable and evaluative. Other areas of Physiological data acquisition would include wireless systems such as the BioNomadix physiology monitoring devices for ECG, EEG, EGG, EMG, EOG, Respiration, Temperature, Pulse, EDA, Impedance Cardiography, Gyro, and Accelerometer. There exists a need for devices, systems, methods, and architectures for use with different forms of physiological Data acquisition technology, or at least alternatives.

SUMMARY

In an aspect, embodiments described herein may provide a wearable device comprising a wearable garment and an input module to collect sensory related data. Sensory Devices connect to the wearable garment that actuate to produce Sensory Stimulations, each Sensory Stimulation for inducing physiological stimulation. A Control Centre has a processor for determining Sensory Events, each Sensory Event defining a synergistic action of one or more Sensory Stimulations as a Signal Pathway to produce one or more Sensory Outcomes, each Sensory Outcome for inducing a physiological response or sensory perception, and a transceiver for receiving the sensory related data collected via the input module, and in response, sending an activating signal to actuate one or more Sensor Devices of the plurality of Sensor Devices to activate the Sensory Events.

In another aspect, embodiments described herein may provide interoperable wearable devices which can be used between fields and disciplines, such as electrical stimulation, audio, force feedback, haptic feedback, constriction/compression, temperature, air flow, physiological data acquisition, and so on.

In another aspect, embodiments described herein may provide devices, systems, methods, and architectures that may provide a synergistic action of multiple Sensory Stimulations through audio, EMS, haptic feedback, force feedback, constriction/compression, airflow, temperature, and so on.

In a further aspect, embodiments described herein may provide devices, systems, methods, and architectures that may provide Sensory Stimulation and Sensory Manipulation through activation of Sensory Events. The Sensory Stimulations create Sensory Signatures that may provide intended Sensory Outcome(s), and so on.

In another aspect, embodiments described herein may provide devices, systems, methods, and architectures that may receive immediate physiological feedback data, and implement various Sensory Outcome(s), and so on.

In another aspect, embodiments described herein may provide wearable device comprising: wearable material; an input module to collect sensory related data; electrical stimulus interfaces (electrodes) connected to the wearable material wherein the electrical stimulus interfaces actuate to provide Sensory Manipulation to activate Sensory Events in response to sensory related data collected via the input module to create a variety of Sensory Outcomes.

In accordance with some embodiments, the wearable device may further include a Control Centre having a transceiver which determines the Sensory Manipulation and actuates the electrical stimulus interfaces.

In accordance with some embodiments, the wearable device may further include a Decoder to collect raw data from the input module, the data being sent from an initiating device and transform the data into a format compatible with the Control Centre, wherein the Decoder transmits transformed data via a communications protocol to the Control Centre.

In accordance with some embodiments, the Control Centre translates raw data from the Decoder into Sensory Stimulation(s) for Sensory Manipulations.

In accordance with some embodiments, the Control Centre stores Personalized Settings to determine maximum and minimum sensations for Sensory Manipulations.

In accordance with some embodiments, the input module collects data from sensor devices.

In accordance with some embodiments, the Control Centre is the component of the device which controls the signal, duration, strength, and/or pattern of the electrical stimulus generated causing a Sensory Event, whether singularly, in a Sensory Event Array, random or other formation.

In accordance with some embodiments, the electrodes are removable from the wearable material.

In accordance with some embodiments, the Control Centre is removable from the wearable material.

In accordance with some embodiments, the electrodes are actuators for the force, constriction/compression, vibration and electrical stimulation.

In accordance with some embodiments, the Control Centre selectively identifies which areas of the wearable material are to be activated.

In accordance with some embodiments, the electrodes can deliver multiple variations of stimulation including, but not limited to: Electrical Muscle Stimulation (EMS),Transcutaneous Electrical Nerve Stimulation (TENS), Micro Current Stimulation (MC/FSM), Interferential Stimulation (IFS), Functional Electrical Stimulation (FES) and Neuromuscular Electrical Stimulation (NMES).

In accordance with some embodiments, the Sensory Manipulation(s) provided by the actuated electrodes may occur singularly or in any combination: synchronous, intermittent, consecutive, and imbricate.

In accordance with some embodiments, predetermined and defined electrode placement is based on Sensory Signature(s).

In accordance with some embodiments, positions of the electrodes are user adjustable and the wearable material can optionally have indicators detailing position(s) of electrode(s) to facilitate accurate placement.

In accordance with some embodiments, there may be a set number of allowable locations for the electrodes within the wearable material.

In accordance with some embodiments, positions of the electrodes are predetermined according to neuromuscular and medical indications and recommendation In accordance with some embodiments, the wearable device may further include an audio Decoder to collect audio data from the initiating device, the data being taken from an initiating device and transferring the data via a communications protocol to amplifier/transmitter/receiver.

In accordance with some embodiments, the wearable device may further include speakers to provide Individualized Local Sound.

In accordance with some embodiments, the wearable device may further include amplifier/transmitter/receiver that is operatively connected to the input module (or initiating device) through the audio Decoder to receive, amplify and transmit the incoming data to the speakers.

In accordance with some embodiments, the wearable device may further include vibration actuators.

In accordance with some embodiments, the wearable device may further include force simulation device actuators that may apply physical forces to an individual so that they feel particular sensations that would normally pertain to a particular real world event.

In accordance with some embodiments, the wearable device may further include force simulation device actuators that may apply localized forces.

In accordance with some embodiments, the force simulation device actuators may alter actuated force based on such parameters as the amount of force that is applied (minimal to maximum), the speed at which the force reaches its target amount (fast or slow), the duration to which the force is applied (amount of seconds or deactivates once target force is reached) and the speed at which the force is removed (fast or slow).

In accordance with some embodiments, the wearable device may further include Constriction/Compression Stimulation Device actuators that provide capabilities of applying a compression and/or constrictive feeling to a location of an individual's body.

In accordance with some embodiments, the Constriction/Compression Stimulation Device actuators may alter actuated constriction/compression based on various parameters altered to effect the sensation of constriction/compression and squeezing such as but not limited to the pressure (minimal or a lot), tightening (minimal or a lot), speed that squeezing or constriction/compression occurs or is removed (fast or slow), the length the constriction/compression is activated for (multiple seconds or once fully activated revert to deactivated state) and the ability to fluctuate between these settings while already activated.

In accordance with some embodiments, the wearable material is separated into three garment areas of the body, one being the abdominal area, one being the upper torso or chest and shoulder area, and one representing coverage of both the abdominal and torso area figures, wherein all components may be interconnected to provide synergy and totality of Sensory Manipulation throughout the entire garment as defined by a Signal Pathway to create the Sensory Signatures which produce a desired Sensory Outcome.

In a further aspect, embodiments described herein may provide a wearable device comprising wearable material, electrodes, a Medically Compliant Electrical Impulse Amplifier Transmitter Receiver (MCEIATR), and a control center, wherein the control center actuates the MCEIATR which in turn provides the stimulus through the electrodes positioned on the wearable material.

Additional example embodiments are described herein.

BRIEF DESCRIPTION OF THE DRAWINGS

The embodiments will now be described by way of example only, with reference to the accompanying drawings, in which:

FIG. 3 is a schematic representation of a garment;

FIG. 3a is a schematic representation of a garment with a plurality of electrodes and showing all electrodes activated, where the electrodes are wired directly to the MCEIATR;

FIG. 3b is a schematic representation similar to that shown in FIG. 3a but showing some of the electrodes activated, where the electrodes may not be wired and may utilize a conductive garment whereby the MCEIATR is connected to the conductive garment and the electrodes are connected to the conductive garment. These are garments that may be wireless taking the charge through the garment and sending it to the electrode. In another embodiment the garment may be made of specific materials that do not require electrodes. These garments may plug directly into the MCEIATR. In the embodiments denoted by FIGS. 3b and 3c "conductive garments" may be used to transfer the electrical charge to and from the electrodes.

FIG. 3c is a schematic representation similar to that shown in FIGS. 3a and 3b but showing none of the electrodes activated;

FIG. 5a is a schematic representation of the interior of the first layer of the garment of an embodiment;

FIG. 5b is a schematic representation of the interior and/or exterior of the second layer of the garment of an embodiment and includes the placement of the Control Centre and power regulator on the exterior of the second layer of the garment;

FIG. 5c is a schematic representation of the third layer of the garment of the embodiment;

FIG. 13b is a schematic representation of a side view of the embodiment shown in FIG. 13a; and also like FIG. 13a this view of an example embodiment is meant to be seen as if the garment were see through.

FIG. 13c is a schematic representation of a frontal view of an embodiment which includes the entire body; the entire torso including the arms and waist, the lower body including the hips, upper and lower legs. Also like FIG. 13a this view of an example embodiment is meant to be seen as if the garment were see through.

FIG. 18 illustrates nervous system specifications for power activation according to some embodiments.

FIGS. 20a through 20d illustrates nervous system specifications for surround sound according to some embodiments.

FIG. 24 illustrates example nervous system STIMS specifications. The STIMS includes MCEIAs and paired electrodes.

FIGS. 25 to 37 illustrate sensory device placement for example embodiments.

DETAILED DESCRIPTION OF VARIOUS EMBODIMENTS

Figure 2:
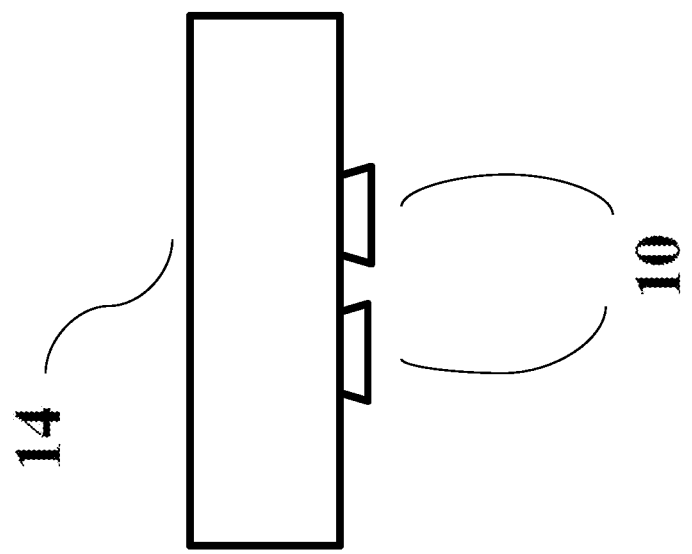
FIG. 2 is a schematic representation of a pair of predetermined and defined electrodes within a garment.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the various programmable computers may be a server, network appliance, set-top box, embedded device, computer expansion module, personal computer, laptop, personal data assistant, cellular telephone, smartphone device, UMPC tablets and wireless hypermedia device or any other computing device capable of being configured to carry out the methods described herein.

Program code is applied to input data to perform the functions described herein and to generate output information. The output information is applied to one or more output devices, in known fashion. In some embodiments, the communication interface may be a network communication interface. In embodiments in which elements of the invention are combined, the communication interface may be a software communication interface, such as those for inter-process communication. In still other embodiments, there may be a combination of communication interfaces implemented as hardware, software, and combination thereof.

Each program may be implemented in a high level procedural or object oriented programming or scripting language, or a combination thereof, to communicate with a computer system. However, alternatively the programs may be implemented in assembly or machine language, if desired. The language may be a compiled or interpreted language. Each such computer program may be stored on a storage media or a device (e.g., ROM, magnetic disk, optical disc), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the systems and methods of the described embodiments are capable of being distributed in a computer program product including a physical, non-transitory computer readable medium that bears computer usable instructions for one or more processors. The medium may be provided in various forms, including one or more diskettes, compact disks, tapes, chips, magnetic and electronic storage media, volatile memory, non-volatile memory and the like. Non-transitory computer-readable media may include all computer-readable media, with the exception being a transitory, propagating signal. The term non-transitory is not intended to exclude computer readable media such as primary memory, volatile memory, RAM and so on, where the data stored thereon may only be temporarily stored. The computer useable instructions may also be in various forms, including compiled and non-compiled code.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. One should appreciate that the systems and methods described herein may provide various technical effects. For example, embodiments may include tangible actuate electrical stimulus interfaces (electrodes) to provide tangible stimulation in response to activated Sensory Events. The activations or actuations of specific Sensory Devices of the Nervous System may translate into tangible Sensory Stimulation to provide physiological stimulation for the user. As an example, a Force Simulation Device may apply physical forces to an individual so that they feel particular sensations that would normally pertain to a particular real world event. Sensory Stimulations include audio, vibration, electrical stimulation, force/physics, constriction/compression, and so on. A Force Simulation Device may allow for virtual mediums to have an increased immersive experience as a force applied to the body will give the intensity of the force applied and the direction to which the force came from based on its location in the garment. Sensory related data may be collected in raw data form and transformed by hardware components into data representative of different sensory experiences and stimulations, as described herein. Other example technical effects are described herein.

The following discussion provides many example embodiments. Although each embodiment represents a single combination of inventive elements, other embodiments may represent all possible combinations of the disclosed elements. Thus if one embodiment comprises elements A, B, and C, and a second embodiment comprises elements B and D, then other embodiments may include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Various terms and definitions used herein will be described herein to enhance clarity and facilitate illustration of various example embodiments. These are example descriptions for illustrations.

Computing Devices may be used herein to relate to an electronic device that sends and/or receives data to initiate and/or activate the particular componentry that we discuss in this patent. Such as, but not limited to, any form of computer. Computing Devices may be operable by users to access functionality of embodiments described herein. Computing Devices may be the same or different types of devices. Computing Devices may be implemented using one or more processors and one or more data storage devices configured with database(s) or file system(s), or using multiple devices or groups of storage devices distributed over a wide geographic area and connected via a network (which may be referred to as "cloud computing"). Computing Devices may reside on any networked computing device, such as a personal computer, workstation, server, portable computer, mobile device, personal digital assistant, laptop, tablet, smart phone, WAP phone, an interactive television, video display terminals, gaming consoles, electronic reading device, and portable electronic devices or a combination of these. Computing Devices may include any type of processor, such as, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. Computing Devices may include any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Computing Devices may include one or more input devices, such as a keyboard, mouse, camera, touch screen and a microphone, and may also include one or more output devices such as a display screen and a speaker. Computing Devices may have a network interface in order to communicate with other components, to access and connect to network resources, to serve an application and other applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. There may be more Computing Devices distributed over a geographic area and connected via a network. Computing Devices is operable to register and authenticate users (using a login, unique identifier, and password for example) prior to providing access to applications, a local network, network resources, other networks and network security devices. Computing Devices may be different types of devices and may serve one user or multiple users.

Interoperability may be used herein to refer to the ability of wearable technologies in accordance with embodiments described herein to be utilized across fields and disciplines to work with other systems without special effort on the part of the customer.

Medically Compliant Electrical Impulse Amplifier Transmitter Receive (MCEIATR) may be used herein to relate to a computing device that is intended to provide stimulation to the physiology through the application of electrical energy to the physiology; to receive data from the physiology; and to transmit data wirelessly. This may be a device that is medically compliant in its activation protocol and limitations as well as adheres to the US FDA standards for such devices and which includes over the counter and prescription units. These devices emit an electrical pulse that may be transferred through electrodes and or conductive fabric and transcutaneously through the wearer's physiology attaining the designated results. Furthermore, these devices may receive data through electrodes and or conductive fabric acquiring physiological information of the wearer. The MCEIATR may be defined in the garment or can be external.

Operably Connected may be used herein to refer to any components that are directly or indirectly connected or coupled. Any form of connection that allows for communication between the components is allowable. This includes but is not limited to; wired connections, wireless, Wi-Fi, WLAN (wireless local area network), radio, near-field communication, or Bluetooth connections or a combination thereof.

Nervous System may be used herein to refer to all the componentry that is attached or connected to the Control Center that works to provide or produce Sensory Stimulation(s) to the wearer and more specifically can refer to the Sensory Devices and their integration as a whole.

Sensory Device (SD) may be used herein to refer to any contrivance, such as an ultrasonic pad or electrode, that receives and or responds to data, a signal or stimulus and translates or transfers this input into a form of energy that acts on one or more of the faculties by which the body perceives an external stimulus; one of the faculties of sight, smell, hearing, taste, and touch. Sensory Device actuates to produce Sensory Stimulations to act on the body faculties as physiological stimuli.

Sensory Stimulation may be used herein to refer to the activation of one or more of the body's faculties of sight, smell, hearing, taste, and touch through the actuation of one or more Sensory Devices. Different types of Sensory Stimulation may produce different types of physiological stimulation.

Sensory Manipulation may be used herein to refer to the use of a Sensory Device(s) to provide Sensory Stimulation(s) for a specific purpose or outcome. Sensory Devices may actuate to produce Sensory Manipulations as one or more Sensory Stimulations.

Sensory Event may be used herein to relate to any single or simultaneous Sensory Device (SD) activation which produces Sensory Stimulations or Sensory Manipulation. In addition, Sensory Event refers to the synergistic action of multiple Sensory Stimulations of different types such as through audio, EMS, haptic feedback, force feedback, constriction/compression, airflow, temperature and so on to produce a desired Sensory Signature and/or Sensory Outcome. A Sensory Event may contain one or more simultaneous Sensory Stimulation activations as a Sensory Manipulation. A Sensory Event occurs when a computing device or Control Centre sends an activating signal to one or more Sensory Devices actuators which produce Sensory Stimulations and stimulates the user's physiology. More than one type of Sensory Device may be actuated during a Sensory Event. More than one type of Sensory Stimulation may be produced during a Sensory Event. A Signal Path may define a Sensory Event to indicate a set of Sensory Devices to actuate and a set of Sensory Stimulations to produce using the actuated Sensory Devices. A Sensory Event may involve simultaneously or sequential actuation of Sensory Devices to produce different patterns of Sensory Stimulations, as a Sensory Signature or Sensory Outcome.

Sensory Event Array may be used herein to refer to the dispersal pattern of Sensory Stimulation through the combination of simultaneous and or sequential Sensory Event activations and Sensory Device actuations.

Sensory Signature may be used herein to refer to sensory information outputs that a particular object manifests to be recognizable and perceived through the user's senses. This may be enhanced by situational awareness (such as knowing what type of environment they are in, such as for example Realistic Military Simulation or Sci-Fi world). A Sensory Signature may be produced through the application of specific Sensory Events which provide intended Sensory Manipulation (e.g. Sensory Stimulations by actuation of Sensory Devices) to produce the reality within the user's mind as portrayed in the virtual world. It is the specific and reproducible induced physiological response outcome (e.g. Sensory Outcome) of the user created through Sensory Manipulation. It may be achieved utilizing a specific and defined set of Sensory Stimulations and Sensory Device activations as defined in the specified Sensory Event.

Sensory Outcome may be used herein to refer to the user's physiological response to a Sensory Event or Sensory Signature(s) applied.

The integration of technology with everyday life through the integration of clothing, garments, fashions, accessories or anything worn by a person with one or more computing devices and/or advanced electronic technologies may be provided in various aspects by embodiments described herein. Specifically, the embodiments described herein may provide various garments, such as clothing and accessories, that incorporate computers and advanced electronic technologies. Other wearable technology or devices may also be provided and these are illustrative examples. The term wearable technology extends to anything worn that could have the integration of computers and advanced electronics to improve upon the usefulness of what is being worn. This may extend from clothing that may be worn for fashion to uniforms and clothing meant for work to clothing, body armour and exoskeletons designed for protective purposes or a particular task. These items that an individual can wear will hereinafter be called garments and garments are, but are not limited to, various forms of shirts, hats, vests, coats, gloves, footwear, pants, shorts, and masks; whether they are of light, dense, soft, hard, malleable or rigid fibres, materials or composites. Thus, the integration of technology into any of the above mentioned garments may provide an improvement upon that particular garment if the technology was designed to be used appropriately with it. The foregoing list of garments described is illustrative only and is not intended to be limiting in any way.

Embodiment described herein may incorporate several forms of stimuli (e.g. Sensory Stimulations) and apply them over various distinct fields of practice such as, but not limited to: augmented awareness, entertainment, recreation, training and simulation, medical rehabilitation, and so on. Thus, augmented awareness may refer to any situation where greater awareness of the environment is warranted, needed or wanted, such as providing feedback for the blind to walk and move around reducing tripping and falling and providing GPS directional cues or for the deaf to be alerted to oncoming vehicles, or for a roofer to be warned when they are too close to the edge of the precipice, etcetera. Entertainment includes but is not limited to video games, movies (home televisions or theatre) and music and augmented reality. Recreation includes any activity done for enjoyment when one is not working (massaging, for example). Training/simulation includes but is not limited to the military, police, fire, tactical training and education research. Medical rehabilitation refers to the use of improving the speed at which an individual recovers from particular physiological or psychological problems and physiotherapeutic or psychotherapeutic activities and uses. The types of stimuli include, but are not limited to; electrical stimulation, audio stimulation and the application of forces to the individual.

WPEST allows individuals using a MCEIATR and/or interacting with a virtual medium or other device to receive tissue, nerve and/or muscle stimulation and/or contraction so that the stimulation is precise as determined by its ability to conform to the scientific methodology of repeatability, reproducibility and reliability; this being due to consistency of electrode positioning in one or multiple locals on a wearable garment that correspond to locals on the human body when worn. The wearable garment includes different types of Sensor Devices that actuate to provide different types of Sensory Stimulation. As an example, electrical stimulation (as an example of Sensory Stimulation) provided by electrodes (as an example of Sensory Devices) may be of any form of stimulation including but not limited to EMS, TENS, MC/FSM, IFS, FES, and NMES). The interaction device can be any form of computing device.

The apparatus can also further include Sensory Devices for Individualized Local Sound which is a way for speakers/subwoofers/audio output devices (hereinafter referred to as a speaker) to be implemented to give an individual highly accurate directional sound relative to an individual's placement in regards to a particular application without worrying about the constraints of the physical environment, the individual's physical location in an environment or other individuals in the physical environment.

Additionally, the Sensory Device may include a Force Simulating Device, which is a mechanical componentry within garments to simulate the effects of forces on the body. The componentry is designed to be controlled via a computing device (or Control Centre) that sends data to the Force Simulation Device to determine what forces to apply to the individual. The computing device sends activating signals to actuate the Force Simulation Device to produce Sensory Stimulations as force stimulation. These forces are to give an individual the sensation of motion whether it be a push, pull, twist, tension, compression or constriction applied in a particular direction or the feeling of centripetal or centrifugal force. Through these sensations or physiological stimulations it allows an individual to feel particular forces that may be in effect. The hardware does not need to be associated with a particular medium as it can work with a variety of types of computing devices that have the ability to send data to the device that would activate its mechanical componentry to create one of its various effects. Further to this, a Sensory Device may also include Constriction/Compression Stimulation Device which may have the ability to apply local, general, or total hugging, squeezing, contracting, tightening, or crushing to the individual using embodiments described herein.

Figure 1:
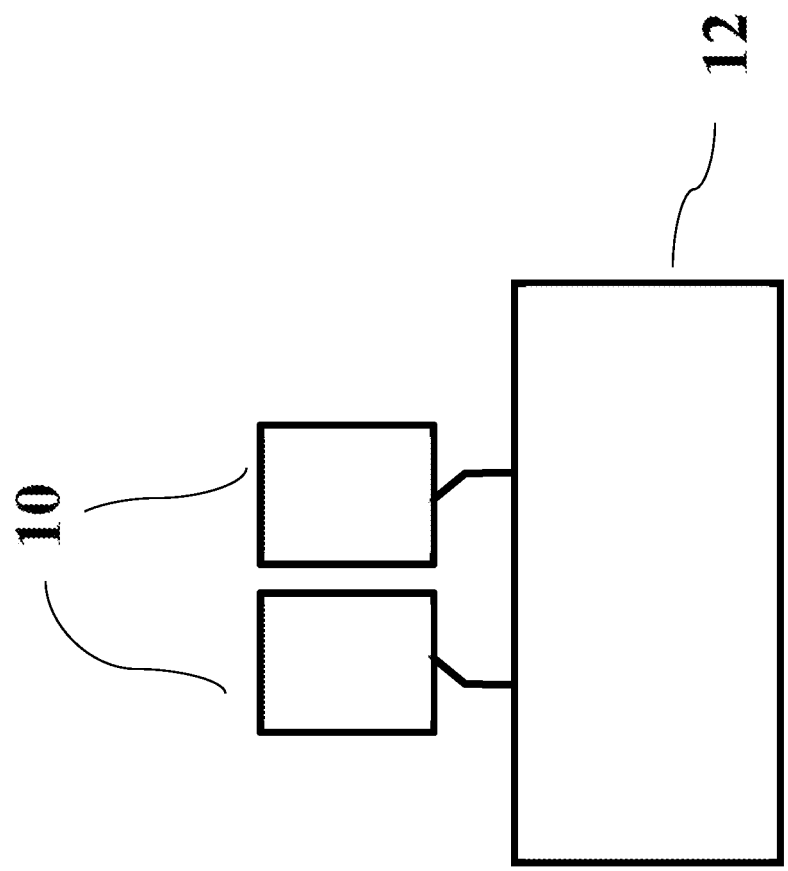
FIG. 1 is a schematic representation of the connection between the MCEIATR and a pair of electrodes.

FIG. 1 shows electrodes 10 and an MCEIATR 12 which are operably connected. In the embodiment shown, the two are hardwired together, but they may be coupled using various wired and wireless technologies. FIG. 2 depicts the application of the electrical stimulus interfaces (electrodes) 10 via a wearable material 14 which are predetermined and definite within said garment 14. The electrodes 10 are an example Sensory Device. The electrodes 10 can deliver multiple variations of Sensory Stimulation including, but not limited to: EMS, TENS, MC/FSM, IFS, FES, and NMES. This stimulation and/or the variations thereof also can be applied and/or delivered simultaneously, consecutively or intermittently.

FIG. 3 illustrates wearable material 14. FIGS. 3a, 3b and 3c depict different examples of electrode 10 stimulation on wearable material 14, and how the MCEIATR 12 can select which electrodes 10 are to be stimulated and which are not. A Signal Path of a Sensory Event may define which electrodes are to be stimulated (to produce Sensory Stimulations) and which are not. Electrode placement is for illustrative purposes and may or may not be positioned as shown. FIG. 3a shows all electrodes 10 being actuated via a wired connection 18 to produce Sensory Stimulations. FIG. 3b shows some electrodes 10 being actuated to produce Sensory Stimulations. FIG. 3c shows no electrodes 10 actuated to produce Sensory Stimulations. The embodiments also provide reliability through predetermined and defined electrode 10 placement which may correspond to different physiological locations. As electrode 10 positioning relates to type and the frequency of stimulation (to produce different Sensory Stimulations) for activated Sensory Events and the ensuing physiological response and the sensory perception from this response (Sensory Signature or Sensory Outcome), it is imperative that for the same sensory simulated response (Sensory Signature or Sensory Outcome) to occur and that the process is repeatable, consistently reproducible and reliable. Repetition refers to the ability to repeat the same action or activity with no change in the setup or configuration. In some embodiments, the positions of the electrodes 10 are user adjustable and the wearable material 14 can optionally have indicators detailing the position of electrode 10 to allow an individual to accurately repeat the placement. Alternatively, an embodiment could have a set number of allowable locations for the electrodes 10 within the wearable garment 14. Accordingly, to be repeatable the electrodes 10 may be positioned similarly each time so that they will provide the same Sensory Manipulation or Sensory Stimulation. The electrodes 10 are predetermined and defined and they then maintain this positioning in the garment 14. Predetermined and defined refers to the permanent or non-permanent placement of electrodes 10 on the garment 14 which maintain their position relative the garment 14 unless, in the case of non-permanent, otherwise moved by an individual or removed for replacement due to wear.

The garment 14 houses the Control Centre 16. The Control Centre 16 is a computing device which may contain a Mem Chip, profile selector, transceiver, USB port, actuation module, and sensory software. Control Centre 16 is the signal processor actuation and communications interface 16 (as detailed in FIG. 14). In some embodiments, the Transceiver may be integrated into the garment (Exoskeleton of ARAIG) while the Mem Chip may be detachable from the Transceiver. For the Control Centre 16 to work it may not require a Mem Chip to be attached to the Transceiver. The Control Centre 16 determines the exact Sensory Manipulation that occurs by defining different Sensory Events as Signal Paths for actuation of the Sensor Devices in different ways. A Signal Path may define different combinations or sets of Sensor Devices to actuate for Sensory Events and parameters of the Signal Path may define different types of Sensory Manipulations produced by the actuated Sensory Devices.

The Transceiver is the component of the Control Centre 16 that activates the necessary Sensory Devices by transmitting activation signals to the Sensory Devices. The Sensory Devices (e.g. electrodes 10) make up the components of ARAIG's Nervous System. This activation is based on the translated sensory data from the Decoder 56 and the stored user settings of the attached Mem Chip. The Control Centre 16 determines Sensory Events using the sensory data and the user settings. The data received from the Decoder 56 is the raw data to determine what Sensory Devices of the Nervous System should be activated and the Sensory Stimulation(s) that they will produce, as stipulated in the determined Sensory Events. The settings taken from the Mem Chip allow the Transceiver to alter the raw data from the Decoder 56 to select Sensory Events that activate to actuate Sensory Devices to produce Sensory Stimulation(s) that are within acceptable ranges of the Mem Chip's Personalized Settings. Therefore, the Transceiver receives the data from the Decoder 56, alters the data as required by the Mem Chip's Personalized Settings and then activates the appropriate Nervous System component(s) Sensory Device(s), to provide the correct Sensory Signature(s) or Sensory Stimulations for the Sensory Events. If there is no Mem Chip attached to the Control Centre 16 then the Transceiver may use the raw data from the Decoder 56 to activate the Nervous System.

The Mem Chip is the component of the Control Centre 16 that stores the user's Personalized Settings to determine the maximum and minimum sensations of the Nervous System's components. The Personalized Settings may also define one or more Sensory Events which may be customized for a user or situation. The default setting of the Mem Chip may allow all the components, of the Nervous System to be activated to maximum capabilities. To alter the default setting of the Mem Chip the user may run ARAIG's Calibration and Diagnostics Protocol (e.g. video game). With the Mem Chip settings updated and stored for any further use the components of the Nervous System may now be set to the Personalized Settings of the user rather than the default settings. In one embodiment, if they use the Calibration and Diagnostics Protocol more than once, the "final use" may create another profile on the Mem Chip and will set this as the new active Personal Settings. In another embodiment the user may choose to store this "final use" profile as a secondary or other profile in their number of saved user profiles.

Since the Mem Chip may not deal directly with the data sent from a wearable device and only alters the translated data, the Mem Chip's Personalized Settings may be universal for all devices. This allows a user the ability of setting their Personalized Settings on one wearable device and using them on any wearable device. This ensures that the user only has to update their Personalized Settings when they want something changed and not when something has changed on them.

The design of the Mem Chip may be that of a USB or other type of device to be detachable so that it can be attached to a wearable device or another ARAIG. The purpose for attaching directly to another device is to update the Mem Chip should any alterations, patches, or mods be required or wanted and the ability to store their Personalized Settings externally. The use of externally storing their Personalized Settings also allows for the user to share their Personalized Settings with others and have multiple Personalized Settings at their disposal. As for attaching to a different ARAIG, this protocol may allow an easy transfer of all of their preferences without having to go through any previous setup. This transfer of one Mem Chip to another ARAIG will be possible for ARAIG's of the same generation but it may not be possible for different generations as they may be more complex and their Mem Chip software could be different to match the changes. Meaning, upon purchase of a new ARAIG of a different generation they may need to go through a Calibration and Diagnostics Protocol for that generation of ARAIG.

The Nervous System may be the portion of ARAIG that contains the immersive qualities, the Sensory Events defining different Sensory Stimulations and Sensory Manipulations, as well as the Physiological Data Acquisition capabilities and may be the interactive portion of the product. The Nervous System may be attached to the Exoskeleton and its sensory components (e.g. Sensory Devices) may be activated by the Control Centre 16 through activation signals. The activations of specific Sensory Devices of the Nervous System may translate into tangible Sensory Stimulation to the user.

The Control Centre 16 is the device that will actuate the MCEIATR 12 which in turn provides the stimulus through the electrodes 10 or other Sensory Devices. The garment 14 is applied or fitted into position onto the user. The electrodes 10 may be already predetermined to affix to the skin of the user in the desired anatomic location in some embodiments. In some embodiments the electrodes may be prepositioned and permanently affixed within the garment. Each time the garment 14 is fitted onto the user the configuration of electrodes 10 may remain fixed, unless changed by the user, thereby stimulating the exact anatomical elements as previous or providing the same Sensory Stimulations as previous. This repetition may be performed until such time as the electrodes 10 need to be replaced. The new electrodes 10 may take the exact same position on the garment 14 as those being replaced thus allowing for the unlimited repetition of this activity which allows for consistency in the reproduction of the desired Sensory Signature or Sensory Event over a period of time. Reproducibility is the ability of the entire process or action to be reproduced, either by the user, producer, director, initiator, or by someone else working independently. The embodiments described herein provide this reproducibility and subsequent reliability. The embodiments described herein provides a new and inventive methodology, system, and architecture for the provision of this repetition, reproducibility, and reliability which makes the outcomes precise as desired by the user, producer, director and/or initiator of the prescribed stimulus for many applications.

A minimum of two electrodes 10 may be used for some embodiments, but in other embodiments, an array of electrodes 10 may be attached to the garment 14 to give accurate localized stimulation.

WPEST has the ability to provide and produce more than one type of stimulation which may include but is not be limited to EMS, TENS, MC/FSM, IFS, FES, and NMES. A Sensory Event may define different types of Sensory Stimulation to produce different Sensory Outcomes. These varying Sensory Stimulations may occur singularly or in any combination: synchronous, intermittent, consecutive, imbricate, etc. The pattern and configuration for the Sensory Stimulations may be defined by a Signal Path of a Sensory Event to produce desired Sensory Outcomes.

This singular or multiple stimulation(s) may occur on or over one or more sets of electrodes 10. The Sensory Event may define different sets of Sensory Devices for actuation at activation of the Sensory Event. For example, a wearer can receive TENS applications to the shoulder while simultaneously receiving EMS applications to the lower back.

Embodiments described herein may also provide and produce more than one type of Sensory Stimulation on the same plurality of electrodes 10. For example, a wearer can receive an FES application to their right shoulder which is consecutively followed by a TENS application through the same electrodes 10 to that same right shoulder.

Figure 4A:
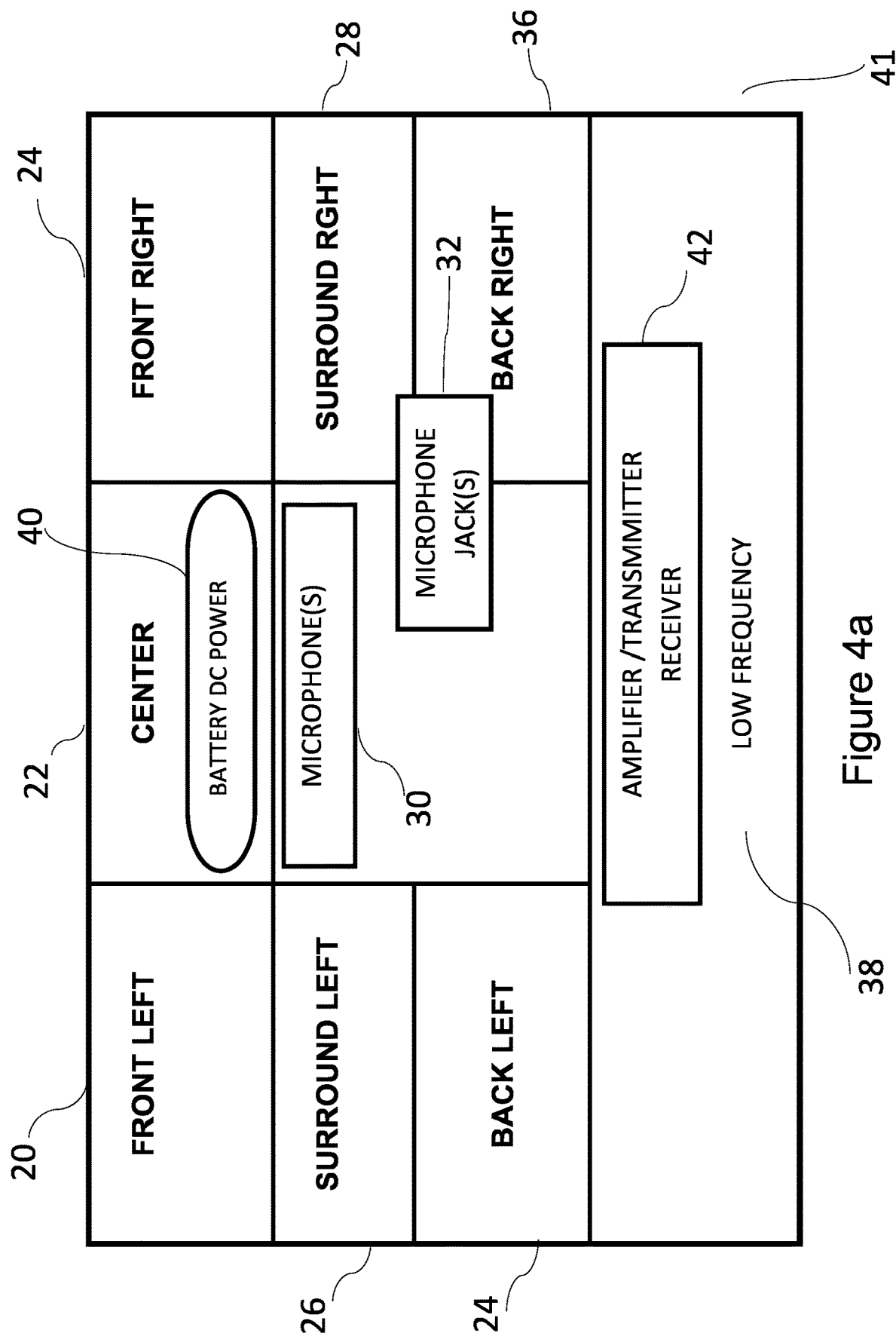
FIG. 4a is a schematic representation of an audio architecture relative the user.
Figure 4B:
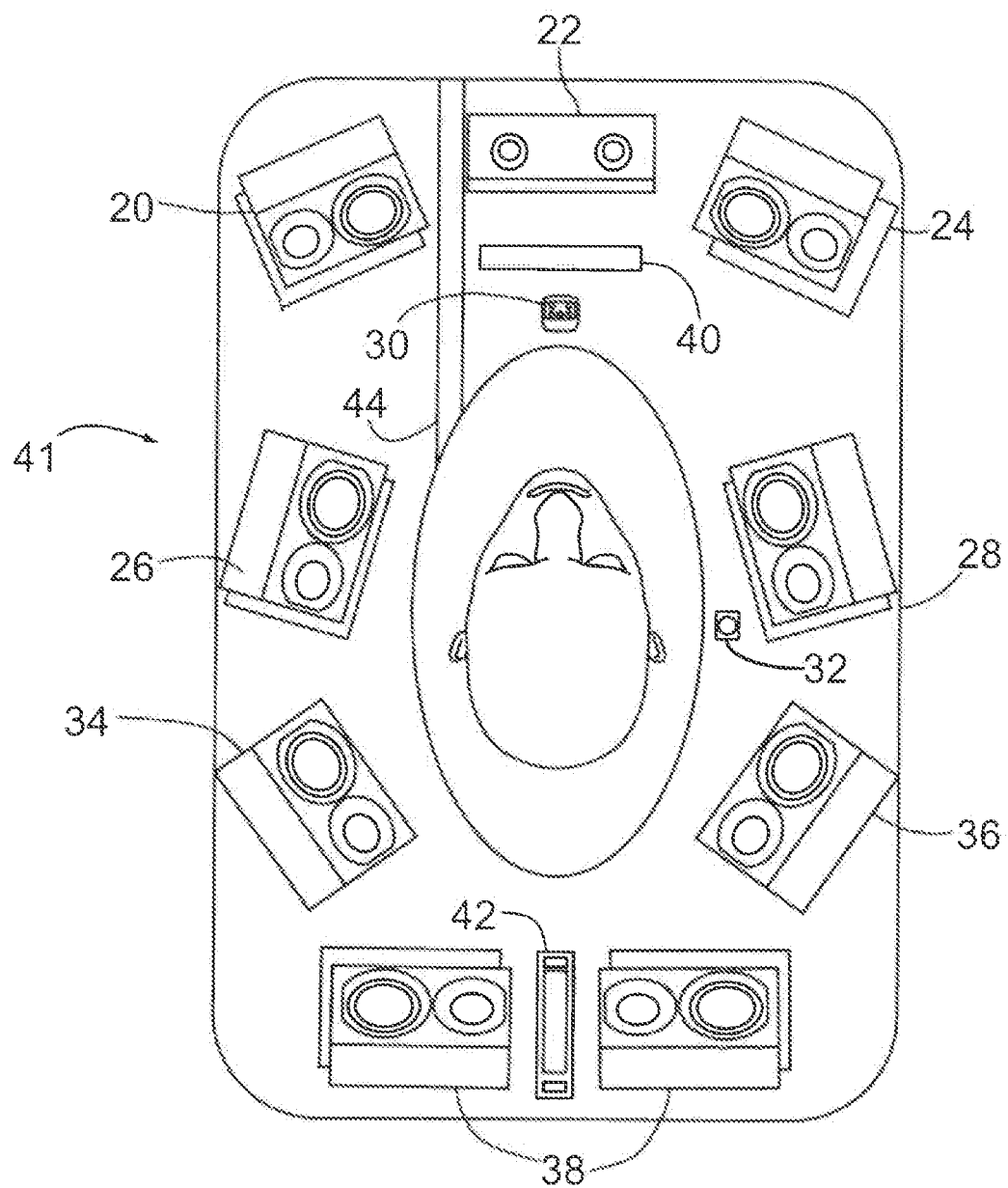
FIG. 4b is a schematic representation of an embodiment with a plurality of speakers surrounding the user.

FIGS. 4a, 4b, 4c and 4d show the incorporation of speakers into the garment 14 as another example of Sensory Devices that produce audio physiological stimulations as Sensory Stimulations. As depicted, the embodiment of individualized surround sound 41 has front left speaker 20, center speaker 22, front right speaker 24, surround left speaker 26, surround right speaker 28, back left speaker 34, back right speaker 36 and low frequency subwoofer speakers 38. Additionally, the suit allows the user audio input via a microphone 30 or the use of an external microphone which can be plugged into microphone jack 32. The device is powered by its power source 40 which may be secondary to the power source provided to the Control Center 16 and myriad Sensory Devices. The power source can be anything that effectively supplies power to the device, including, but not limited to; batteries, a cable plugged into an outlet, or another device that supplies AC, DC or a combination thereof. FIG. 4b additionally depicts an amplifier/transmitter/receiver 42 that is operatively connected to the initiating device or an Audio Decoder 42a and receives, amplifies and transmits the incoming data to the speakers. The embodiment shown in FIG. 4b also has an opening area 44 which can be opened and closed for donning and removing the device. Possible non-permanent closing methods include; hook and loop type fasteners, zippers, snaps, buttons, and etcetera.

Figure 14:
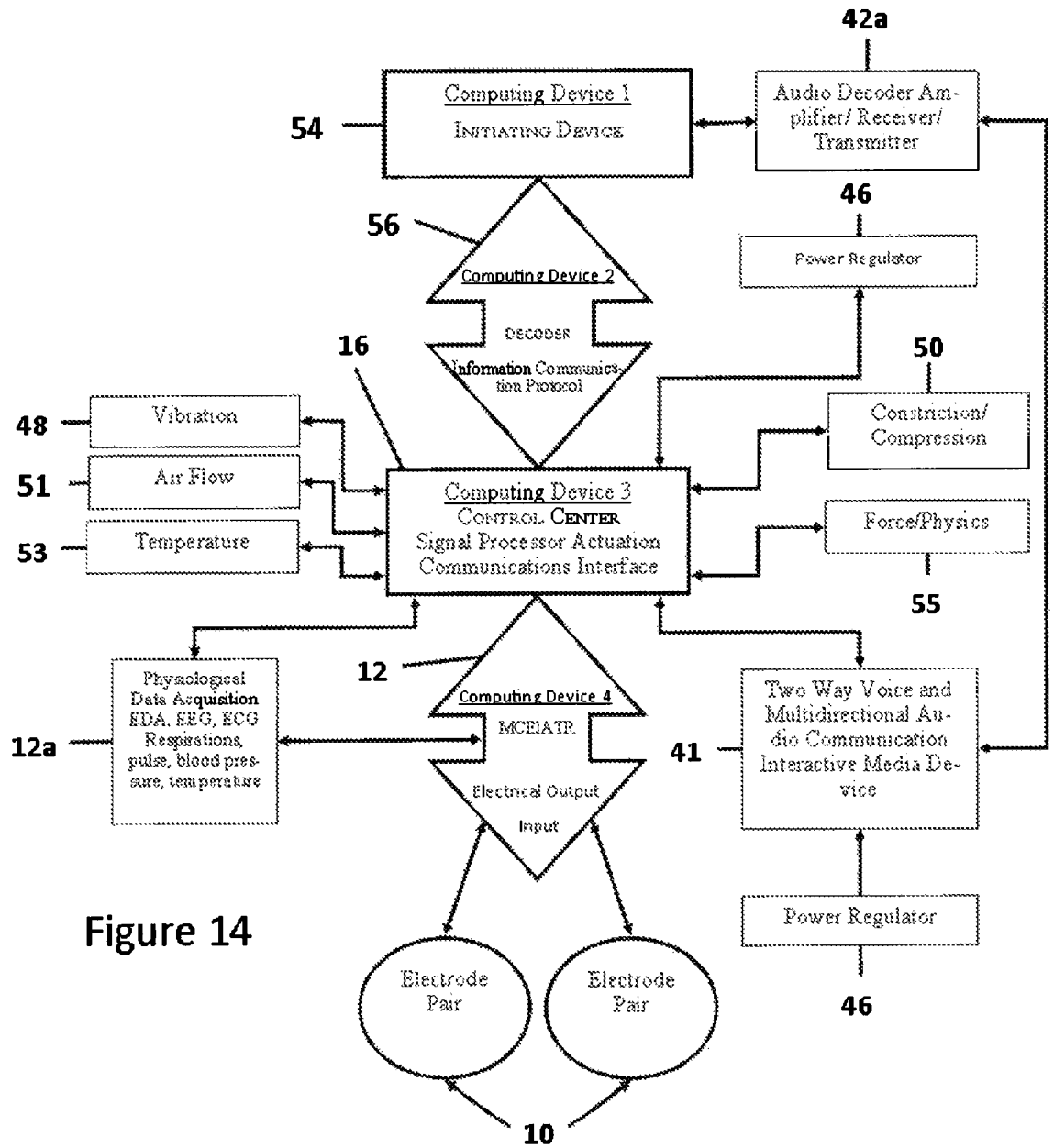
FIG. 14 is a schematic representation of the signal pathway from the initiating device to actuator and from the actuator to the initiating device.

In another embodiment a second amplifier/transmitter/receiver the Audio Decoder 42a as shown in FIG. 14 may be utilized which takes the information directly from the initiating device 54 and transmits it to the amplifier/transmitter/receiver 42 affixed to the garment 14. The communications and wireless communications protocol for the Audio Decoder may be one or more of, but is in no way limited to HDMI, Wifi, Radio, Bluetooth.

The use of the Individualized Local Sound can be used with any form of computing device. Individualized Local Sound can be used for computing devices implementing virtual mediums and many real world situations. The efficiency of the sound system designed in this manner is that the speakers maintain their position around the wearer; ensuring that the wearer is always in the optimal position, "sweet spot", for surround sound. Unlike traditional sound systems which are placed at particular locations in an environment or headphones which are placed to rest on the head and have the speakers located on or in the outer portion of the ear, Individualized Local Sound is a form of Wearable Technology. Individualized Local Sound is the integration of speakers into the garment 14 worn by the individual at different positions. In another embodiment, the most relevant to the auditory system are but are not limited to those that cover the torso, upper arms and head as these are located near the ears and would have the least amount of change in location in relation to the ear; while the lower arms and legs which could be in motion or at various angles that would make speaker placement much more difficult. Therefore it may be easier to integrate speakers in the previously mentioned locations and would be the major area of interest for Individualized Local Sound.

By integrating a single speaker into a garment 14 it allows the speaker to be placed in a particular location that will remain located in the same position relative to the individual using the speaker. This allows for a single speaker to represent a particular direction sounds are emanating from while still having all of the original functionality that a speaker would permit such as volume, bass, and son, operably connected to a computing device. In addition, Individualized Local Sound can then be extended by integrating multiple speakers into a garment 14. By integrating more speakers it may allow an individual to receive sound that has accurate multidirectional feedback, is relative to their location and individualized to them rather than designed for the environment. The Control Centre may implement sound stimulation by selectively choosing volume levels in individual speakers of the sound system. This may allow for example a car to actually sound like it is moving passed the individual, or when someone is talking to the individual this other individual could be heard via the speakers that represent the direction they are located; will increase the auditory awareness, reaction time and overall immersive experience.

In some embodiments, the material that provides the housing for the sound system may be of a sound absorbing nature. The speakers themselves may be angled in such a way as to provide the auditory cone (sound cones) to be directed to affect the best possible auditory experience and/orient the sound at the user. This means a plurality of users may use the individualized surround sound and minimally disrupt each other.

Figure 4C:
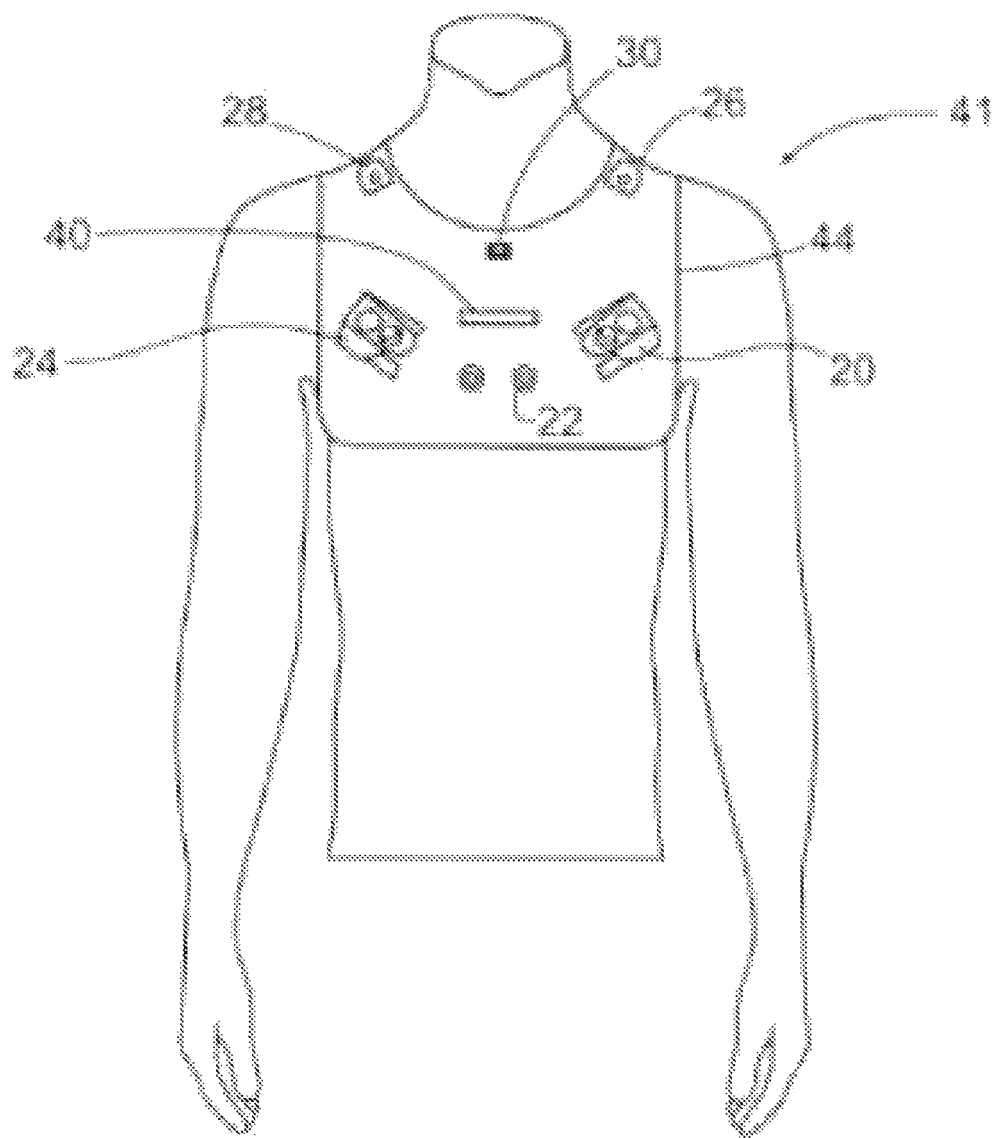
FIG. 4c is a schematic representation of the front of the user with the embodiment of 4b.
Figure 4D:
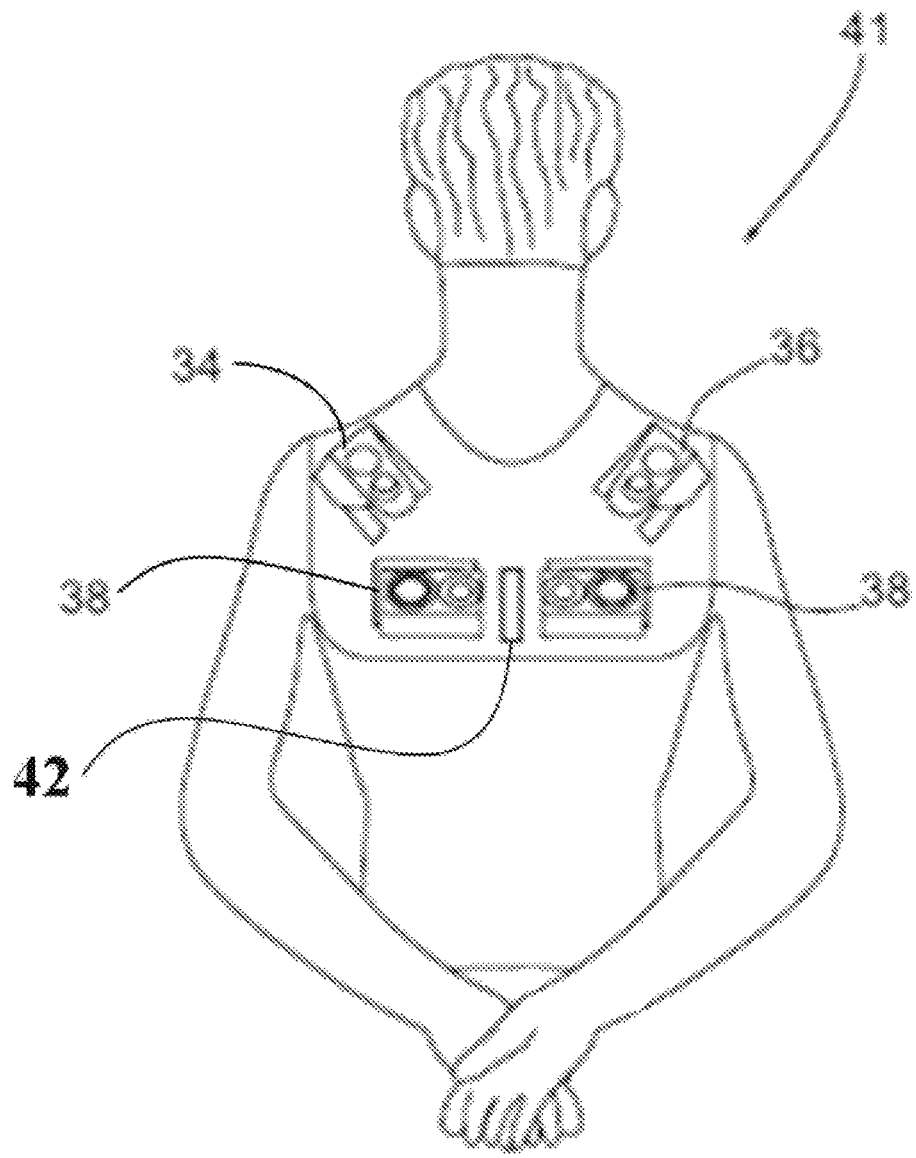
FIG. 4d is a schematic representation of the back of the user with the embodiment of 4b.

The usefulness of added speakers in the manner described is that individual may have a much more accurate sound experience which in turn may improve the individual's auditory experience. It may be an improved experience because the individual will now be better aware of the direction to which sounds are emanating from. Such an example would be an individual playing a game or a simulation whereby the individual is represented by a particular avatar in the virtual medium and wherever they are located the location of the sounds would be created relative to their location in the virtual medium; thus allowing for an accurate representation and greater level of awareness of their surroundings in this virtual medium. Furthermore, through this design each individual may be able to have the same sound experience as any other individual wearing the embodiment shown herein without having to worry about others or the environment, such as in a theatre with multiple people or at an individual's house with a surround sound system. Thus, the issue of a sweet spot (whereby a sound system only has a particular region that the sound is heard at the quality it is expected and outside that region it is not) may be eliminated because each individual is now located in their own sweet spot due to Individualized Local Sound. This may ensure whether you have multiple people in the same room, theatre, just one individual in one room or an individual moving from room to room the auditory experience remains the same. Furthermore it may allow individuals to wear garments 14 that are expected to be worn for their particular task (i.e. training, research) rather than wearing or using hardware that would not realistically be part of the experience. Such a situation where this may be beneficial is training. Whether it be military, police, fire, etc. this may allow individuals to wear the same garments they would in the actual real life situation rather than wearing particular equipment or having the equipment built into the environment, which could potentially alter the training experience and its benefits to real world scenarios. This may be important because it may allow individuals to be trained more realistically and may not matter how the environment is designed. Another major benefit of this design may be mobility; most current high end sound systems do not allow for great mobility. The ability to be mobile allows an individual to have the same experience on the go or in any particular environment with fewer adjustments to the Individualized Local Sound unlike other elaborate sound systems. In comparison to other mobile sound systems such as headphones, Individualized Local Sound allows for a more accurate localization of sound and can allow for an increased number of output locations for the sound to better represent what is occurring with a particular application (i.e. thus a greater auditory experience. Overall the creation of Individualized Local Sound allows for a more accurate, realistic, and personal sound experience that is unaffected by the individuals environment and therefore enhances the overall experience of any sound related application. As shown in FIGS. 4b, 4c and 4d, embodiment include a plurality of speakers 41 positioned to surround the head of the user on the shoulders of the garment 14, the upper chest and upper back, with an additional subwoofer 38 located on the back of the user. FIG. 4c depicts the front of the user while FIG. 4d depicts the back of the user. Embodiments may effectively create an individualized surround sound experience for the individual wearing it. The parts of the body chosen move little relative to the individual's ears; creating a mobile and consistent sound that is as dynamic as the individual.

Figure 13A:
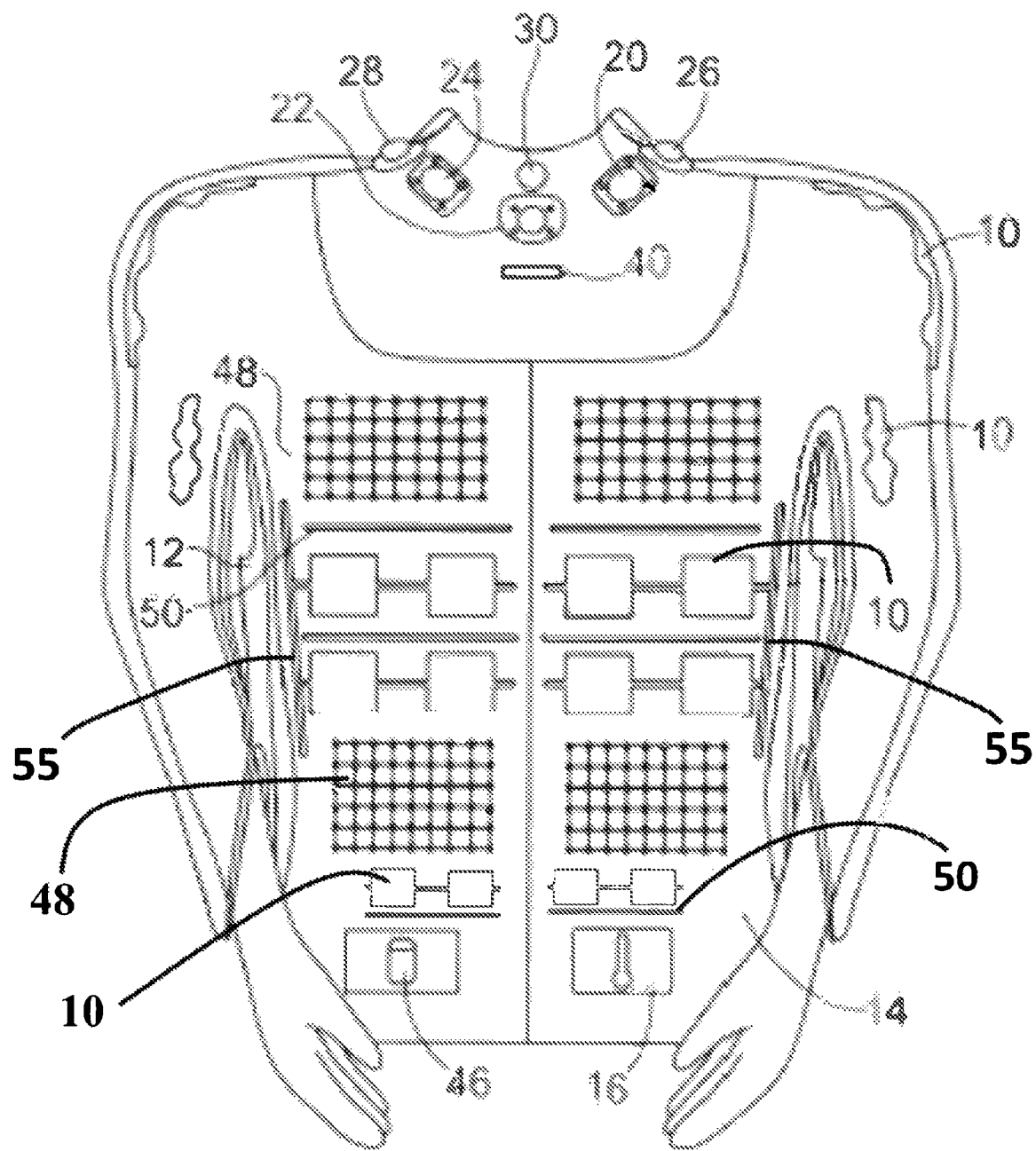
FIG. 13a is a schematic representation of the frontal view of an embodiment with individual surround sound (which may referred to as Two Way Voice and Multidirectional Audio Communication Interactive Media Device), Wearable Predetermined Electrical Stimulation Technology (WPEST), vibration actuators, force/compression actuators; this view is meant to be seen as if the garment were see through. This shows the different components that exist and does not show that they are on different layers of the suit. This is to show the different components that exist but does not include overlap as this would obscure from view those things underneath. Therefore, the componentry configuration shown is designed as a representation of the embodiment but the actual design may contain a greater number of Sensory Devices than shown here.
Figure 13B:
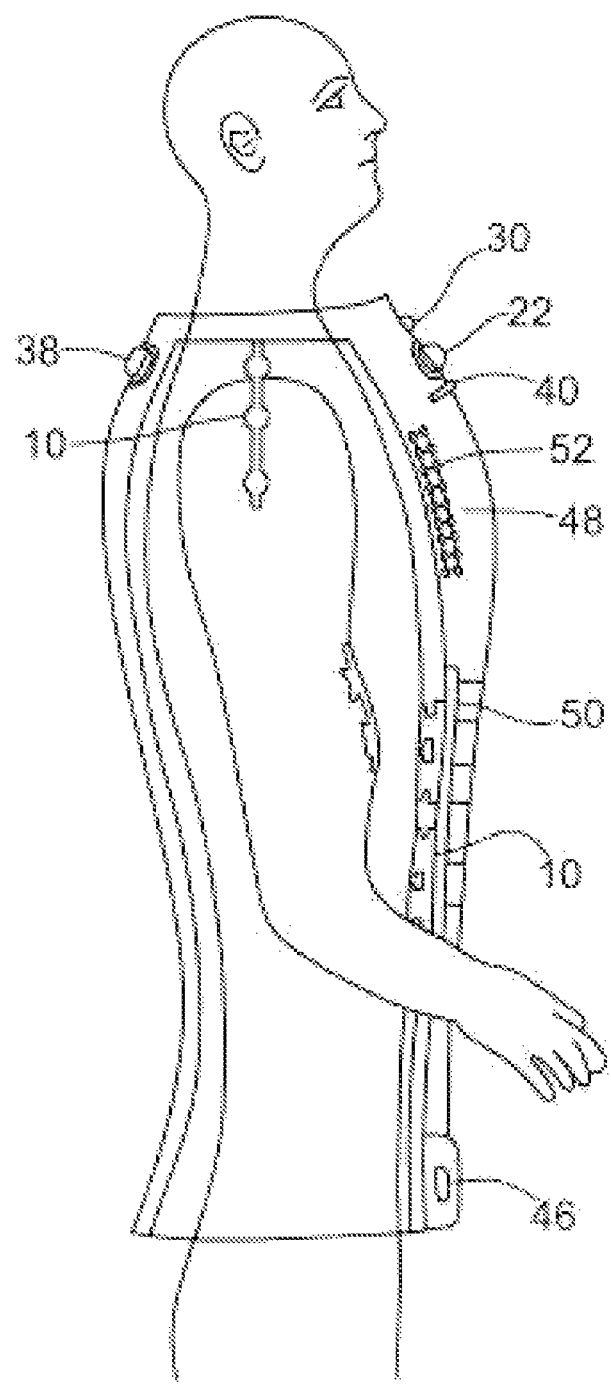
Figure 13C:
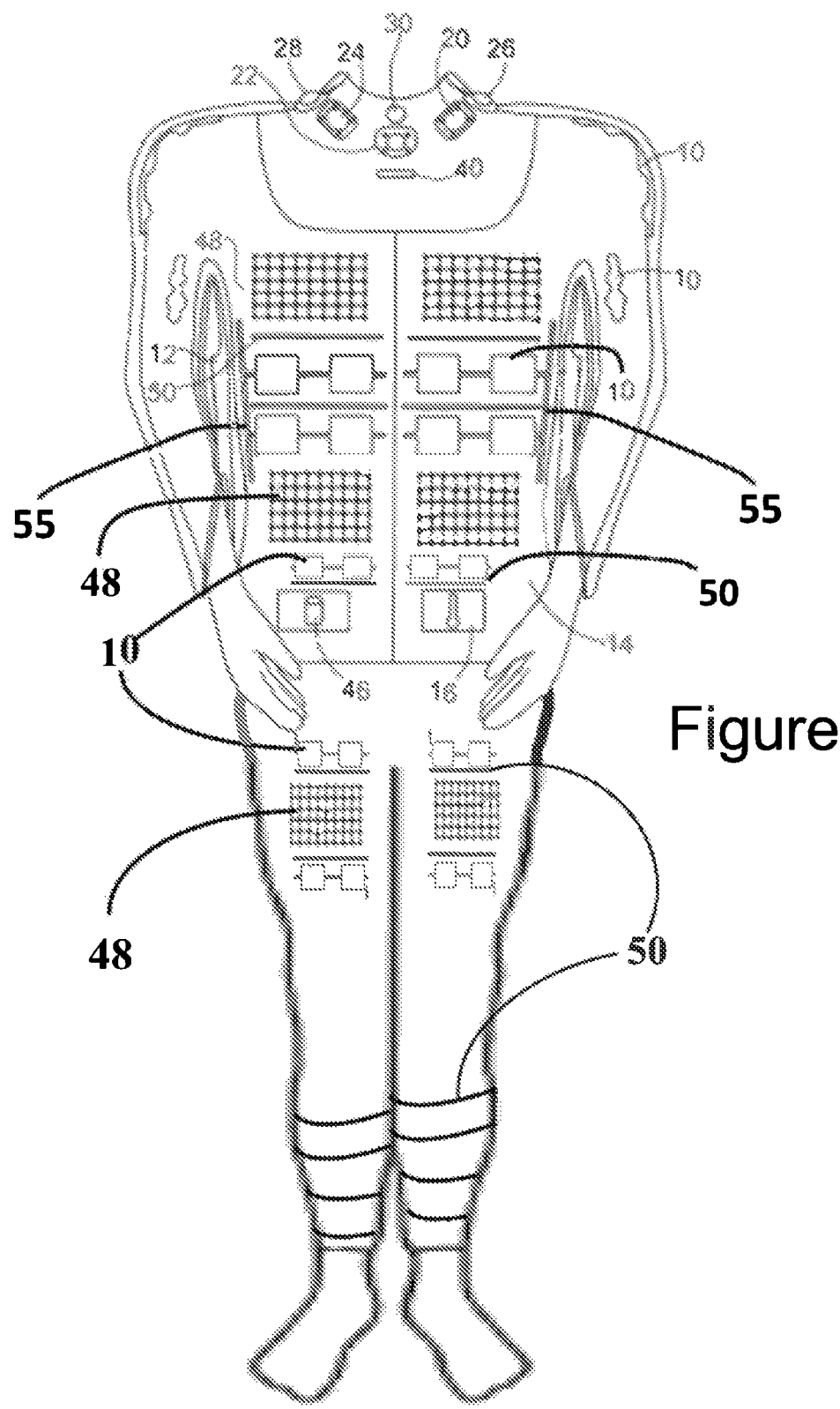

To represent the configuration of the Sensory Devices and componentry within a garment 14 the frontal view of one embodiment shown in FIG. 13c is separated into three garment areas of the body; one being the abdominal area (shown in FIGS. 5a, 5b, 5c, 5d); one being the upper torso or chest and shoulder area (shown in FIGS. 6, 7, 8); and one representing coverage of both the abdominal and torso area (shown in FIGS. 9, 10, 10a, 11). All components may be interconnected and representative of and make up an embodiment (e.g. as shown in FIG. 13c) whereby the synergy and totality of Sensory Manipulation and the Sensory Stimulations defined thereby implemented throughout the entire garment as defined by the Electronic Signal Pathway of the Sensory Event (e.g. as shown in FIG. 14) creates the Sensory Signatures which produce the desired Sensory Outcomes. This total body garment and experience is an example, and individual portions or combinations thereof may be used in other embodiments.

FIGS. 5a, 5b, and 5c show a frontal view of the abdominal area of an embodiment and, separate this view to show the different layers of the garment 14 and the components attached or affixed to or in each. This is to show the different components that exist but does not include any overlap as this would obscure from view those things underneath. Therefore, the componentry configuration shown is designed as a representation of the embodiment but the actual design will contain a greater number of sensory stimulation components than shown here.

FIG. 5a shows the inside first layer 14a which would contact the user or the users underlying clothing. Electrodes 10 are shown in FIG. 5a attached or affixed to the inner portion of the first layer 14a.

As shown in FIG. 5b, vibration actuators 48 and Force Simulation Device/Constriction/Compression Stimulation Device actuators 50 are depicted attached or affixed to the interior or the exterior of the second layer of the garment 14b. FIGS. 5b and 5c shows the Control Centre 16 and power regulator 46. FIG. 5b shows the Control Centre 16 and power regulator 46 attached to the exterior of the second layer 14b. FIG. 5c shows that the Control Centre 16 and power regulator 46 may even protrude through the third layer 14, giving the user access.

Figure 6:
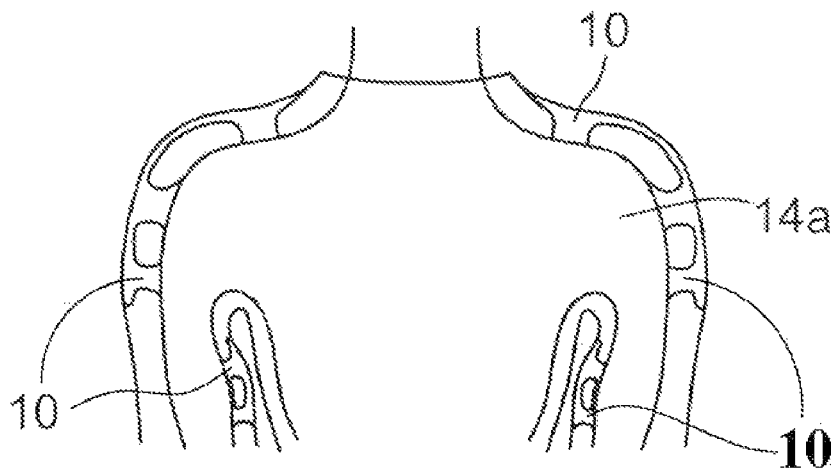
FIG. 6 is a schematic representation of an embodiment with electrodes attached to the first layer of the garment.
Figure 7:
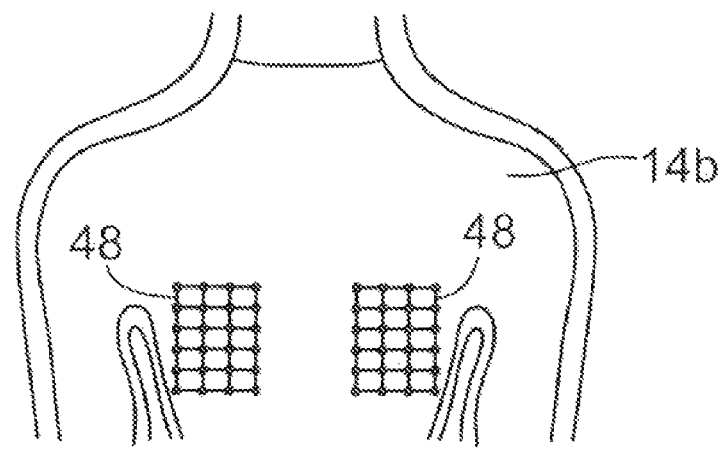
FIG. 7 is a schematic representation of an embodiment with vibration actuators attached to the second layer of the garment.
Figure 8:
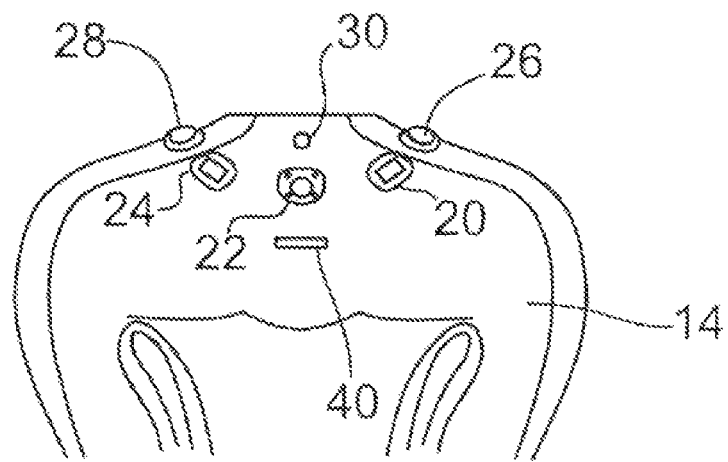
FIG. 8 is a schematic representation of an arrangement of the speakers and their location on the garment.
Figure 9:
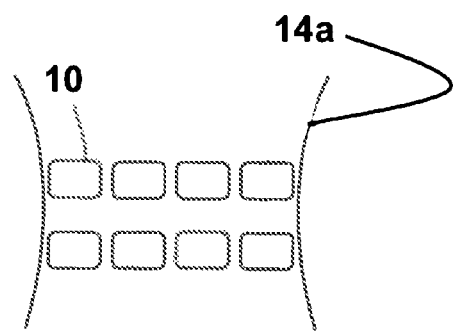
FIG. 9 is a schematic representation of an embodiment with electrodes attached to the first layer of the garment.

FIGS. 6, 7 and 8 show a frontal view of the upper torso and chest area of an embodiment and, separate this view to show the different layers of the garment 14 and the components attached or affixed to or in each. This is to show the different components that exist but does not include any overlap as this may obscure from view those things underneath. Therefore, the componentry configuration shown may be designed as a representation of the embodiment but the actual design will contain a greater number of sensory stimulation components than shown here.

In the embodiment shown in FIG. 6, electrodes 10 may be attached to the inner portion of the first layer of the garment 14a. Vibration actuators 48 (another example Sensor Device) which may be located in predetermined locations to either the exterior of the first layer 14a or interior of the second layer 14b as shown in FIG. 5b and FIG. 7. Similarly the speakers 20, 22, 24, 26, 28, subwoofer speakers 38 (not shown), microphone 30, microphone jack 32 (not shown) and power source 40 of the surround sound system each may be located in a defined and predetermined location on the interior or exterior of the third layer of the garment 14 as shown in FIG. 8. The components of the surround sound system may have a similar layout as shown earlier in FIGS. 4a, 4b, 4c and 4d. Additional electrodes 10 may be included in addition to those shown in FIG. 5a, FIG. 6 and FIG. 9. These additional electrodes 10 may be attached to the inside layer of the garment 14a in defined and predetermined locations.

Figure 10:
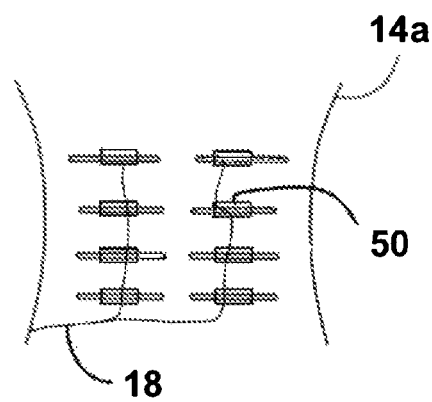
FIG. 10 is a schematic representation of an embodiment with Constriction/Compression Stimulation Device actuators on the second layer of the garment.
Figure 10A:
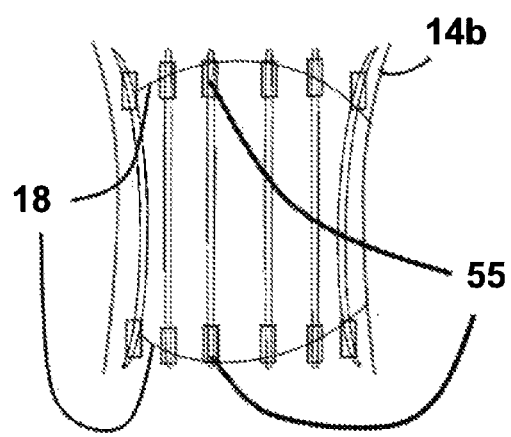
FIG. 10a is a schematic representation of an embodiment with Force/Physics Simulation Device actuators on the second layer of the garment.

FIG. 10 shows Constriction/Compression Stimulation Device actuators 50 in defined and predetermined locations and attached to the exterior of the first layer of the garment 14a. FIG. 10a shows Force Stimulation Device actuators 55 in defined and predetermined locations and attached to the interior of the second layer of the garment 14b.

As depicted in the embodiment of FIG. 10, the actuators 50 run in a grid-like fashion, top to bottom seemingly overlapping one another. FIG. 10 shows one group of actuators 50 that encircles the body. The actuators may encircle the body running in parallel across the body horizontally i.e. left to right or right to left where the actuators are located on the exterior of the first layer 14a.

Figure 11:
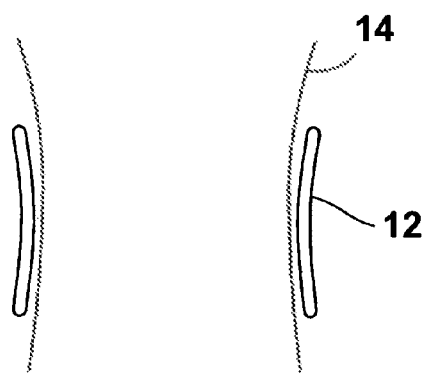
FIG. 11 is a schematic representation of an embodiment with MCEIATR attached to the exterior of the garment.

FIG. 10a shows one group of actuators 55 that runs up and down the body in parallel with each other. The embodiment exhibits where the actuators may run vertically i.e. top to bottom on the interior or exterior of the second layer of the garment 14b. FIG. 11 shows an embodiment where the MCEIATR 12 is in a defined and predetermined location(s) and attached to the exterior layer of the garment 14.

FIG. 10 and FIG. 10a shows the position of the actuators 50, 55 of the Constriction/Compression Stimulation Device/Force Simulating Device. The Force Simulation Device may apply physical forces to an individual so that they feel particular sensations that would normally pertain to a particular real world event. Such sensations could be but not limited to imitating the centrifugal force that is felt as an individual driving turns a corner, someone pushes or bumps into an individual, or the weight of carrying something on ones shoulders, and so on. Other forces may also be simulated. The Force Simulation Device may be able to directly apply these forces to specific locations of the body as it is a form of wearable technology. Thus, the Force Simulation Device may be integrated into the garment 14.

The Force Simulation Device (actuator 55) allows for localized forces to be applied to an individual. Through the use of a computing device it allows a Force Simulation Device to alter such parameters as the amount of force that is applied (minimal to maximum), the speed at which the force reaches its target amount (fast or slow), the duration to which the force is applied (amount of seconds or deactivates one target force is reached) and the speed at which the force is removed (fast or slow). Through these different parameters it allows for a multitude of forces to be simulated at a given location within the garment 14 an individual is wearing. In addition, by extending the Constriction/Compression Simulation Device 50, Constriction/Compression Stimulation Device actuator 50, and Force Simulation Device 55, Force/Physics Stimulation Device actuator 55, to cover multiple regions of a garment or garments 14 which in turn covers a larger region of the individual (as shown in FIG. 13c) which increases the amount of forces that can be applied simultaneously and the ability for an individual to more accurately determine the direction of the force as well as what the force might represent for a particular application. Such sensations that could be created are that of a strong or weak, gradual or quick, constant or instantaneous simulated force in one or multiple locations simultaneously.

Force Simulation Device is useful as it allows for virtual mediums to have an increased immersive experience as a force applied to the body will give the intensity of the force applied and the direction to which the force came from based on its location in the garment 14. In addition, the use of a Force Simulation Device for simulations and training creates additional forces for the particular application giving a more realistic experience. This increase in realism better prepares individuals for the real world experience to which the simulations and training are designed for.

For example, in a simulation, the individual is moving backwards and encounters an obstruction; the individual may immediately feel the height of the object and can determine, without turning around, whether it is possible to climb or jump over or whether to find another route.

In one embodiment, shown in FIG. 10, linear actuators are attached to the exterior of the first layer of the garment 14a. FIG. 10 depicts potential Constriction/Compression Stimulation Devices 50 being actuated via a wired connection 18 as determined by the Control Centre 16 (not shown). In this illustrative example, the actuators draw in their attached 1" nylon webbing which shortens the length thereby reducing the diameter of the webbing which circumnavigates the user and performs a constricting action.

In another embodiment, FIG. 10a depicts a potential implementation of Force/Physics Stimulation Device 55; linear actuators are attached to the interior or exterior of the second layer of the garment 14b. They may be actuated via a wired connection 18 as determined by the Control Centre 16 (not shown). The shortening of the vertical webbing may cause a pulling action which draws down on the users torso as if gravity is affecting the user.

The Constriction/Compression Stimulation Device 50 and Force/Physics Stimulation Device 55 may be used with any computing device to create the effects. The computing devices may be but is not limited to using the Constriction/Compression Stimulation Device and Force/Physics Stimulation Device 55 to sync the sensations with a virtual medium or in use in real world applications.

The Constriction/Compression Stimulation Device allows computing devices to add to their applications the capabilities of applying a compression and/or constrictive feeling to a location of an individual's body. This sensation may also be described as tightening, pressure, crushing, squeezing, and contracting. To properly compress or constrict a part of an individual's body the Constriction/Compression Stimulation Device is a form of wearable technology. The Constriction/Compression Stimulation Device is integrated into a garment 14.

Through the use of a computing device the Constriction/Compression Stimulation Device can have various parameters altered to effect the sensation of constriction/compression and squeezing such as but not limited to the pressure (minimal or a lot), tightening (minimal or a lot), speed that squeezing or constriction/compression occurs or is removed (fast or slow), the length the constriction/compression is activated for (multiple seconds or once fully activated revert to deactivated state) and the ability to fluctuate between these settings while already activated. Furthermore, since the Constriction/Compression Stimulation Device is wearable technology it may allow for accurate constriction/compression as it will be directly against the individual's body and localized to a particular part of the individuals body. In addition, this Sensory Manipulation or Sensory Stimulation can be extended by having multiple regions rather than just one that can be activated to simultaneously squeeze, contract, crush or constrict an individual's body. Such Sensory Manipulation or Sensory Stimulation could be used in a virtual medium to provide but is not limited to, the sensation of something having a hold of the individual such as a hand having a tight grip on the persons shoulder, something wrapped around the individual that is squeezing tightly and maintaining the amount of pressure the individual feels or representing an object falling on an individual and pinning them whereby the pressure continues to get more and more intense. As for the medical rehabilitation industry, this could have implications in that an individual could be using wearable technology with the Constriction Simulation Device to effectively squeeze and constrict particular areas of their body to help them recover while the individual focuses on other activities. Overall this Sensory Stimulation provides an individual with the particular sensation of one or more locations feeling pressure or constriction/compression of varying degrees.

The Constriction/Compression Stimulation Device can use any technology that can selectively and controllably restrict areas of the garment 14. The actuators of the device may be one or more of, but is in no way limited to: polymeric artificial muscles, liquid filled bladder(s), piezo-electric actuators, electronic polymeric actuators, Carbon Nanotube Artificial Muscles, linear actuators, winding or tensing elements or other systems.

Polymeric artificial muscles, electronic polymeric actuators (EPAs) and carbon nanotube artificial muscles are materials that expand or contract, lengthen or shorten when energy is passed through them. The lengthening and shortening provides the ability to pull and push as well as decrease or increase the circumference of its measurement while encircled around something. Winding and tensing elements like linear actuators can be electronic DC activated devices. Unlike EPAs they are only the actuator and must be connected to something that they can move. The item they attach to (webbing, strapping, and cable, and so on) may lengthen or shorten as the anchored actuator operates. They may also have the ability to pull and push as well as decrease or increase the circumference of the measurement its strapping is encircled around. Further usefulness of the Constriction/Compression Stimulation Device is due to its positioning as a wearable technology; it can accurately affect the same region on an individual's body with Sensory Stimulations reproducing the Sensory Event and repeatedly providing the desired Sensory Signature or Sensory Outcome. Furthermore the ability to apply this specific Sensory Manipulation through any part of the garment 14 allows multiple regions to be affected simultaneously and with different effects allowing for a multitude of Sensory Stimulation rather than general compression and constriction. In regards to virtual mediums this can allow them to implement new combinations of Sensory Stimulations to provide a more immersive experience. While for real world scenarios this could provide the particular sensation of pressure that otherwise could not be replicated.

Further Sensory Stimulation and Sensory Manipulation whereby a person's physiology is stimulated to sense various, intended and specific sensual outcomes which are associated with the real world but are only being replicated is actuated through vibration technology 48 (as shown in FIG. 5b for example). The actuators of the Sensory Device may be one or more of, but is in no way limited to: electronic or pneumatic or hydraulic actuators, electronic polymeric actuators, linear actuators, brush coin actuators, piezo-electric actuators, vibration motors, tactile transducers, ultrasonic pads, and or mass actuators. This Sensory Stimulation and Manipulation can optionally be incorporated in a manner that the computing device selectively identifies which areas of the garment 14 are to be activated; whether that is the entirety of the garment 14 or individual areas such as upper back or right arm etc. This may be done to imitate sensations such as disorientation, direct impact, skin crawling or when the individual's avatar is in a plane or automobile, and so on.

Figure 12A:
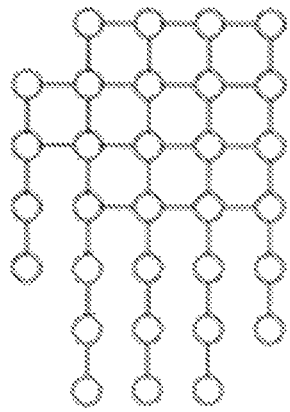
FIGS. 12a to 12i are schematic representations of arrays of actuators, which may be referred to as a "Sensory Event Array," and each representation shows a different example combination of actuators being actuated either simultaneously in sequence or a combination of both.
Figure 12B:
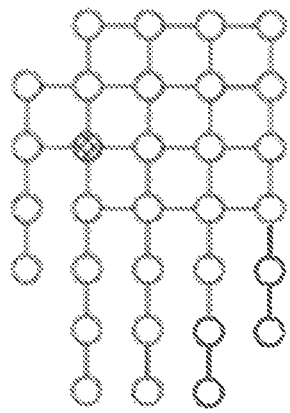
Figure 12C:
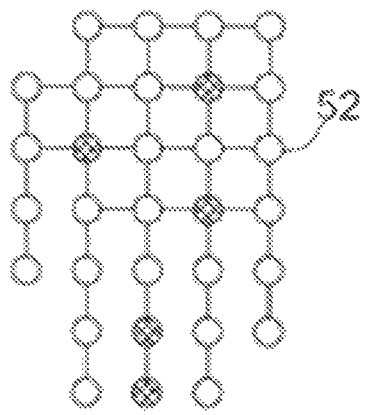
Figure 12D:
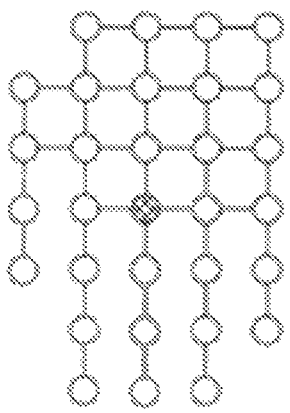
Figure 12E:
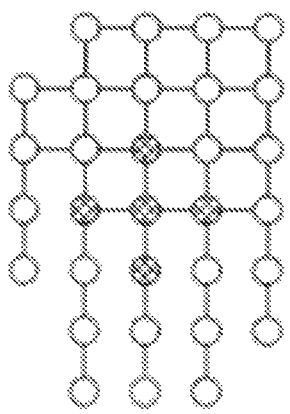
Figure 12F:
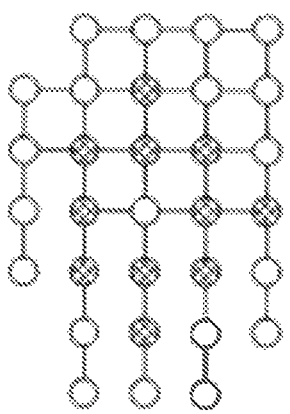
Figure 12G:
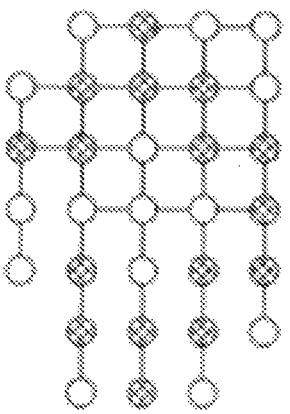
Figure 12H:
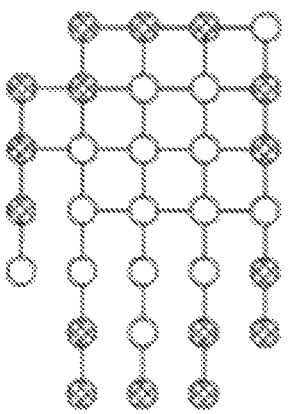
Figure 12I:
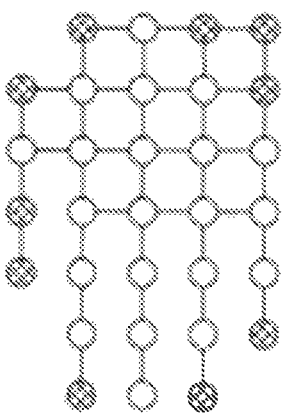

As it is beneficial in the creation of Sensory Events or Sensory Signatures, and ensuing Sensory Outcomes to provide the greatest number of Sensory Stimulations to the user, FIG. 12a through 12i represents some of the actuation and dispersal pattern possibilities of the different combinations of Sensory Device activations. These are illustrative and non-limiting example patterns. There may be singular coverage, multiple coverage, regional coverage or total coverage and may be in arrays, Sensory Event Array(s). The actuators for the force, constriction/compression, vibration and electrical stimulation (e.g. electrodes) 52 in FIG. 12c are preferably situated in the garment so that any activation(s) may form in arrays in the garment 14 as shown in all of FIG. 12. Each dot as shown in all of FIG. 12 may be representative of one or more of these Sensory Device actuations. The different Sensory Events making up the Sensory Event Array may be activated simultaneously, sequentially or through a combination of both simultaneous and sequential activation to produce Sensory Stimulations. This may allow for any computing device to effectively have precision haptics allowing for single location Sensory Stimulation on a user via a Sensory Event or single and multiple location stimulations on a user via a Sensory Event Array culminating in one or more Sensory Signatures for the user.

Sensory related data received from a computing device may create a multitude of stimulations at the position it is located on an individual's body. The location or selection of a Sensory Event may depend on the output of the computing device. The Sensory Event may define different areas or locations of Sensory Devices to actuate to produce Sensory Stimulations. Through the computing device a Sensory Event can be activated to create one or more particular Sensory Stimulation(s) or Sensory Signature, at its location. Through the implementation of multiple Sensory Events creating a Sensory Event Array, the sensory related data received could have a single Sensory Event activated or multiple Sensory Events activated. Furthermore, during the activation of one or more Sensory Events other Sensory Events could be activated and the already activated Sensory Events can be updated to deactivate them or alter the Sensory Stimulation or Sensory Signature, they are creating. This allows the creation of a single or multiple Sensory Stimulation effects simultaneously, sequentially or intermittently in one or more locations on an individual's body for Sensory Events. The placement of a Sensory Event may determine what part of an individual's body feels the stimulation while a Sensory Event Array of FIGS. 12a-12i may be localized to a particular part of an individual's body such as the hand, it could cover the entire arm or it could even cover the entire body depending on its use. Also, depending on the amount of precision required an Sensory Event Array can be created so that the proximity of the Sensory Events in the Sensory Event Array of FIGS. 12a-12i are closer or further apart and the location is entirely dependent on the application and uses for the technology; such that simulations and medical applications may require exact precision while entertainment may be feasible with approximate locations.

In one embodiment, the wearable device is able to create accurate precision Sensory Stimulation as well as unique Sensory Stimulations dependent on the sensory related data received to activate a Sensory Event. The sensory related data is not limited to affecting the stimulation's duration, intensity and radius, as shown in FIG. 12a-12i. To further increase the effectiveness of a Sensory Event, many Sensory Stimulations can be combined together to create a multitude of stimulation effects and creates a Sensory Event Array (e.g. FIGS. 12a-12i). In this regard, Sensory Stimulations can be created that covers a much larger area but retains the ability to be just as precise from one Sensory Event to the next. Thus the Sensory Stimulations may still replicate stimulation at a single locale (FIG. 12b) or at multiple locals simultaneously (FIG. 12c), sequentially or a combination of the two. The Sensory Signature(s) or Sensory Events and ensuing Sensory Outcome(s) that may be created is not limited to Sensory Manipulation or Sensory Stimulation of a single Sensory Device or a singular Sensory Event or a singular Sensory Event Array. Nor is it limited to the Sensory Manipulation of multiple Sensory Devices or multiple Sensory Events or multiple Sensory Event Arrays. It may initiate as one or the other and expand or contract to provide more or less Sensory Stimulation to the user in some embodiments. Therefore, Sensory Signatures or Sensory Events and ensuing Sensory Outcomes may contain multiple Sensory Stimulations activated to represent stimulations from a single source to multiple stimulations activated to represent Sensory Stimulations from multiple sources to a combination of single and multiple Sensory Stimulations from one or more sources. In the context of a video game, there are various uses for this technology; such as, although not limited to, the activation of one or more Sensory Events to create the specific Sensory Signature (or combination of Sensory Stimulations) such as the effect of bullets impacting or shrapnel of a grenade or rocket impacting off armour; a slice from a knife or sword whereby multiple Sensory Events are activated sequentially one after another affecting different Sensory Devices 52 of the Sensory Event Array of FIGS. 12a-12i in a line or particular pattern. For example in FIGS. 12d to 12i a ripple effect starting at a particular location on the Sensory Event and working outwards much like a concussion effect; a wave effect whereby it starts at one or multiple locals to create a stimulation across a line that moves from a particular part of an Sensory Event Array to another part of the Sensory Event Array; a stimulation completely across the Sensory Event Array much like something being scanned; or trying to scare an individual in a haunted house by creating the feeling of something moving across an individual's back but visually there is nothing there. Overall, whatever the desired Sensory Outcome of a single Sensory Event or multiple Sensory Events in the form of a Sensory Event Array, the number and layout of the Sensory Events is entirely dependent on the Sensory Outcome defined by the Sensory Manipulation. Embodiments may implement use of a single Sensory Event to be able to create precision Sensory Signatures (or combination of Sensory Stimulations) for the user and have an ability to be expanded upon to create such a variety of Sensory Outcomes.

In another embodiment Sensory Events may produce Sensory Signatures (or combination of Sensory Stimulations) and Sensory Outcomes through Sensory Device activations to certain coverage areas of the body: singular coverage; multiple coverage; regional coverage; total coverage; and dispersal coverage. A singular coverage area may include just one area of the body. It may be a specified area of small coverage and the Sensory Event may include the actuation of one or more Sensory Devices within the Nervous System to create Sensory Stimulations. For example, singular coverage may include Sensory Device activation(s) in the proximal portion of the arm (humorous, biceps, triceps, and upper-arm). The singular coverage areas actuate as determined by the Control Centre activation signals. Multiple coverage areas include two or more singular coverage areas of the body. They may be adjacent body areas or detached from one another. This Sensory Event may be made up of specified areas of coverage and may include the actuation of one or more Sensory Devices within the Nervous System. For example, multiple coverage areas may include the proximal portion of the arm (humorous, biceps, triceps, and upper-arm) and the connecting deltoid/shoulder. Or multiple coverage areas may include the proximal portion of the right arm (humorous, biceps, triceps, and upper-arm), the left medial pectoral/chest and the right lateral portion of the abdomen. The multiple coverage areas will actuate as determined by the Control Centre activation signals. Regional coverage area includes adjacent quadrants or sections of the body. A Sensory Event to these specified areas of coverage may include the actuation of one or more Sensory Devices within the Nervous System. For example, regional coverage may include the thoracic and abdominal cavity both medial and lateral. Or regional coverage may include the proximal and distal portion of the left arm, the adjacent left shoulder, chest and abdominal areas. The regional coverage areas will actuate as determined by the Control Centre activation signals. Total coverage area includes all coverage areas of the body. The Sensory Event for this specified coverage may include the actuation of one or more Sensory Devices within the Nervous System to produce Sensory Stimulations. For example, all areas of coverage would provide Sensory Stimulation to the user: arms, legs, and torso. The total coverage areas may actuate as determined by the Control Centre activation signals. Dispersal coverage is similar to the Sensory Event Array and includes one, two or more singular coverage areas of the body. When more than one singular coverage area is involved they are adjacent body areas. The Sensory Event initiates in one specific point in the singular coverage area and radiates, moves, flows, ebbs, surges outward, inward, up and down, etcetera to the end of this singular coverage area and then continues flowing where necessary through other coverage areas as directed by the Control Centre activation signals. For example, the Sensory Event starts in the distal portion of the right lower arm and pulses in a wave like fashion up through the proximal portion of the arm into the right shoulder and down into the right chest area of the user. The dispersal coverage areas will actuate as determined by the Control Centre.

Additionally, the connectivity of the Sensory Events to make a Sensory Event Array is adaptable through software. This allows developers the ability to virtually connect Sensory Events together to make a Sensory Event Array to easily implement the applications desired Sensory Signatures (or combination of Sensory Stimulations) and Sensory Outcomes. Furthermore, by making the connection virtual it allows the hardware integration to be determined by the hardware developers so it best suits the device the technology is integrated into. This ensures that the hardware integration and software integration of the Sensory Events does not limit the usefulness or determine the use of the technology.

Greater immersive Sensory Stimulation and virtual world awareness may be created through the perception of real world sensations. The real world environment provides a multitude of sensations depending on what an individual's senses receive. These triggered Sensory Stimulations allow an individual to effectively perceive our world and the things that are in it. Everything in the world has various forms of sensory feedback that they can provide an individual with which makes up their "Sensory Signature" which may be a particular combination of Sensory Stimulations. For example, the C-5 Galaxy (a military aircraft) has a particular Sensory Signature that would make it unmistakable. Even without being able to see the C-5 Galaxy, the sound, pitch, vibration and overall sensation that one feels when the plane is flying overhead would make it unmistakable and easily identifiable. Such real world signatures can be transferred to the gaming realm or other types of virtual reality. A gaming example; if an individual is playing a zombie survival game and hears particular noises of shuffling of feet, strange groans or just outright being attacked by zombies and feels something touch your back or grab you, the Sensory Signature that a zombie has would help identity whether particular sensations are from a zombie or an ally. This could provide enough sensory information to determine an effective plan of action. Or, the individual's avatar is moving backwards away from gun fire and is stopped because it backed up into something. The individual can instantly feel it on their back and make immediate adjustments. This in game decision making also translates into greater competence during game play as each more intuitive decision leads to greater "in game" success. This same methodology applies to movies as well as training simulations. In addition, sensation rehabilitation can be applied to traumatic accident, stroke or burn victims for example, whereby their nerves and brain can relearn through the Sensory Signature applications, especially though electrical stimulation. In addition, children who have no perception of various sensations due to their disabilities may learn through Sensory Signature applications.

The embodiments shown herein may allow for the reliability of Sensory Event and Sensory Signature outcomes. It creates this reliability in its consistent reproduction of outcomes as provided through the repetition of applications. Reliability refers to the consistency in the reproduction of the Sensory Event and the subsequent Sensory Signature for the user. For example, if a severe leg burn victim has limited feeling in their leg and physical/physiotherapy is required over a period of time, the sensual stimulation must be repeated and must be consistently applied through a repetitive process in order to produce reliable desired results.

In addition, embodiments have technological interoperability. Technological interoperability refers to the device's ability to operate between fields of use. This interoperability includes the ability of an embodiment to work in these other fields. For example, someone playing a video game can wear the device and receive stimulation as per the communications protocol set out in the Control Centre specifications. On the other hand, that same individual may come home from work and find they have a shoulder muscle that is tight and needs massaging and may use the device as per communications protocol initiating from computing device or may use the device as per the communications protocol initiating from computing device. The device he or she wears for video games thus can also be worn for this purpose as well, physiotherapy. Alternatively this person may want to go to the movies or partake in a training simulation where the same device is also worn. As mentioned previously, only the Decoder potentially needs to be altered when changing platforms. One could do this via physically changing the Decoder 56, or alternatively by changing the software of the Decoder 56.

The combination of the components detailed herein results in various embodiments with various unique and innovative features. It allows for a complete and more holistic experience that encompasses more of one's senses than just video and stereo-audio. Examples include: a player is provided surround sound and hears (as well as sees) bugs crawling on their character and receiving through Sensory Manipulation the Sensory Signature of something crawling on their stomach through a Sensory Event Array as provided by vision, EMS, vibration and sound. Another example would be military training whereby surround sound gives directional feedback from an explosion and the Sensory Signature is created by vision, sound, muscle stimulation, vibration, force/physics, air blast and constriction/compression simulating shrapnel entering the soldier's body and the concussive force of the explosion. Additionally, a blind person walking in a city is given directional cues either audibly or physiologically with the other used as a proximity warning for close or closing obstacles or dangers. A theatre goer is sitting in a movie theater wearing the device where the surround sound provides directional sound with the sensory stimulation components providing stimulation to the viewer's body as the main character of the film is experiencing it in the movie.

FIG. 14 depicts a potential pathway from the initiating device 54 that the signal takes to get to an actuator. The initiating device 54 may provide an input module. The initiating device 54 is a computing device that uses software to collect sensory related data and create control data that will determine what physiological stimulation each pair of electrodes 10 or other actuator will create at any given point in time. A computing device that allows for the inclusion of software and the output of data that the software has generated can be used as an initiating device 54 for the system. The Control Centre 16 is the component of the system which controls the signal, duration, strength, and/or pattern of the electrical stimulus generated causing or activating a Sensory Event, whether singularly, in a Sensory Event Array, random or other formation. The Control Centre 16 may provide an input module for collecting sensory related data. A Decoder 56 can potentially be operably connected between the initiating device 54 and the Control Centre 16. The Decoder 56 is used to decipher or transform the data being sent from the initiating device 54 into a format compatible with the Control Centre 16. This deciphered data is then sent from the Decoder via a communications protocol to the Control Centre 16. Input data to trigger different Sensory Events may be collected through an input module coupled to Decoder, initiating device 54, or Control Centre 16.

There may optionally be an additional computing device between the actuator and the Control Centre 16 that is actuator specific 12a such as an EDA. Another example is the MCEIATR 12 which sends the electrical impulse to the electrodes 10 and subsequently the Sensory Manipulation or a Sensory Event, whether singularly, in array, random, and so on. The determination on which pairs of electrodes 10 are activated and the level, duration, strength and or pattern that each electrode pair 10 will produce is based on the sensory related data received from a Decoder 56.

In addition, the data can be sent from a MCEIATR 12 alone, or as described before an initiating device 54 can initiate the process through a virtual medium or device through the Decoder 56 to the Control Center 16 which is operably connected to the MCEIATR 12 which sends electrical impulses to the electrodes 10. The MCEIATR 12 may optionally also be defined in the garment 14.

In the one embodiment, parts of the garment 14 are electrode conductive as to give an effective, wireless electrical pathway between a MCEIATR 12 and an electrode 10, while other parts are not conductive as to inhibit certain circuits and to control the areas that are being stimulated. Therefore, in this embodiment it may also be advantageous to include wired electrical pathways 18 between some MCEIATRs 12 and some electrodes 10. In both these connections, the MCEIATR 12 is operably connected to at least one pair of electrodes 10.

In one embodiment, some or all of the components including; the electrodes 10, computing device 54, MCEIATR 12, control center 16, initiator 54 are removable from the garment 14 as to allow for repair, instrumentation calibration, replacement, battery replacement, cleaning or other general maintenance (henceforth referred to as maintenance). They may be attached or fastened to the garment 14 via using an adhesive technology. Adhesive technology consists of any technology that allows for the removal of electrodes 10, other actuators or other components for maintenance. It may be one or more of; VELCRO®, hook and loops or clasps or pouches. However, the list is just exemplary and should in no way be interpreted as limiting.

For various embodiments, the Decoder 56 may need modification depending on the initiating device 54 being used. In one embodiment, one can buy a new Decoder 56 for every initiating device 54 the person wishes to connect to the garment 14. Alternatively, one could alter the programming of the Decoder 56 meaning an individual may only need to install software or a patch to move to a different initiating device 54. However, if a platform were designed to output data consistent with what is read by the Control Centre 16, the use of a Decoder 56 would not be necessary and no changes to the hardware or software would be necessary with switching to the designed initiating device 54.

The power source (Power Regulator) 46 for the device may be any source that effectively allows the function of the device. This may include, but is no way limited to; rechargeable batteries, replaceable batteries or directly wired into a power source such as an outlet, or a combination thereof.

Figure 15:
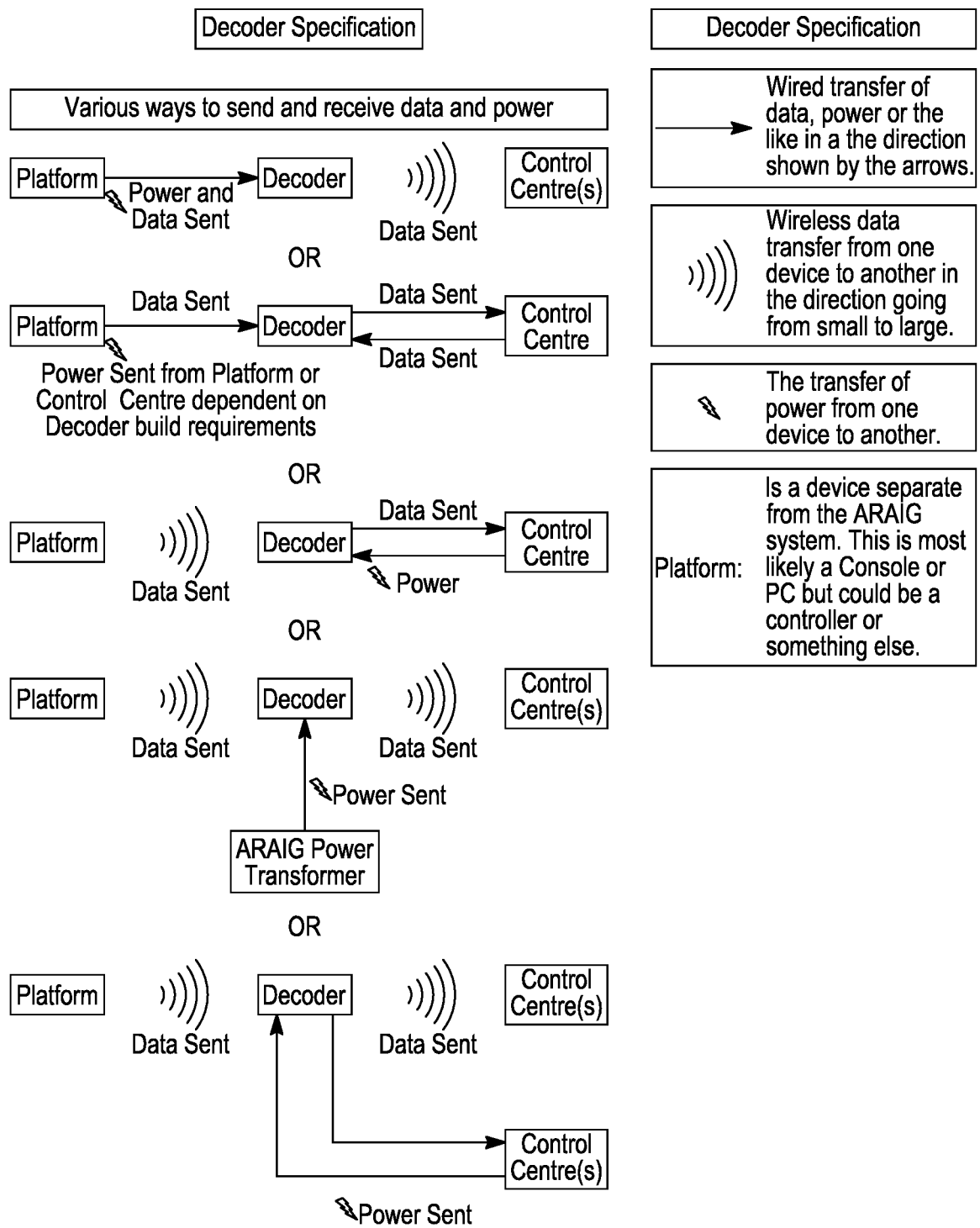
FIG. 15 illustrates Decoder specifications according to some embodiments.

Referring now to FIG. 15 there is shown an example Decoder specification, along with a legend depicting various elements of this and other figures.

A Decoder may be capable of receiving the needed sensory related data wired or wirelessly from the initiating device, or other computing device. A Decoder may be capable of altering or transforming the data sent from the initiating device into data that is then sent wired or wirelessly to the Control Centre to activate the Exoskeleton's Nervous System appropriately.

A Decoder may be capable of receiving software updates via a platform computing device and from the Control Centre. A Decoder may be capable of updating the software of the Control Centre if its software is outdated. A Decoder may be capable of receiving its power from a Control Centre when attached to a Control Centre or computing device when attached to a computing device but when completely wireless for both sending and receiving of data it needs to be attached to the Power Transformer for power. There may be a different Decoder for different computing device platforms (e.g. PS4, PC, Xbox360, Xbox One) and more as they continue to come to market or as we enter different markets.

A Decoder may be designed specifically for one or more forms of transmission to work with a particular platform (wired and Bluetooth, etc.). If multiple devices use the same data transfer protocols it is possible for some Decoders to work for several platforms.

Decoder is designed to receive data from a platform either wired, wirelessly or both. Each Decoder may be able to physically connect to a Control Centre to send the Data to that Control Centre and may be able to send the data wirelessly to one or more Control Centres simultaneously; the latter may not require physical connection to a Control Centre. The wired and wireless transmission of data to one or more Control Centres may be the same for each Decoder while the wireless and wired transmission from a platform may be specific to each platform, although all Decoders will be able to connect to a PC. Thus, there will be a variety of Decoders designed to receive Data from various platforms.

For a Control Centre to receive data from a Decoder to Decoder may first be synced with the Control Centre. Once synced a Decoder can then be used wired or wirelessly for that particular Control Centre. Multiple Control Centres can be synced to the same Decoder to receive the same information wirelessly. Each Decoder may receive power to turn it on externally, either through the Platform, a Control Centre or ARAIG's Power Transformer. When wired it is connected to the device physically. This physical connection will most likely be via a USB for ease of use. When wireless the Decoder is either sending and/or receiving via one or more wireless protocols. A Decoder also can download software updates and patches via various Platforms (at least via a PC) when wired to that Platform. Also, updates and patches can be sent or received from a Control Centre.

Figure 16:
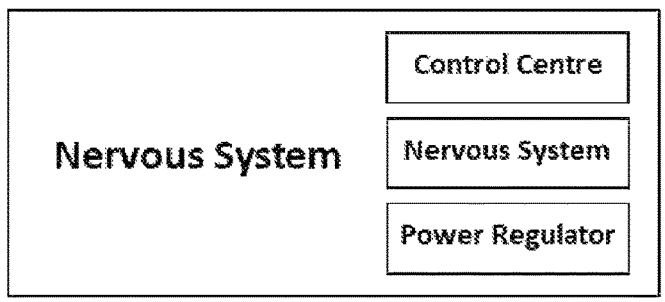
FIG. 16 illustrates exoskeleton specifications according to some embodiments.

FIG. 16 illustrates exoskeleton specification according to some embodiments. The example exoskeleton may include an upper body suit that covers the torso, shoulders and upper arms that has all of the core functionality working and integrated where required. The exoskeleton may include a Control Centre (e.g. Power Button (Integrated), Mem Chip (Detachable), Profile Selector (Integrated), Receiver (Integrated)), a Nervous System (e.g. Vibration Components (Integrated), STIMS (e.g. Medically Compliant Electrical Impulse Amplifier Transmitter Receiver(s) (MCEIATRs) (Integrated), Paired Electrodes (Integrated), Electrode Pads (Detachable)), Surround Sound (e.g. External Emitter/Receiver (Detachable), Receiver (Integrated), Amplifier (Integrated), Speakers (Integrated), Microphone Jack (Integrated), Microphone (Detachable), Transmitter/Audio Out (Detachable))), and a Power Regulator (e.g. Power Plug (Detachable), Power Transformer (Detachable), Charger/Power Receiver (Integrated), Wiring to all of the necessary components to power all the components of the Exoskeleton via the activation of the Receiver(s) (Integrated), Power Cell (Detachable)).

For an Exoskeleton to work with any other platform the development of a new Decoder, Surround Sound External Emitter/Receiver and Surround Sound Transmitter/Audio Out may require some alterations. All of which are detachable components to allow the Exoskeleton to remain universal.

The Control Centre may be operable for updates or alterations in parallel with other component updates, software updates and patches, and hardware system changes. The Nervous System may be operable for alteration and advances of current components, creation of new components i.e. constriction/compression, force/physics, air. The Power Regulator may be operable for consumption efficiency, power reduction, power weight, power Placement. The exoskeleton may include a variety of design modifications including placement and specifications of its components, creating an Exoskeleton for particular niche markets, modular design for the Exoskeletons, variants in different sizes and for different sexes, and so on.

Figure 17A:
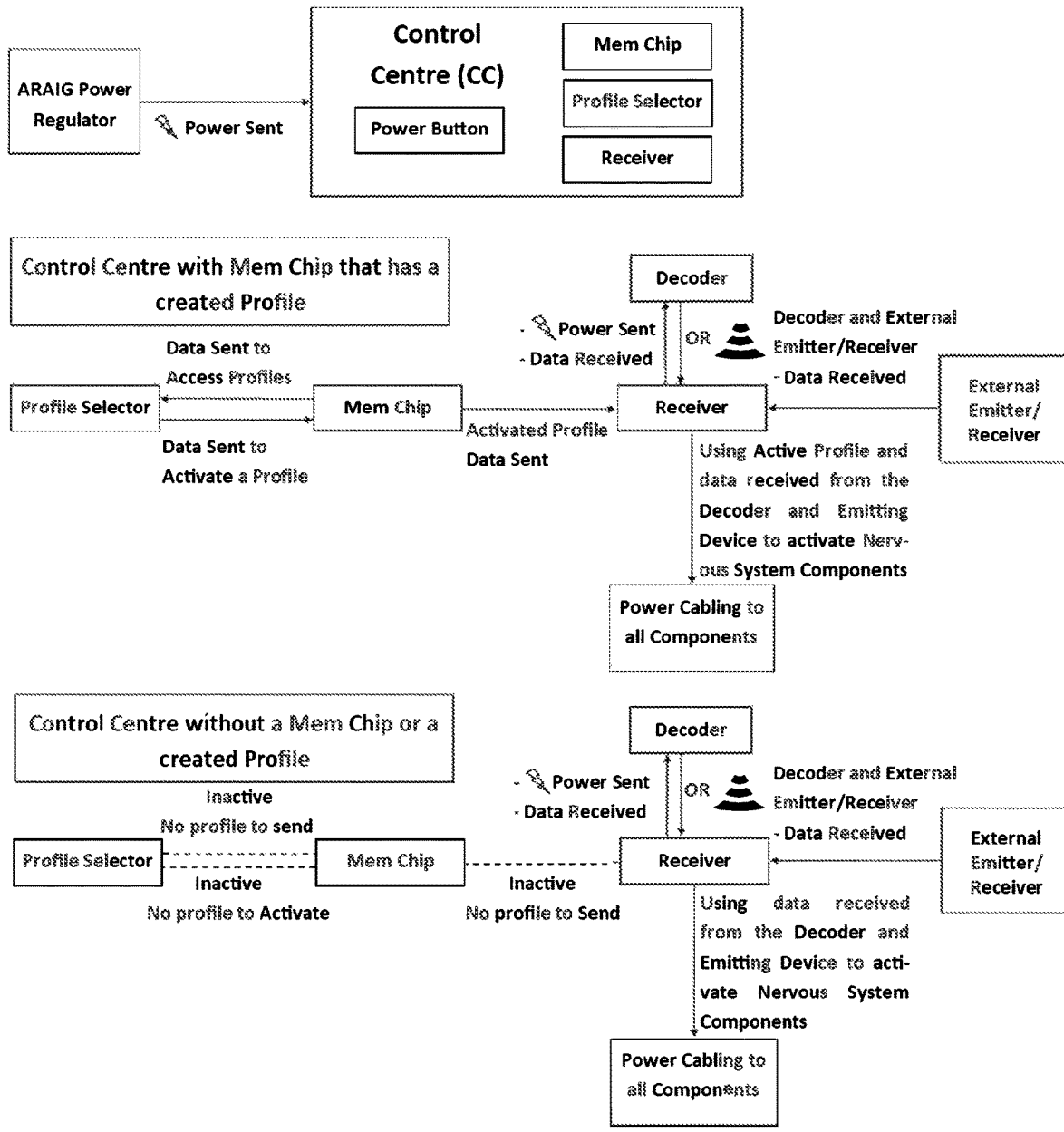
FIGS. 17a and 17b illustrate Control Centre specifications according to some embodiments.
Figure 17B:
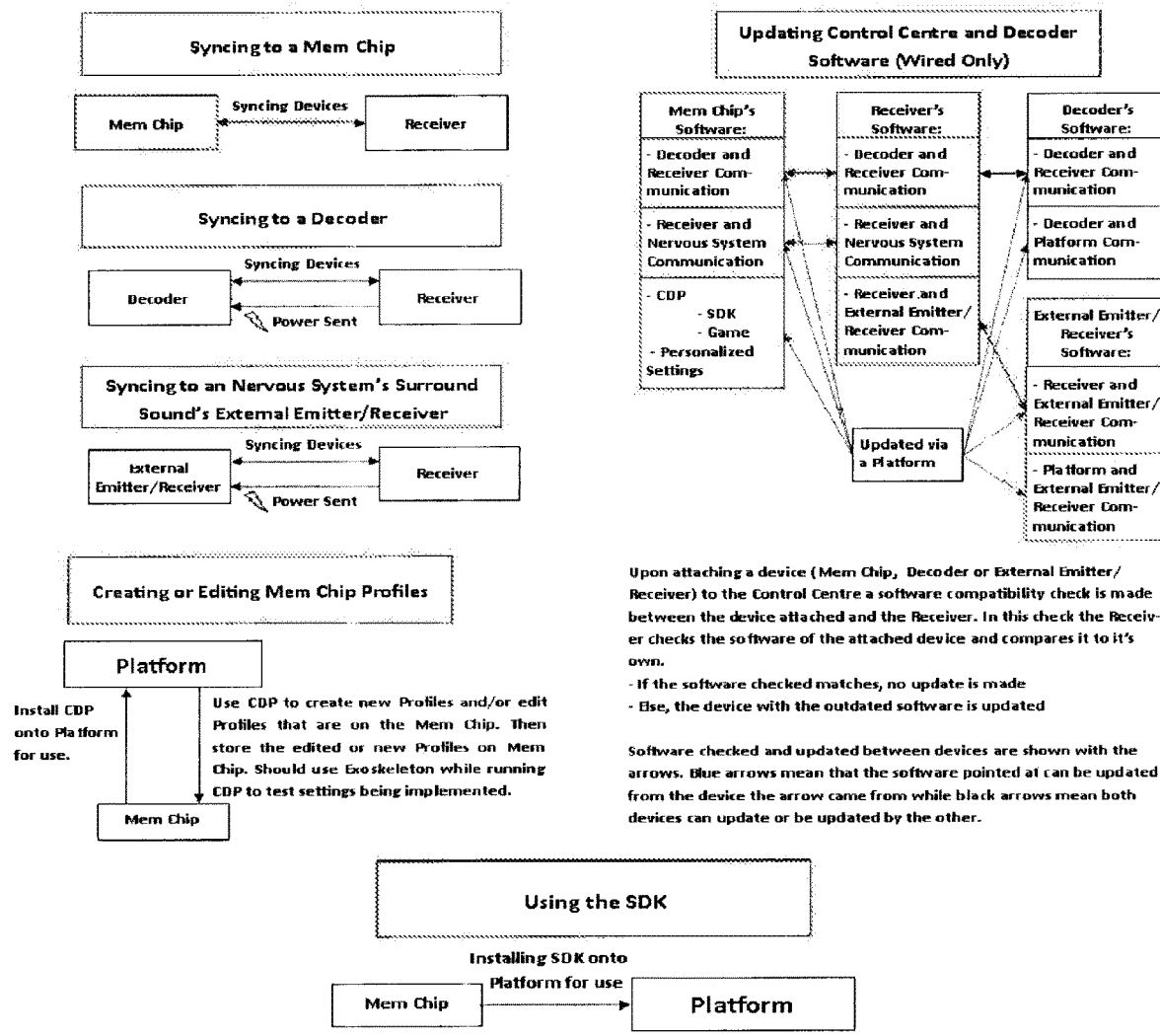

FIGS. 17a and 17b illustrate Control Centre specifications according to some embodiments.

A Control Centre may have a Power Button which is capable of turning the Exoskeleton on and off to receive power from a Power Regulator. A Control Centre may have a Mem Chip which has the CDP (Calibration Diagnostic Protocol), Personalized Settings, Decoder and Receiver Communications, and Receiver and Nervous System Communication Software. The CDP is able to install/download the SDK onto the computing device for use and the game or other software onto various platforms. The SDK allows developers to easily program, test and integrate the system into their software. The Game or other software may allow a wearer of an Exoskeleton to properly adjust the profile settings and create multiple profiles to have different types of immersive experiences. The personalized setting can be adjusted on computing device through the Game. A Mem Chip may be able to receive software updates via a platform (e.g. computing device) and from the Control Centre. A Mem Chip may be able to update the Control Centre software if outdated. Mem Chip may attach, sync and communicate with devices via USB.

A Control Centre may have a Profile Selector which is able to go through the various saved profiles on an attached Mem Chip. Upon selecting a profile, a Profile Selector may have sensory feedback that specifies the one selected. A Profile Selector may have the Mem Chip send the selected profile to the Receiver.

A Control Centre may have a Receiver which has the CDP, Personalized Settings, Decoder and Receiver Communications, and Receiver and Nervous System Communication Software. Using the Decoder and Receiver Communication software, the Control Centre may be capable of receiving the raw non-audio sensory activation data from the Decoder. Using the Receiver and External Emitter/Receiver Communication software, the Control Centre may be capable of receiving the raw audio activation data from the External Emitter/Receiver. Using the Receiver and Nervous System Communication software, the Control Centre may be capable of taking the received data from the Decoder, External Emitter/Receiver and Mem Chip active Profile to activate the appropriate Nervous System components at the proper intensities and locations. The Control Centre may be able to receive software updates via a Mem Chip, Decoder and External Emitter/Receiver. Also able to update the software of Mem Chip, Decoder and External Emitter/Receiver.

In example embodiments, the Control Centre may have three USB ports to attach a Mem Chip, Decoder and Surround Sound External Emitter/Receiver for syncing and wired data transfer. Which USB port is used by each detachable device may not matter.

In example embodiments, the Control Centre may have a wireless receiver to be able to receive data wirelessly from a Decoder.

In example embodiments, the Control Centre may have a wireless receiver to be able to receive data wirelessly from Surround Sound External Emitter/Receiver.

In example embodiments, the Control Centre may have Activate all the needed nervous system components based on the data it receives from the Decoder and Surround Sound.

In example embodiments, the Control Centre may need to be integrated into the exoskeleton in such a way that it does not restrict movement and that it is easily accessible to add or remove any of its detachable components (Mem Chip) or components that can be attached to it (Decoder and Surround Sound External Emitter/Receiver) without the wearer having to take off the Exoskeleton.

In example embodiments, the Control Centre may be removable and replaceable for defect or upgrade or fixing, and so on Transmitter/Audio Out component currently may be part of the Nervous System Surround Sound or built into the Control Centre. It may be a detachable component of the Control Centre.

In example embodiments, the Control Centre may have wireless transmission protection from Decoder to Receiver and wireless transmission interference reduction.

The Power Button is the component to turn on the ARAIG Exoskeleton. Once on, the Control Centre will be able to function as described in each of its components and power will be able to flow throughout the Exoskeleton as required.

Mem Chip may be a detachable component of the Control Centre and may be a USB design for each of use in data storage and transfer. Mem Chip may contain the needed Calibration and Diagnostics Protocol (CDP) for creating profiles on various platforms. While creating a Profile on a given Platform the Mem Chip may be physically attached to the platform to receive the edited or new profile and not the Control Centre. To use the profiles stored on the Mem Chip the Mem Chip may be attached to the Control Centre Receiver and the profile must be selected by the Profile Selector.

The SDK software on the Mem Chip can be installed/downloaded onto various platforms for use by developers to properly integrate ARAIG into the own software.

Profile Selector may be a component of the Control Center that allows an individual to cycle through their created profiles via physical inputs. If they do not have a Mem Chip attached or they have no profiles it is inactive. If there are any profiles then by default it activates the newest profile when the Control Centre is powered on. Afterwards a user can cycle through the profiles and select a different profile to activate. Each profile may be saved with sensory feedback so the user can easily differentiate between the profiles while searching.

Receiver is a component that has a receiver to pick up wireless transmissions from any Decoder or Nervous System Surround Sound External Emitter/Receiver. Receiver is the component that is directly connected to by a wired Mem Chip, Decoder and/or External Emitter/Receiver through ports (e.g. 3, USB) and has software to use the synced Mem Chip profiles, Decoder date and External Emitter/Receiver data to activate the necessary Nervous System components.

FIG. 18 illustrates nervous system specifications for power activation according to some embodiments. This illustrative example may help visualize the flow of power to the Nervous system as a whole.

Figure 19:
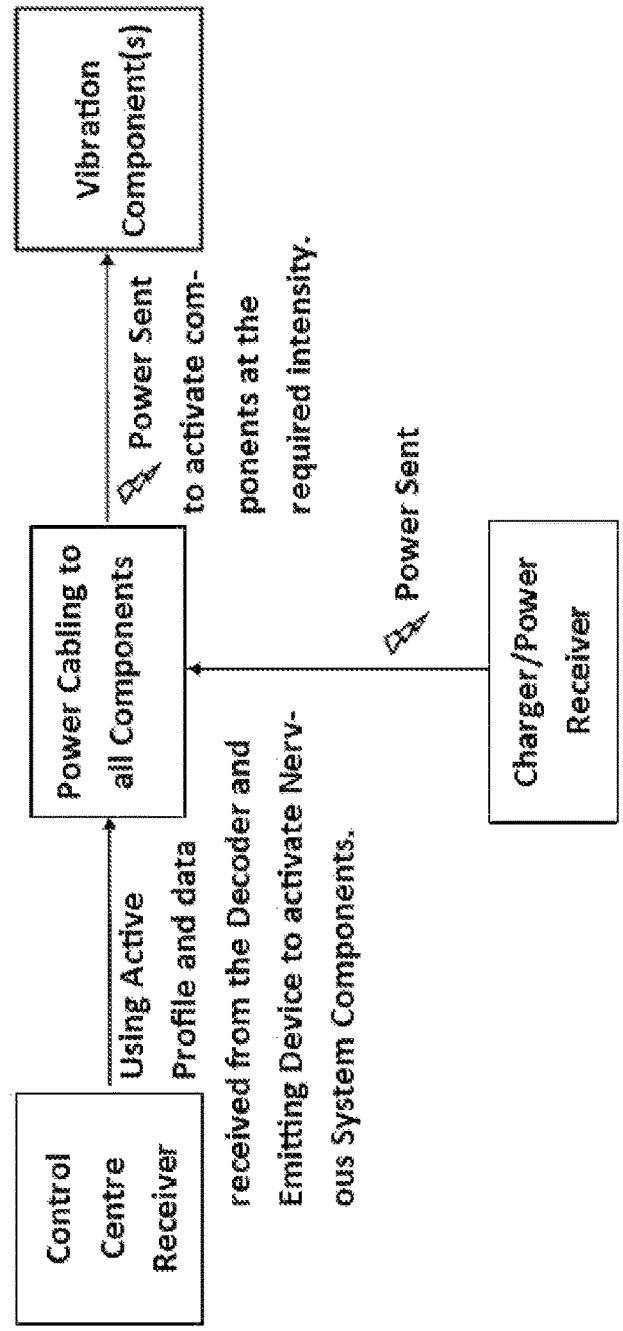
FIG. 19 illustrates nervous system specifications for vibration according to some embodiments.
Figure 20B:
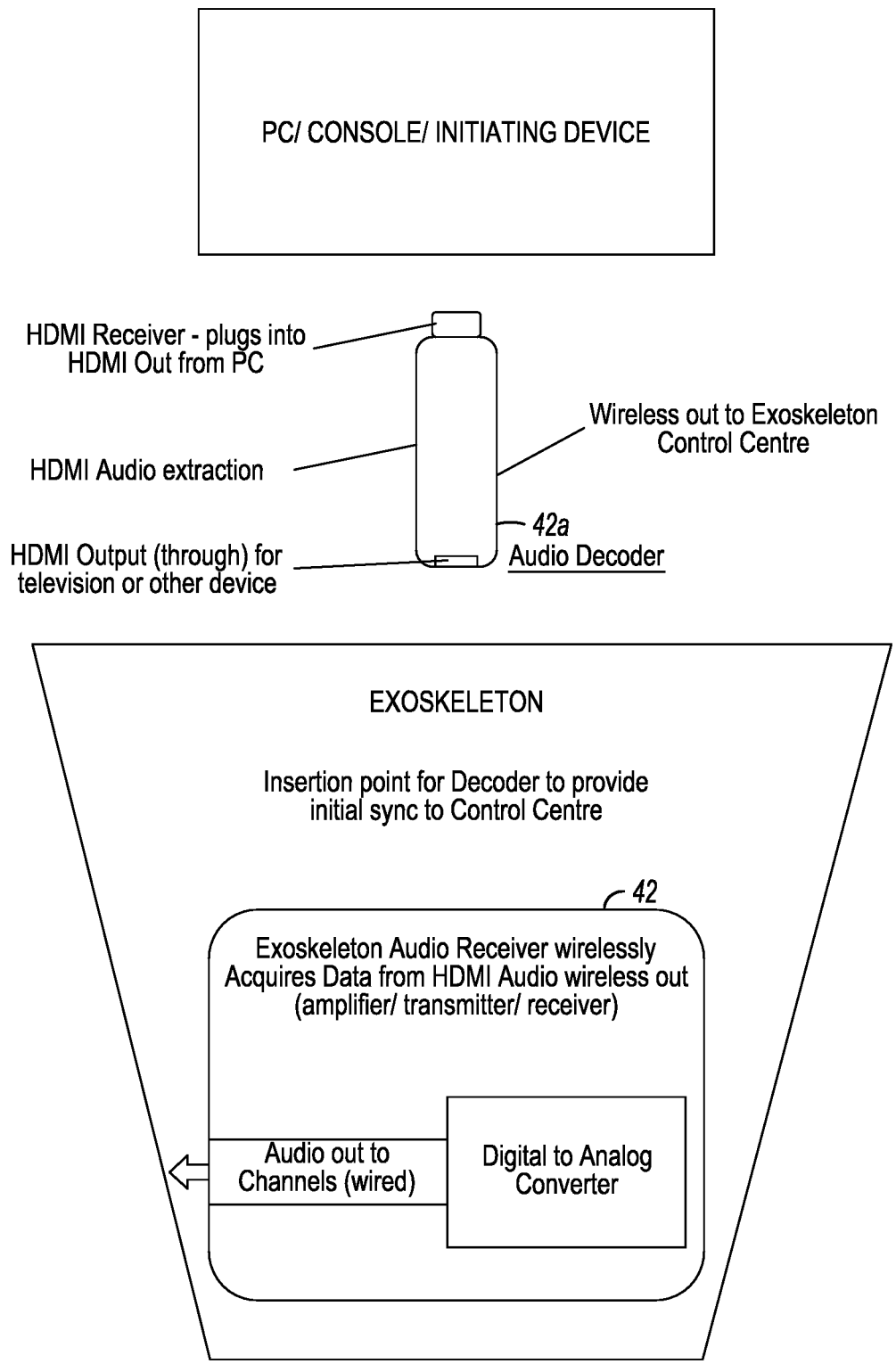

FIG. 19 illustrates nervous system specifications for vibration according to some embodiments.

In example embodiments, the Nervous System vibration device may include enough vibratory stimuli to have a coverage area of the torso front and back, shoulders and upper arms. The amount of vibratory stimuli required to do this may be determined depending on application and field of use. In some examples there may be a minimum of 16 front, 16 back, 8 left should/upper arm and 8 right shoulder/upper arm; total of 48 points; although most important factor is coverage over amount of stimuli. This is a non-limiting example.

Each vibratory stimulus may be able to create different ranges of intensity from a small vibration to an intense shaking sensation in their own location.

Each vibratory stimulus may be able to activate individually, sequentially of other vibratory stimuli or sensory feedback devices, or simultaneously of vibratory stimuli or sensory feedback devices; all of which can also be for different durations and different coverage areas.

The nervous system may be programmed with algorithms created to give sensations such as a single location, multiple locations, a region, expansion or contraction of impact in an area, vibration in a line all at once or in sequence and a wave sensation; all at varying intensity and duration.

The activation of a vibratory stimulus will not cause interference with the activation of other stimuli; such as other vibratory stimuli, STIMS or Surround Sound.

Different embodiments may have variation of placement, intensity, duration and type of vibratory stimuli. Different embodiments may consider user's ability to localize such sensations and what the sensations feel like to them. Different embodiments may have different updates to algorithms to create a variety of sensations. Different embodiments may use a device that is compliant with all standards but specific to a field of use; may create several variations depending on market niche.

Vibration Components are the multitude of vibratory stimuli devices that are integrated throughout the Exoskeleton. Each vibration device is capable of working at various intensities to create different vibratory sensations.

A coverage area that an individual should feel the vibratory stimuli may be the torso front and back and the upper arms and shoulder areas of the Exoskeleton. The amount of vibratory stimuli devices to cover these areas may allow for an individual to feel both localized sensation and moving sensations from one vibratory stimuli device to one or more other vibratory stimuli devices.

FIGS. 20a to 20d illustrate nervous system specifications for surround sound according to some embodiments.

In example embodiments, Nervous System surround sound sensory devices may include an External Emitter/Receiver Component or Audio Decoder 42a capable of receiving Audio Output from the computing device and send it to one or more Exoskeleton's that are synced to receive the data from this External Emitter/Receiver. The Emitter/Receiver Component may be synced with Surround Sound Receiver(s) or Control Centre Receiver(s) for one or more Exoskeletons to receive the Audio data. Emitter/Receiver Component may receive the data directly from the External Emitter/Receiver. Emitter/Receiver Component may be able to receive software updates via a platform computing device and from Control Centre Receivers; also enabling the update of the software of the Control Centre Receiver if its software is outdated. Emitter/Receiver Component may update and be updated by a Control Centre Receiver if the Control Centre Receiver is the device that has been determined during development to sync with the External Emitter/Receiver. Emitter/Receiver Component may be wired to directly to receive Microphone Audio from the Exoskeleton via the Transmitter/Audio Out and thus would be wired to a platform to send the Microphone Audio to it. Emitter/Receiver Component may receive its power from the platform or Exoskeleton when syncing.

In example embodiments, Nervous System surround sound sensory devices may include a Receiver. It takes the Audio Output of an initiating device wirelessly from Emitter/Receiver or Audio Decoder via wifi, Bluetooth, radio, etcetera, The receiver may translate the digital data to analogue and send it to the amplifier.

In example embodiments, Nervous System surround sound sensory devices may include an Amplifier that takes audio data from the Receiver and distributes it appropriately to the various speakers located on the Exoskeleton.

In example embodiments, Nervous System surround sound sensory devices may include Speakers. The exact angle and positioning of the speakers may be dependent on the field of use and application.

In example embodiments, Nervous System surround sound sensory devices may include a Microphone as the Audio Input device for the wearer of the Exoskeleton and a Microphone Jack that can be used to attach a microphone and sends Microphone Audio to the Transmitter/Audio Out component.

In example embodiments, Nervous System surround sound sensory devices may include a Transmitter/Audio Out that receives the Microphone Input and sends it either wirelessly to a platform or wired or wirelessly to the External Emitter/Receiver. This piece may be built into the Control Centre instead should that be decided during development.

In example embodiments, Nervous System surround sound sensory devices may include variations on placement, volume and speaker quality based on a user's ability to localize sound, for example. In example embodiments, Nervous System—Surround Sound may include updates to algorithms to transfer sound effectively between speakers.

External Emitter/Receiver is a device that may not be integrated into the Exoskeleton. To use, it may be wired to a particular platform to receive the audio output from the connected platform and in specific circumstances receive microphone audio input from a Transmitter/Audio Out. When the audio output is received from a platform it is sent out to one or more Exoskeletons' Receiver that has been synced with the External Emitter/Receiver. To sync a Receiver to an External Emitter/Receiver the Emitting Device needs to be wired to the Receiver. Once synced the Receiver will be able to receive the data output from the Emitting Device. The Emitting Device receives its power from the platform or Receiver that it is attached to.

The Emitting Device may Sync with the Control Centre's Receiver rather than the Nervous System's Surround Sound's Receiver and the Control Centre would then send the data to the Nervous System's Surround Sound Receiver. This may be implemented during the development process. With that stated it would also allow the Mem Chip to set the Surround Sound settings which in turn would maintain a consistent flow of external data to Control Centre to Nervous System Activation.

Receiver is the component that receives the data from a synced Emitting Device and sends the data to the Amplifier(s).

Amplifier is the component that receives data from the Receiver to activate the appropriate speaker(s) to play the proper localized sound for the wearer.

Speakers are the multitude of sound components that create the localized audio for the user. The placement of the speakers creates the surround sound effect. The speakers that are activated and the sound that is created from each speaker is de pendent on the data that is received from the Amplifier(s).

Microphone is a detachable component that the user will use to input audio into an Exoskeleton's Nervous System via a Microphone Jack to be used by other systems or Exoskeleton's as audio output.

Microphone Jack is the component that allows a user to connect any microphone they would like to use for audio input. Upon receiving audio input from a Microphone the data is sent to the Transmitter/Audio Out to be sent out for use by other systems (Platforms and External Emitter/Receivers).

Transmitter/Audio Out is a detachable component that will receive audio input from the Microphone Jack and send the audio input to a platform or device that has been synced wired or wirelessly to be used as audio output. As the wireless and wired transmission to each platform could differ there will be a variety of Transmitter/Audio Outs for the various platforms.

The Control Centre may have the Transmitter/Audio Out component attachable to it. Thus, the Microphone Jack may send the Audio input from the Microphone to the Control Centre's Transmitter/Audio Out device to send out to the particular systems (Platforms and External Emitter/Receivers).

Figure 21:
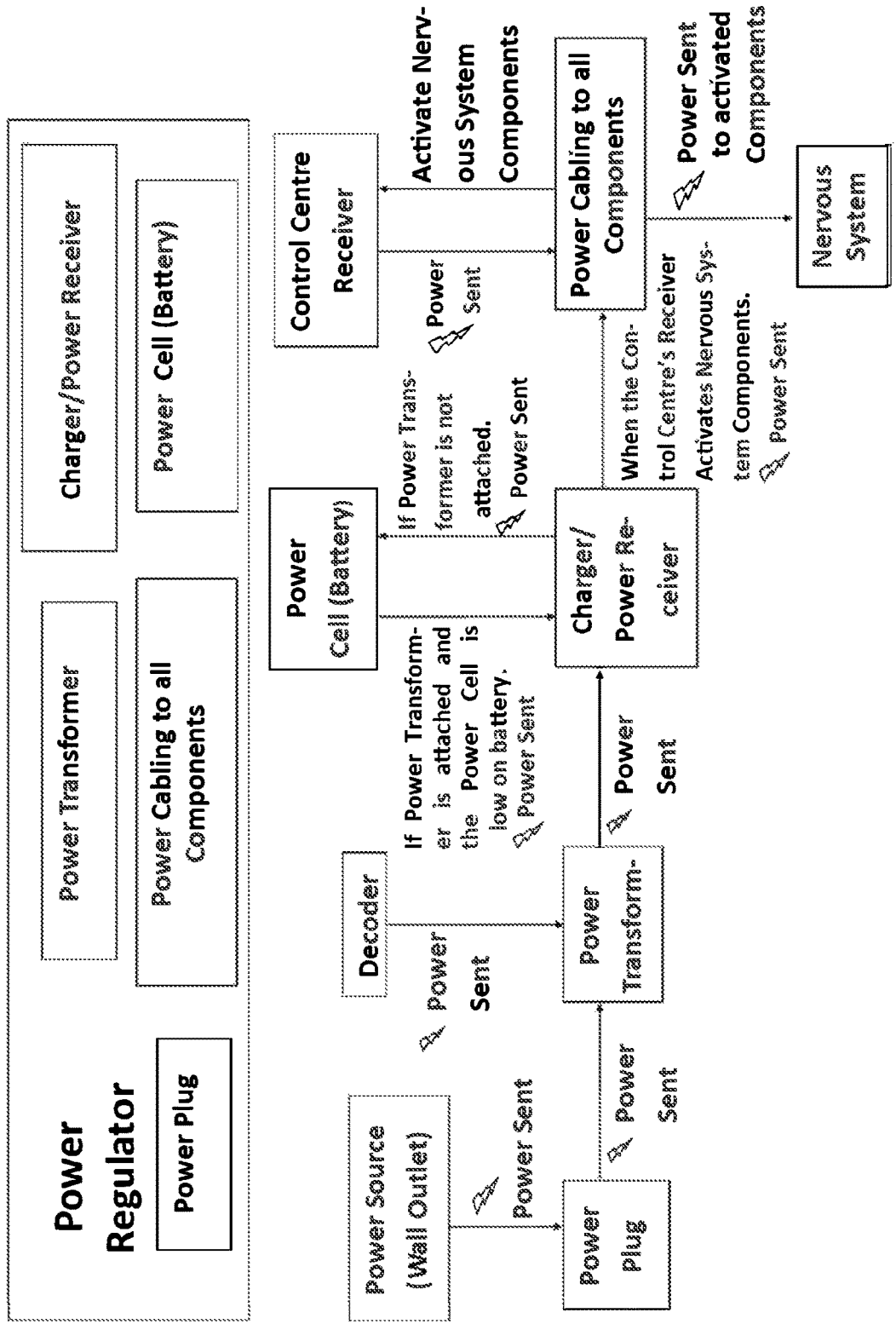
FIG. 21 illustrates power regulation specifications according to some embodiments.

FIG. 21 illustrates power regulation specifications according to some embodiments.

In example embodiments, Power Regulator may include a Power Plug that can be used with wall outlets and capable of plugging into a Power Transformer to send power to various components.

In example embodiments, Power Regulator may include a Power Transformer as a universal power receiving device to convert the power to the appropriate amount to power an Exoskeleton, Power Cell and Decoder individually, several, or all need simultaneously without affecting the use of the other devices. This may be plugged into by any Power Plug designed for the system no matter the Power Plugs specifications to a particular countries wall outlet power output, for example.

In example embodiments, Power Regulator may include a Power Cabling to All Components via integrated wiring connecting all components to power entire Exoskeleton system. There may be power through cabling is controlled by the Control Centre Receiver.

In example embodiments, Power Regulator may include a Charger/Power Receiver that is able to distribute the needed power to all components of an Exoskeleton and a Power Cell Simultaneously. This may be able to use an attached Power Cell to distribute the needed power to all components of an Exoskeleton Simultaneously, and be able to receive power from a Power Transformer for wired use. This may be built into the exoskeleton in such a way that it does not restrict movement and that it is easily accessible to plug in the Power Cord and remove/replace/attach a Power Cell by the wearer without having to take off the Exoskeleton.

In example embodiments, Power Regulator may include a Power Cell developed or acquired the needed battery to provide an Exoskeleton with a reasonable battery life. When attached to the Exoskeleton's Charger/Power Receiver the Power Cell may be able to provide power to the Exoskeleton or be charged by a power Transformer attached to the Charger/Power Receiver.

In example embodiments, Power Regulator may include a standalone multi battery charger developed or the specifications determined for manufacture of such a device.

In example embodiments, Power Regulator may include power reduction and power efficiency mechanisms.

Power Plug is a component to supply the Power Transformer with power through a wired connection. There may be several Power Plug variants to deal with the different electrical power systems and their outputs as they vary from country to country.

Power Transformer is a component that takes the power it receives from the Power Plug and ensures it meets the needed power requirements to charge and/or power the ARAIG Suit and its components. It also can be directly plugged into by the Decoder to be used as the Decoder's external power source.

Charger/Power Receiver is a component that powers the ARAIG suit and its components. It receives its power from the Power Transformer or a Power Cell (Battery). If there is no attached Power Cell it receives its power from the Power Transformer. If there is a Power Cell attached and no Power Transformer attached it receives its power from the Power Cell. If a Power Cell and Power Transformer are attached it receives its Power from the Power Transformer and diverts energy to charge the Power Cell until it is fully charged by the Power Transformer. Which nervous system components are activated and at what intensity they are activated are dependent on what the Control Centre Receiver allows to be activated; the Charger/Power Receiver supplies the power for the specifics to occur.

The Charger/Power Receiver can recharge a Power Cell without the Exoskeleton being turned on.

Power Cabling to all Components provides the wiring to give all the components of the exoskeleton power and indirectly a wired Decoder power through the Control Centre. When the Exoskeleton is powered on, the Control Centre is the only component that the Power Cabling to all Components that is always powered on.

Power Cell (Battery) is a detachable component that allows the Exoskeleton to be wireless. When attached to the Charger/Power Receiver it can give the Exoskeleton the needed power to operate. It can also be recharged directly through the Charger/Power Receiver if the Charger/Power Receiver is receiving power from the Power Transformer instead.

Figure 22:
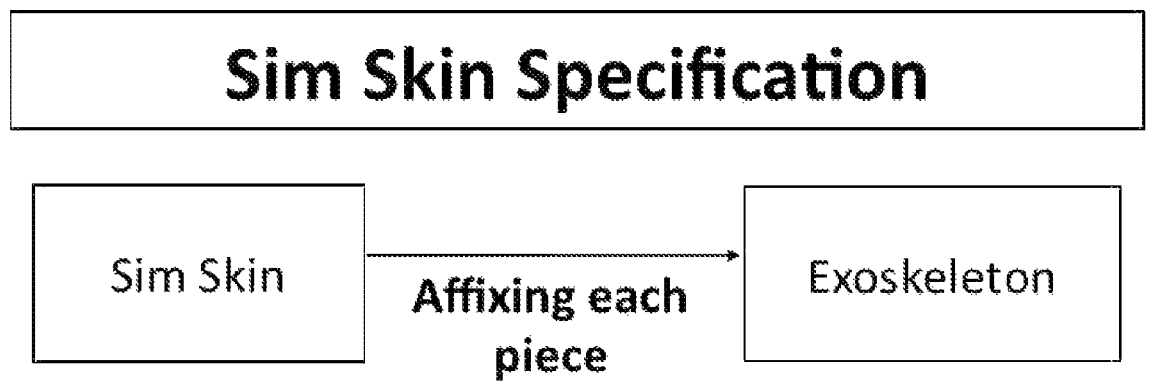
FIG. 22 illustrates wearable material specifications according to some embodiments.

FIG. 22 illustrates wearable material specifications according to some embodiments.

The wearable material may be referred to as "sim skin", for example.

The Sim Skin may cover the majority of an Exoskeleton's Torso front and back, shoulders and upper arms (e.g. 4 to 6 separate pieces). Sim Skin components may be designed specifically for males or females, and some components may work for both males and females (e.g. varying sizes, while some will be used only by a particular gender). The Sim Skin may be affixed to an Exoskeleton. The components to affix the Sim Skin components to the Exoskeleton may blend with the aesthetic look and design or may be able to be easily hidden while the Exoskeleton is worn. The Sim Skin may not hinder or negatively affect the wearer's mobility, comfort, ergonomics or functionality of the suit. There may be different sizes or a one size fits all.

Sim Skin design may allow the Sim Skin Torso component(s) to be affixed or removed without the wearer having to take off the Exoskeleton. Furthermore, if possible the Sim Skin components may allow easy access to the Exoskeleton detachable and interactive components without removal of the Sim Skin components or with only partial removal of one or more of the Sim Skin components so that the wearer does not have to take off the Exoskeleton. There may be alternative colours, designs, materials, components, accessories/attachments. There may be increased modular design for the Sim Skins, such as possible Female, Male and Unisex Sim Skin components and sizes.

Each Sim Skin may have several aesthetic components. These aesthetic components are affixed on top of an Exoskeleton to create a particular look. Components from several Sim Skin's can be affixed to an Exoskeleton to give users an even more unique look. Each of the pieces cover a different portion of the Exoskeleton; such as the front and back of the torso and each shoulder/upper arms. Although, the exact coverage, placement and number of components will be dependent on the most effective design to do so.

The number of components may be determined through the development of the Sim Skins but there needs to be enough components to cover the majority of the front and back of the torso, and each shoulder/upper arm without hindering or negatively affecting the wearer's mobility, comfort, ergonomics or functionality of the other ARAIG components, especially the Exoskeleton.

The components of the Sim Skin that affix each piece to the Exoskeleton if visible need to match the aesthetics of the Sim Skin and/or that of the Exoskeleton. Otherwise if the components of the Sim Skin that affix to the Exoskeleton are able to be hidden easily it does not matter. A Sim Skin can be easily attached to or taken off by easy to use components for affixing the Sim Skin to the Exoskeleton.

Figure 23:
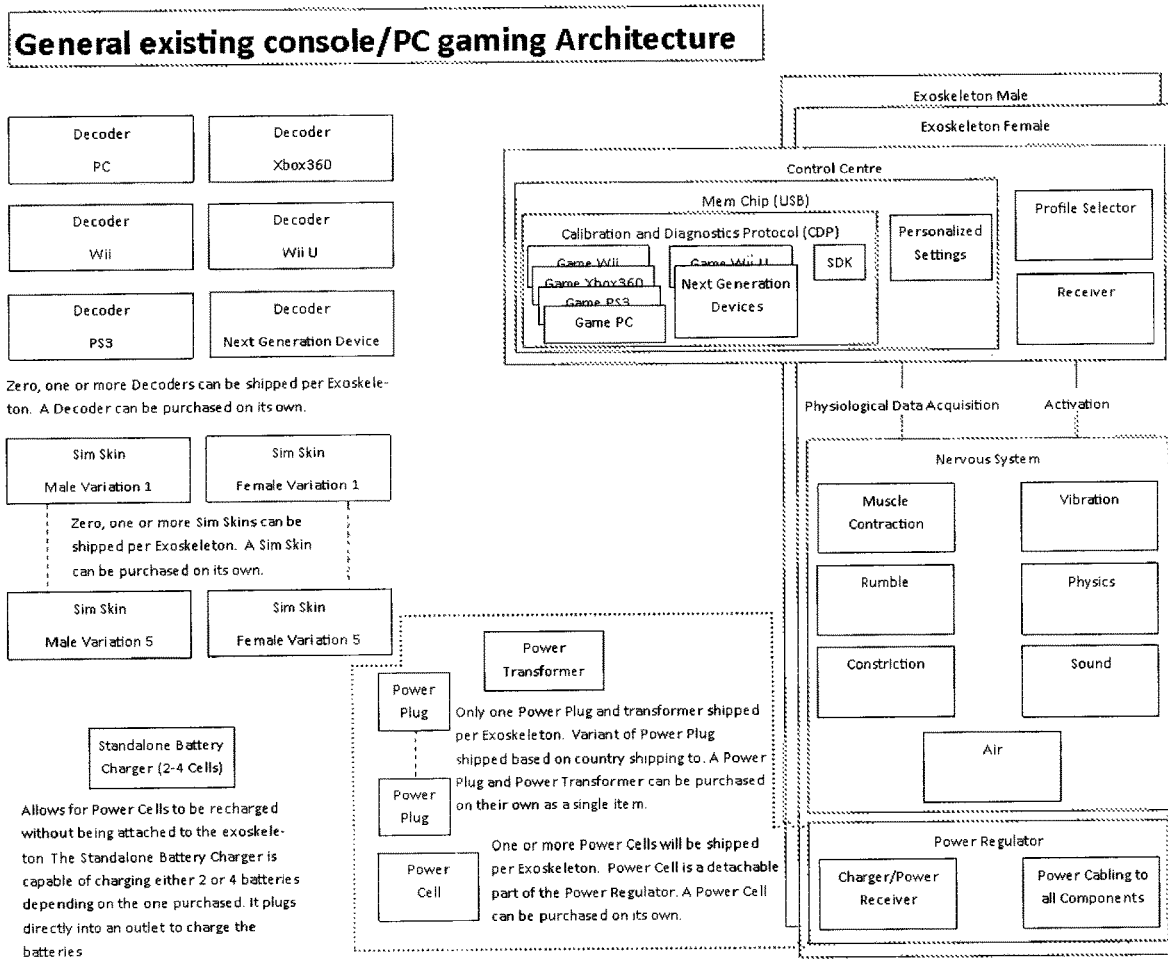
FIG. 23 illustrates an example gaming console architecture according to some embodiments.
Figure 27:
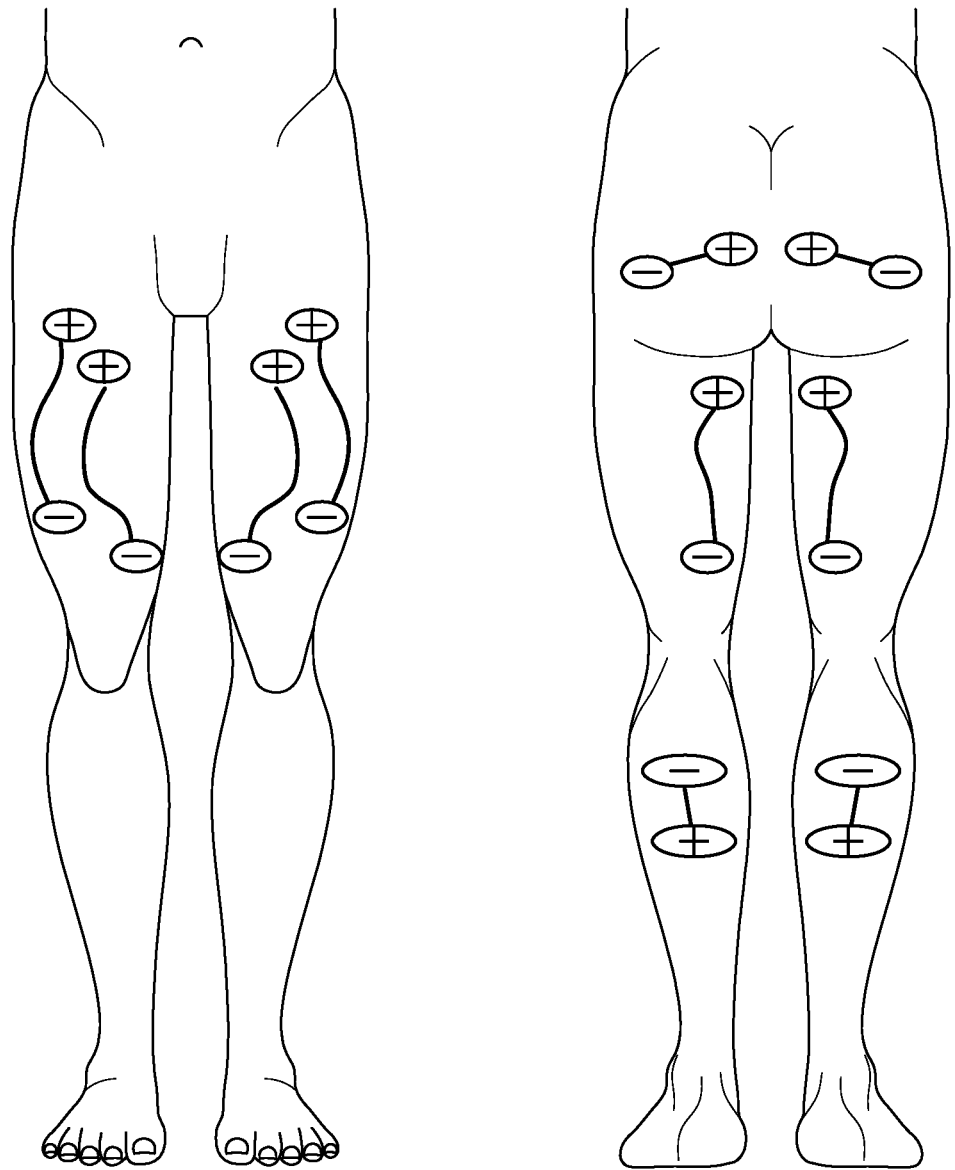
Figure 30:
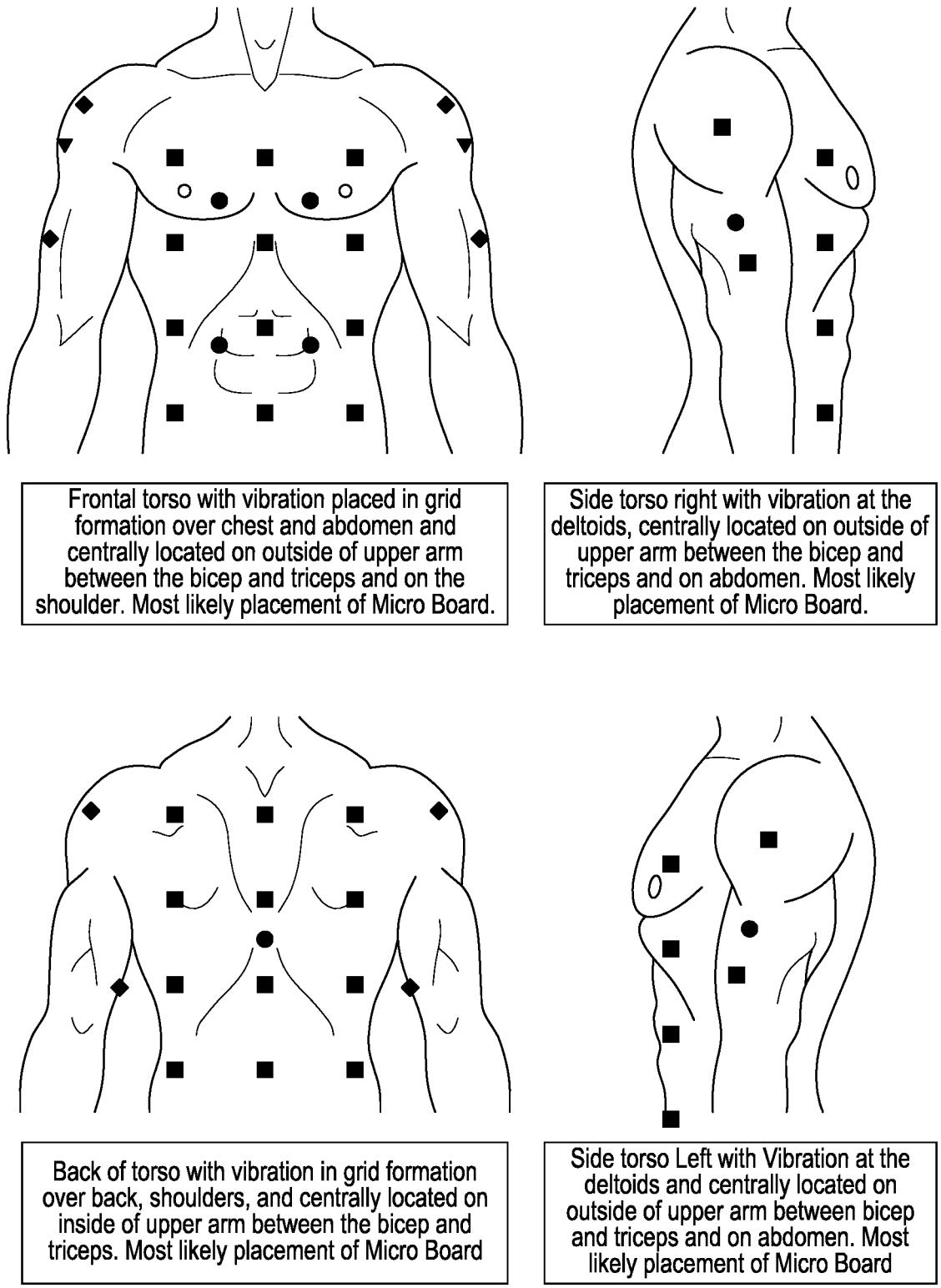
Figure 31:
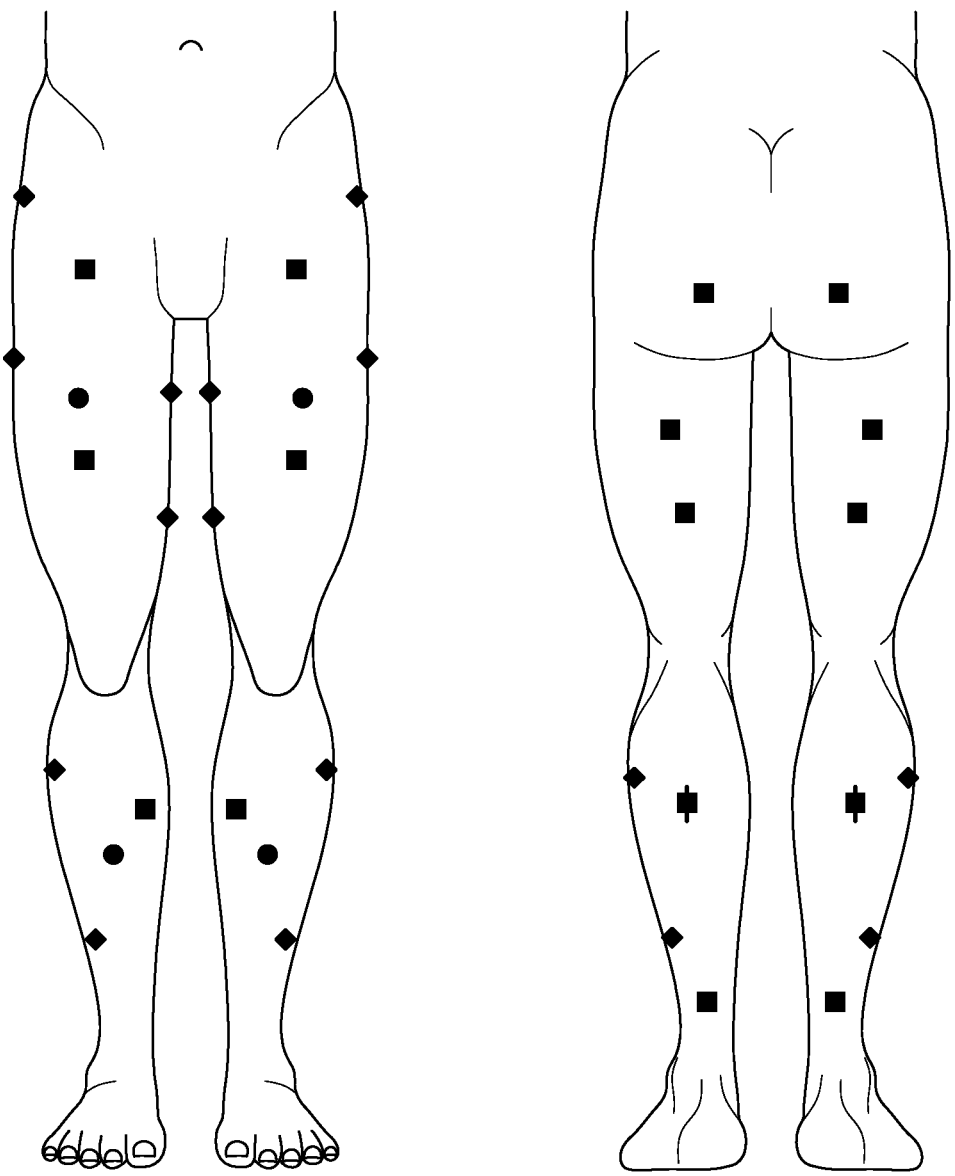
Figure 33:
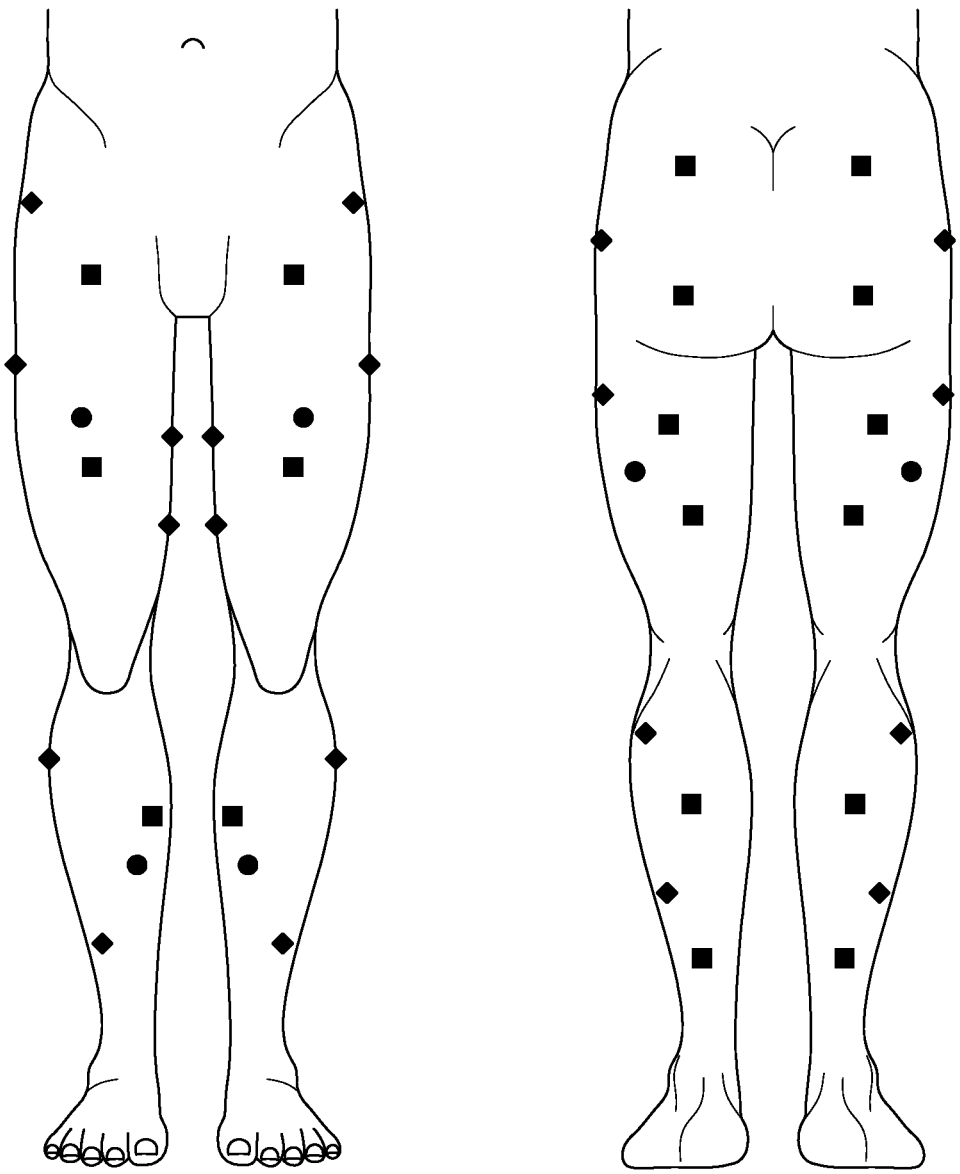
Figure 34:
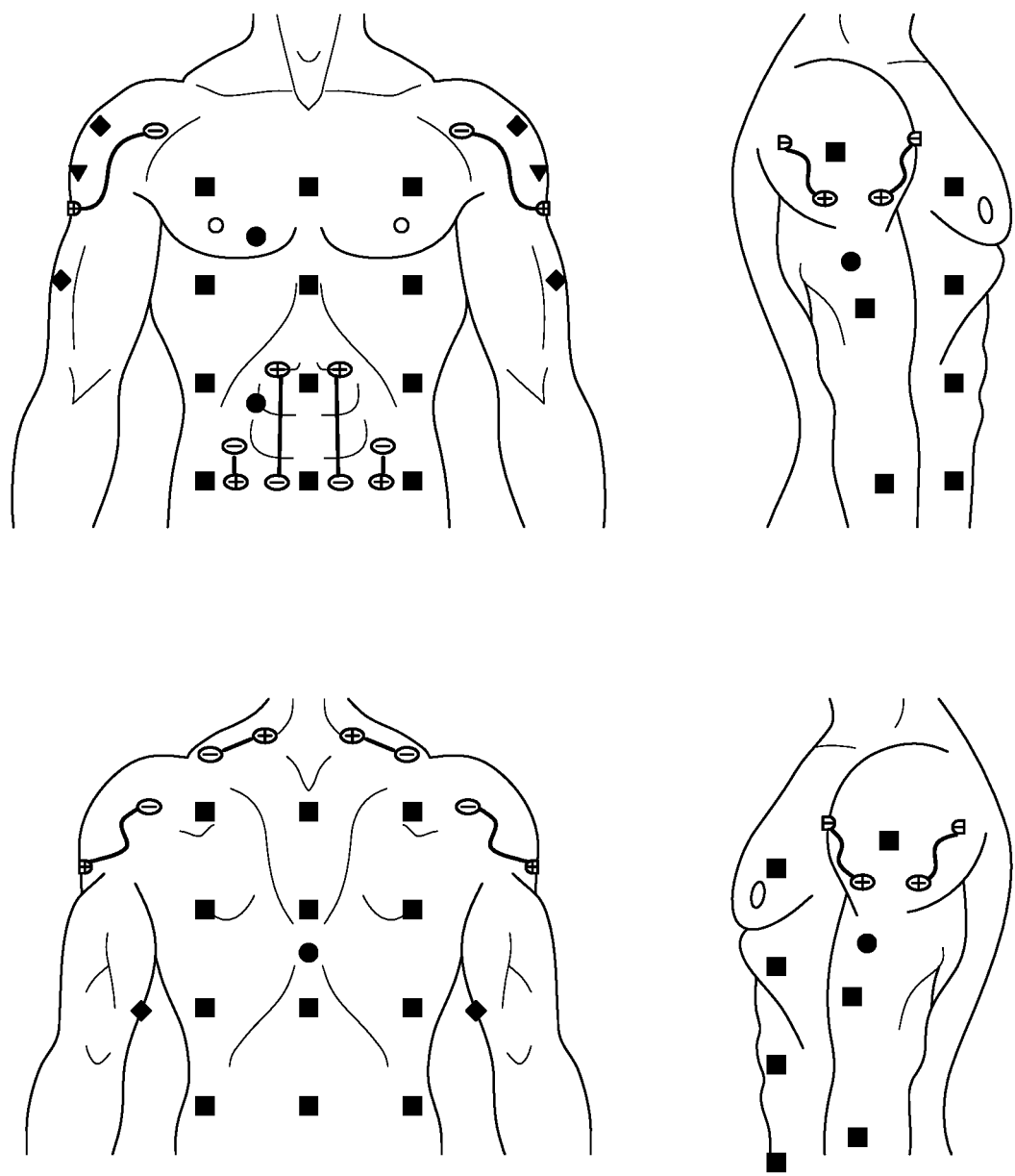
Figure 35:
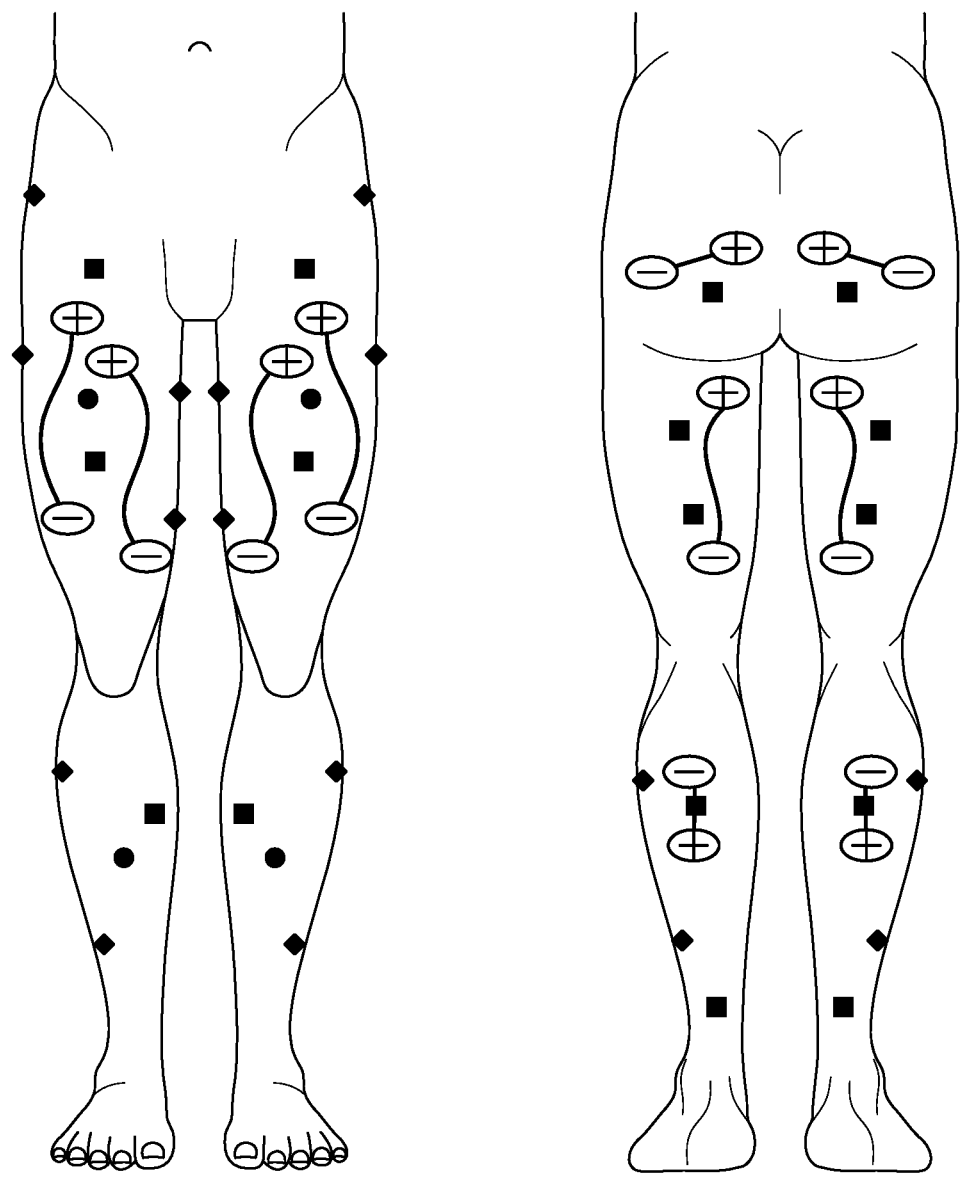
Figure 36:
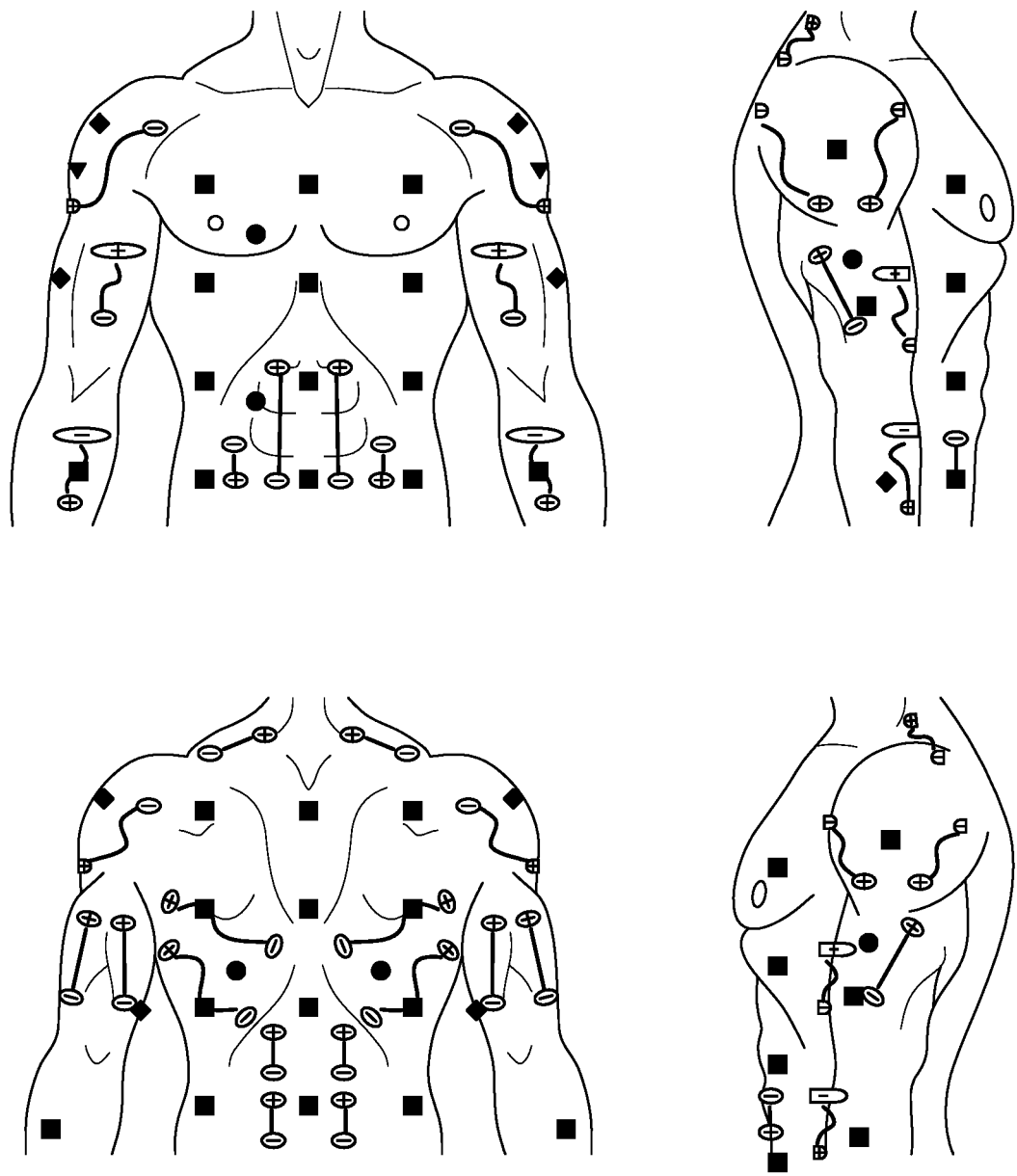
Figure 37:
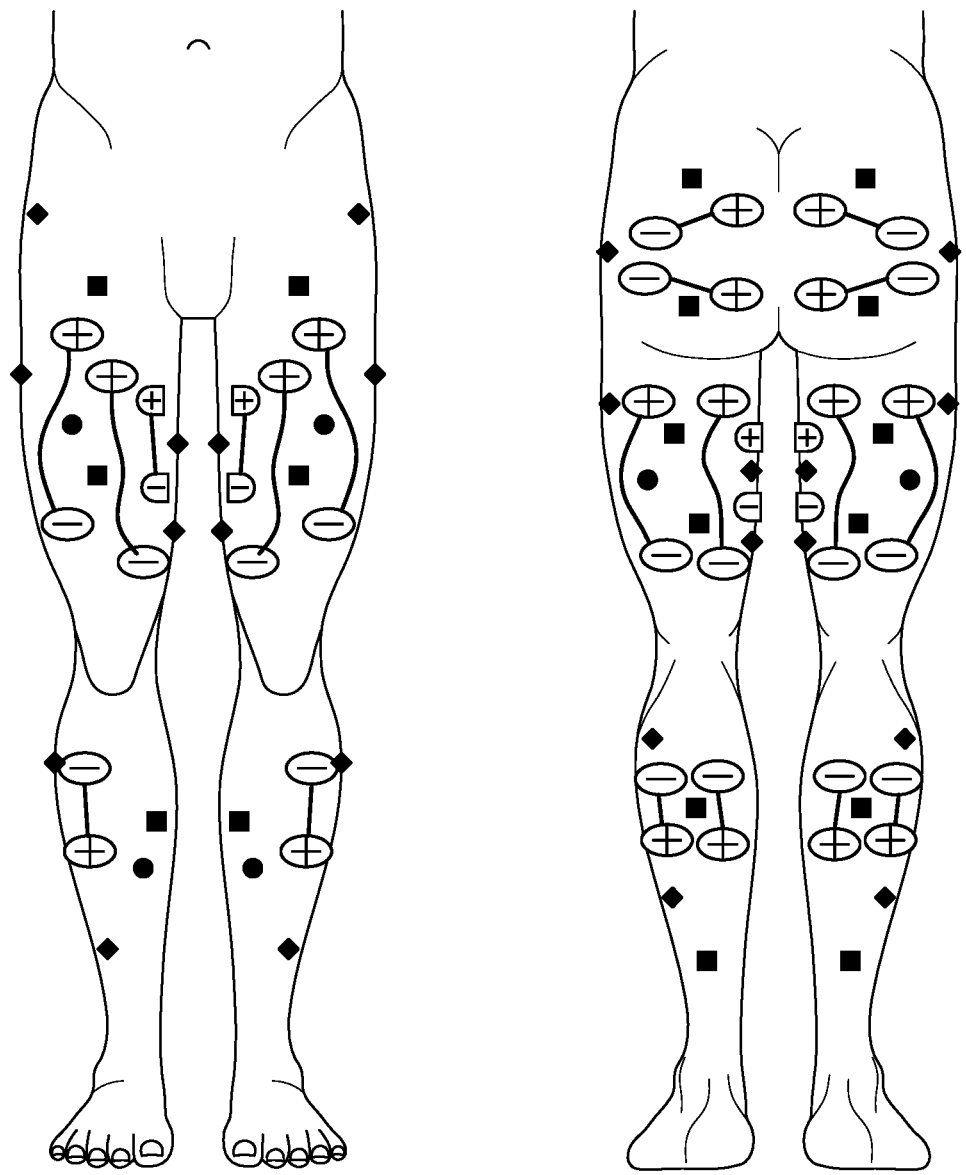

FIG. 23 illustrates an example gaming console architecture according to some embodiments.

FIG. 24 illustrates example nervous system STIMS specifications. The STIMS includes MCEIAs and paired electrodes.

Medically Compliant Electrical Impulse Amplifier(s) (MCEIA(s)) are the components that provide stimulation to a user's tissue, nerve and or muscle through electrical energy. They are medically compliant in their activation protocols and limitations and adhere to US FDA, Canadian, and European standards for such devices. The MCEIAs receive the necessary power from the Exoskeleton to send the needed signal to one or more Paired electrodes to stimulate the user's physiology.

The amount of MCE IA devices required in the Exoskeleton may be dependent on the amount of locations that one MCE IA can effectively provide stimulation simultaneously without compromising the effects that one location can receive and still being able to adhere to the activation protocols, limitations and standards across different nations.

Each Paired Electrode is integrated throughout the Exoskeleton. Each Paired Electrode receives the necessary power to send and receive through the attached Electrode Pads.

There may be four Paired Electrodes of which two pairs may be used to cover the abdomen area while another two may be place to cover the shoulder to chest area. The addition, removal or altering of the placements is possible.

Each Electrode Pad is attached to an Electrode. For every pair of electrodes the user places the Electrode pads onto a single muscle. When the Electrode Pads receive power the muscle they are attached receives a particular electrical stimulation.

FIGS. 25 to 37 illustrate Sensory Device placement for example embodiments. FIG. 25 provides a legend for the symbols used in FIGS. 26 to 37. These are examples and other placements may be used for the Sensory Devices for various Sensory Stimulations.

The application of this wearable technology as activated through a virtual medium or device, in that the virtual medium or device is what determines how the device interacts with the individual attached to the device, allows for consistency in Sensory Manipulation. Furthermore, this approach of the described technology is inventive as it allows virtual mediums to effectively create Sensory Outcomes based on real world Sensory Signatures using the virtual medium to enhance the effectiveness of that medium. In regards to a video game this would allow, but is not limited to, giving an individual the ability to have proper directional accuracy and a more localized and specific Sensory Stimulation to create a better Virtual Reality (VR) experience. For military this would allow, but is not limited to, a simulation having greater real world quality as the synergistic actuation of multiple Sensory Devices such as EMS, Force, vibration, sound, and airflow create a simulation that cannot be reproduced elsewhere outside of real world activities. Such activities may include the effects of firing a gun, the character running with a heavy pack on their back, climbing, crawling and impacts of being shot and their locations on the body.

Usefulness of the embodiment shown herein may lie in various applications and fields of uses. Further, the multitude of market segment applications, its replicable outcomes and its association with a greater overall architecture provide additional use. The market segments include but are not limited to: entertainment industry, recreation industry, simulation training and medical rehabilitation. The replicable nature of stimulatory activations associated with the predetermined electrical stimulus interface device (electrodes 10)

may allow for the consistency of expected future outcomes in each market application. One way this may be useful is in the video game market, for example, where software creators want their SDK protocols to evoke the same response on the player every time that specific protocol activates the device. The importance of repeatability in accuracy can easily be seen to extend to simulations and training, and medical rehabilitation which require outcomes to be consistent to ensure that the results are as expected to produce specific results.

Furthermore, individuals may be able to have a new, innovative enhanced and repeatable experience with a virtual medium that they were not capable of having before. Through the placement of the electrical stimulus interface (electrodes 10) individuals would be able to properly cover a great many locations of the body. Whether the technology is built into a garment 14 to allow the devices to cover the deltoids, abdominal, thigh, arm and various back muscles on an individual or the technology is built into any form of garment 14. The addition of the individualized local sound gives the individual using the device an immersive feel as they hear sounds as their avatar would. The addition of the Force Simulation Devices such as constriction/compression Stimulation Device actuators or Force/Physics Stimulation Device actuators gives additional sense of realism and is especially applicable in that the individual using the device physically feels the forces acting on them as their avatar does.

For various embodiments, the technology may be the same or similar and just the location of the hardware on an individual's body may be different depending on the particular tissue, nerve or muscles a virtual medium is designed to stimulate. Thus through data sent by the computing device associated with the virtual medium it causes the WPEST technology to interact with the user through tissue, nerve or muscular stimulation that can create but is not limited to varying intensity, duration and radius of the body stimulated.

The invention claimed is:

1. A wearable device for generating a sensory stimulations in a person engaged with an initiating device in at least one of entertainment, training, education, simulation, virtual reality, augmented reality, augmented awareness and gaming, said wearable device comprising:
    a wearable garment;
    an input module in communication with said initiating device to collect sensory related data received from a computing device under control of said initiating device; said sensory related data for controlling the sensory stimulations by a plurality of sensory devices;
    a said plurality of sensory devices connected to the wearable garment that actuate to produce the sensory stimulations, each of said sensory stimulations for inducing physiological stimulation, wherein the plurality of sensory devices receive and/or respond to data, a signal or stimulus, and translates or transfers this input into a form of energy that acts on one or more of the faculties by which the body perceives an external stimulus, the data, signal, or stimulus generated by the at least one of entertainment, training, education, simulation, virtual reality, augmented reality, augmented awareness, and gaming to produce said sensory stimulations, wherein the sensory stimulations produced by the plurality of sensory devices occur in any combination of synchronous, intermittent, consecutive, and imbricate, further wherein the sensory stimulations comprise at least two of electrical muscle stimulation, audio, haptic feedback, force feedback, constriction/compression, airflow, temperature stimulation and combinations thereof; and
    a control centre comprising:
        a processor for determining sensory events, each of said sensory events defining a synergistic action of multiple of the sensory stimulations as a signal pathway to produce one or more sensory outcomes, each of said one or more sensory outcomes for inducing a physiological response or sensory perception;
        a transceiver for receiving the sensory related data collected via the input module, and in response, sending an activating signal to actuate multiple of said sensory devices of the plurality of sensory devices to activate the sensory events;
        said control centre further comprising at least one of the following: i) wherein the control centre stores personalized settings to determine maximum and minimum sensations for the one or more sensory stimulations of the sensory events; ii) where the control centre further actuates a Medically Compliant Electrical Impulse Amplifier Transmitter Receiver (MCEIATR), and combinations thereof,
        further wherein the control centre controls signal, duration, strength, and/or pattern of the sensory stimulations of the sensory events, whether in a sensory event array, random, or other formation and wherein the control centre determines the sensory events using real world sensory signatures, said real world sensory signatures being sensory information output recognizable and perceivable through human senses, each real world sensory signature defining combinations of the sensory stimulations and related control parameters,
        wherein the plurality of sensory devices comprise actuators for audio, force, constriction/compression, vibration and electrical stimulation to produce the sensory stimulations, wherein the plurality of sensory devices comprise electrodes;
        wherein the plurality of sensory devices is removable from the wearable garment;
        wherein the control centre is removable from the wearable garment;
        wherein the wearable garment provides a set number of allowable locations for the electrodes within the wearable garment; and
        wherein positions of the plurality of sensory devices on the wearable garment are user adjustable and the wearable garment comprises visual indicators detailing optional positions of the sensory devices to allow accurate placement.

2. The wearable device of claim 1, wherein the input module collects physiological feedback data of a user of the wearable device in response to activating the sensory events.

3. The wearable device of claim 1, further comprising:
    a decoder to
    i) collect the sensory related data from the input module, the sensory related data being sent from an initiating device, and
    ii) transform the sensory related data into a format compatible with the control centre, wherein the decoder transmits transformed data via a communications protocol to the control centre.

4. The wearable device of claim 3, wherein the control centre processes the transformed data from the decoder to determine the sensory events.

5. The wearable device of claim 1, wherein the input module further collects the sensory related data from the plurality of Sensory Devices.

6. The wearable device of claim 1, wherein the real world sensory signatures are selected from the group consisting of:
   a) electrical stimulation of tissues, nerves and muscles;
   b) sound;
   c) force feedback selected from pushing, pulling and centripetal and centrifugal forces;
   d) vibration;
   e) constriction, compression;
   f) temperature; and
   g) airflow.

7. The wearable device of claim 1, wherein the control centre selectively identifies a subset of the plurality of the sensory devices of an area of the wearable garment to be activated.

8. The wearable device of claim 1, wherein the plurality of sensory devices can deliver multiple types of the sensory stimulations, wherein the sensory stimulations further comprising at least one of Electrical Muscle Stimulation (EMS), Transcutaneous Electrical Nerve Stimulation (TENS), Micro Current Stimulation (MC/FSM), Interferential Stimulation (IFS), Functional Electrical Stimulation (FES) and Neuromuscular Electrical Stimulation (NMES).

9. The wearable device of claim 1, wherein the plurality of sensory devices is connected to the wearable garment in a predetermined and defined placement based on the sensory events.

10. The wearable device of claim 1, wherein the plurality of sensory devices comprises a plurality of speakers to provide individualized local sound for the sensory events.

11. The wearable device of claim 10, wherein said transceiver operatively connected to the input module receives, amplifies and transmits the sensory related data to the speakers.

12. The wearable device of claim 1, wherein the plurality of sensory devices comprises vibration actuators.

13. The wearable device of claim 1, wherein the plurality of sensory devices comprises force stimulation device actuators that apply physical forces to induce particular physiological sensations.

14. The wearable device of claim 1, wherein the plurality of sensory devices comprises force stimulation devices actuators that apply localized forces.

15. The wearable device of claim 14, wherein the force stimulation device actuators alter actuated force based on parameters selected from the group consisting of: amount of force that is applied, speed at which the force reaches its target amount, duration of time during which the force is applied or deactivates once target force is reached, and the speed at which the force is removed, and combinations thereof.

16. The wearable device of claim 1, wherein the plurality of sensory devices comprises constriction/compression stimulation device actuators wherein the constriction/compression stimulation device actuators alter actuated constriction/compression based on various parameters altered to effect the sensation of constriction/compression and squeezing comprising at least one setting selected from the group consisting of pressure, tightening, speed that squeezing or constriction/compression occurs or is removed, the length of time the constriction/compression is activated or deactivated, and the ability to fluctuate between the at least one setting while already activated.

17. The wearable device of claim 1, wherein the plurality of sensory devices comprises force/physics stimulation device actuators that provide capabilities of applying a force comprising at least one of pulling, pushing, centrifugal or centripetal feeling to a location of an individual's body or to the body as a whole.

18. The wearable device of claim 17, wherein the force/physics stimulation device actuators alter actuated force based on various parameters altered to effect the sensation of force/physics comprising at least one setting selected from the group consisting of pushing, pulling, speed that pushing or pulling occurs or is removed, the length of time the pulling or pushing is activated or once activated the force/physics stimulation device actuators revert to deactivated state, and the ability to fluctuate between the at least one setting while already activated.

19. The wearable device of claim 1, wherein the wearable garment is separated into three garment areas, said garment areas comprising an abdominal area, an upper torso or chest and shoulder area, and coverage of both the abdominal and torso area, wherein all three garment areas are interconnected to provide sensory manipulation throughout the entire garment as defined by the signal pathway to create the sensory stimulations to produce the one or more sensory outcomes.

20. A wearable device for generating sensory stimulations, sensory manipulation and user data acquisition in a person engaging in at least one of entertainment, training, education, simulation, virtual reality, augmented reality, augmented awareness and gaming, said device comprising i) wearable material, ii) electrodes and stimulation device actuators, and iii) a Medically Compliant Electrical Impulse Amplifier Transmitter Receiver (MCEIATR), and a control centre, wherein the control centre initiates MCEIATR which in turn provides stimulus through a plurality of sensory devices positioned on the wearable material wherein the stimulus comprises at least two of electrical muscle stimulation, audio, haptic feedback, force feedback, constriction/compression, airflow, temperature stimulation and combinations thereof and wherein the control centre determines sensory events using real world sensory signatures, each real world sensory signature defining combinations of the sensory stimulations and related control parameters, wherein the real world sensory signatures are selected from the group consisting of:
   electrical stimulation of tissues, nerves and muscles;
   sound;
   force feedback selected from pushing, pulling and centripetal and centrifugal forces;
   vibration;
   constriction, compression;
   temperature; and
   airflow;
   wherein the plurality of sensory devices comprise actuators for audio, force, constriction/compression, vibration and electrical stimulation to produce the sensory stimulations, wherein the plurality of sensory devices comprise electrodes; wherein the plurality of sensory devices is removable from the wearable material;
   wherein the control centre is removable from the wearable material;
   wherein the wearable material provides a set number of allowable locations for the electrodes within the wearable material; and
   wherein positions of the plurality of sensory devices on the wearable material are user adjustable and the wearable material comprises visual indicators detailing optional positions of the sensory devices to allow accurate placement.

21. A wearable device system for generating sensory stimulations, sensory manipulation and user data acquisition in at least one of entertainment, training, education, simulation, virtual reality, augmented reality, augmented awareness and gaming, said system comprising:
- wearable material connected to a plurality of sensory devices that actuate to produce the sensory stimulations, each of the sensory stimulations for inducing physiological stimulation, wherein the sensory stimulations produced by the plurality of sensory devices once activated occur singularly or in any combination of synchronous, intermittent, consecutive, and imbricate; an initiating device for creating and transmitting sensory related data;
- a decoder for transforming the sensory related data using a communication protocol;
- a control centre with a signal processor and communications interface, for actuating a Medically Compliant Electrical Impulse Amplifier Transmitter Receiver (MCEIATR), the control centre comprising:
  - the signal processor for determining sensory events, each of the sensory events defining a synergistic action of one or more sensory stimulations as a signal pathway to produce one or more sensory outcomes, each of said one or more sensory outcomes for inducing a physiological response or sensory perception;
  - a transceiver for receiving the sensory related data collected via an input module, and in response, sending an activating signal to actuate one or more sensory devices of the plurality of sensory devices to activate the sensory events;
  - the MCEIATR for providing electrical output to the plurality of sensory devices in response to the activating signal wherein the synergistic action of the one or more sensory
  - stimulations comprise at least two of electrical muscle stimulation, audio, haptic feedback, force feedback, constriction/compression, airflow, temperature stimulation and combinations thereof; and
  - further wherein the control centre controls signal, duration, strength, and/or pattern of the one or more sensory stimulations of the sensory events, whether singularly, in a sensory event array, random, or other formation and wherein the control centre determines the sensory events using real world sensory signatures, each real world sensory signature defining combinations of sensory stimulations and related control parameters;
- wherein the real world sensory signatures are selected from the group consisting of a feeling of:
  - electrical stimulation of tissues, nerves and muscles;
  - sound;
  - force feedback selected from pushing, pulling and centripetal and centrifugal forces;
  - vibration;
  - constriction, compression;
  - temperature; and
  - airflow;
  - wherein the plurality of sensory devices comprise actuators for audio, force, constriction/compression, vibration and electrical stimulation to produce the sensory stimulations, wherein the plurality of sensory devices comprise electrodes; wherein the plurality of sensory devices is removable from the wearable material;
  - wherein the control centre is removable from the wearable material;
  - wherein the wearable material provides a set number of allowable locations for the electrodes within the wearable material; and
  - wherein positions of the plurality of sensory devices on the wearable material are user adjustable and the wearable material comprises visual indicators detailing optional positions of the sensory devices to allow accurate placement.

* * * * *